United States Patent
Chen et al.

(10) Patent No.: US 11,325,936 B2
(45) Date of Patent: May 10, 2022

(54) SIALIDASE INHIBITORS AND PREPARATION THEREOF

(71) Applicant: The Regents of the University of California, Oakland, CA (US)

(72) Inventors: Xi Chen, Davis, CA (US); An Xiao, Davis, CA (US); Wanqing Li, Davis, CA (US); Xixuan Li, Davis, CA (US); Yanhong Li, Davis, CA (US); Teri Slack, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 95 days.

(21) Appl. No.: 16/608,640

(22) PCT Filed: Apr. 27, 2018

(86) PCT No.: PCT/US2018/029965
§ 371 (c)(1),
(2) Date: Oct. 25, 2019

(87) PCT Pub. No.: WO2018/201058
PCT Pub. Date: Nov. 1, 2018

(65) Prior Publication Data
US 2020/0190130 A1    Jun. 18, 2020

Related U.S. Application Data

(60) Provisional application No. 62/542,540, filed on Aug. 8, 2017, provisional application No. 62/491,038, filed on Apr. 27, 2017.

(51) Int. Cl.
*C07H 5/04*    (2006.01)
*C12P 19/28*    (2006.01)
(Continued)

(52) U.S. Cl.
CPC ........... *C07H 5/04* (2013.01); *A61K 31/7012* (2013.01); *C07H 1/00* (2013.01); *C07H 15/207* (2013.01); *C12P 19/26* (2013.01); *C12P 19/28* (2013.01)

(58) Field of Classification Search
None
See application file for complete search history.

(56) References Cited

U.S. PATENT DOCUMENTS 5,312,747 A  *  5/1994  Li .......................... C12P 19/26
                                                            435/200
8,163,281 B2    4/2012  Liu et al.
(Continued)

FOREIGN PATENT DOCUMENTS

WO    WO2017/134466    *  8/2017  ......... A61K 31/7012

OTHER PUBLICATIONS

International Search Report and Written Opinion from PCT/US2018/029965 dated Oct. 16, 2018; 14 pages.
(Continued)

*Primary Examiner* — Eric Olson
(74) *Attorney, Agent, or Firm* — Kilpatrick Townsend and Stockton LLP

(57) ABSTRACT

New 2-deoxy-2,3-dehydro-sialic acids and 2,7-anhydro-sialic acids, which are useful as sialidase inhibitors, and enzymatic methods for preparing them are disclosed. The methods include forming a reaction mixture comprising a glycoside acceptor, a sialic acid donor, and a sialyltransferase; maintaining the reaction mixture under conditions sufficient to form a sialoside; and contacting the sialoside with a *Streptococcus pneumoniae* sialidase to form the sialic acid product. Methods for the inhibition and sialidases and the
(Continued)

US 11,325,936 B2

Page 2

17 Claims, 2 Drawing Sheets

Specification includes a Sequence Listing.

(51) Int. Cl.
C07H 1/00 (2006.01)
C07H 15/207 (2006.01)
C12P 19/26 (2006.01)
A61K 31/7012 (2006.01)

(56) References Cited

U.S. PATENT DOCUMENTS

| | | | |
|---|---|---|---|
| 8,952,183 B2 * | 2/2015 | Schoenhofen | A61P 31/04 549/419 |
| 2014/0302565 A1 * | 10/2014 | Chen | C12N 9/1077 435/97 |
| 2014/0349339 A1 | 11/2014 | Chen et al. | |
| 2015/0064282 A1 | 3/2015 | Josefowitz et al. | |
| 2017/0095443 A1 | 4/2017 | Luo | |

OTHER PUBLICATIONS

Schauer, R. et al.; "New Techniques for the Investigation of Structure and Metabolism of Sialic Acids"; *Ganglioside Structure, Function, and Biomedical Potential*; vol. 174; Dec. 31, 1984; pp. 75-86.
Von Itzstein, M. et al.; "Rational design of potent sialidase-based inhibitors of influenza virus replication"; *Nature*; vol. 363; Jun. 3, 1993; pp. 418-423.
Von Itzstein, M. et al.; "The synthesis of 2,3-didehydro-2,4-dideoxy-4-guanidinyl-N-acetylneuraminic acid: a potent influenza virus sialidase inhibitor"; *Carbohydrate Research*; vol. 259; 1994; pp. 301-305.
Hayden, F.G. et al.; "Safety and Efficacy of the Neuraminidase Inhibitor GG167 in Experimental Human Influenza"; *JAMA*; vol. 275,, No. 4; Jan. 24-31; 1996, pp. 295-299.
Kim, C.U. et al.; "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity"; *J. Am. Chem. Soc.*; vol. 119; 1997; pp. 681-690.
Kim, C.U. et al.; "Structure-Activity Relationship Studies of Novel Carbocyclic Influenza Neuraminidase Inhibitors"; *J. Med. Chem.*; vol. 41, No. 14; 1998; pp. 2451-2460.
Meindl, P. et al.; "Uber 2-Deoxy-2,3-dehydro-sialinsauren, 1. Mitt."; *Monatshefte für Chemie/Chemical Monthly*; vol. 100; 1969; pp. 1295-1306.
Nitabaru, T. et al.; "Catalytic Asymmetric anti-Selective Nitroaldol Reaction En Route to Zanamivir"; *Angewandte Chem. Int. Ed.*; vol. 51; 2012; pp. 1644-1647.
Tian, J. et al.; "Organocatalytic and Scalable Synthesis of the Anti-Influenza Drugs Zanamivir, Laninamivir, and CS-8958"; *Angewandte Chem. Int. Ed.*; vol. 53; 2014; pp. 13885-13888.
Kiefel, M.J. et al.; "Recent Advances in the Synthesis of Sialic Acid Derivatives and Sialylmimetics as Biological Probes"; *Chem. Rev.*; vol. 102; 2002; pp. 471-490.
Laborda, P. et al.; "Influenza Neuraminidase Inhibitors: Synthetic Approaches, Derivatives and Biological Activity"; *Molecules*; vol. 21; 2016; 1513; 40 pages.
Hemeon, I. et al.; "Sialic Acid and Structural Analogues: Stereoselective Syntheses"; *Synthesis 2007*; No. 13; Jun. 18, 2007; pp. 1899-1926.
Claesson, A. et al.; "Synthesis of alpha,beta-Unsaturated Analogues of KDO and N-Acetyl-neuraminic Acid by Trimethylsilyl Trlflate-catalyzed Elimination Reactions"; *Acta Chemical Scandinavica B 36*; No. 10; 1982; pp. 719-720.

treatment of cancer and infectious diseases are also disclosed.

Li, Y. et al.; "Identifying selective inhibitors against the human cytosolic sialidase NEU2 by substrate specificity studies"; *Mol. BioSyst.*; vol. 7; 2011; pp. 1060-1072.
Roggentin, P. et al.; "Diversity in the Properties of Two Sialidase Isoenzymes Produced by *Clostridium perfringens*spp."; *Biological Chemistry Hoppe-Seyler*; vol. 376; Sep. 1995; pp. 569-576.
Li, J. et al.; "The Sialidases of *Clostridium perfringens* Type D Strain CN3718 Differ in Their Properties and Sensitivities to Inhibitors"; *Applied and Environmental Microbiology*; vol. 80, No. 5; Mar. 2014; pp. 1701-1709.
Watson, J.N. et al.; "Two Nucleophilic Mutants of the *Micromonospora vitidifaciens* Sialidase Operate with Retention of Configuration by Two Different Mechanisms"; *ChemBioChem*; vol. 6; 2005; pp. 1999-2004.
Pettigrew, M.M. et al.; "Variation in the Presence of Neuraminidase Genes among *Streptococcus pneumonia* Isolates with Identical Sequence Types"; *Infection and Immunity*; vol. 74, No. 6; Jun. 2006; pp. 3360-3365.
Xu, G. et al.; "Three *Streptococcus pneumonia* Sialidases: Three Different Products"; *J. Am. Chem. Soc.*; vol. 133; 2011; pp. 1718-1721.
Owen, C.D. et al.; "Structural Insights Into the Specificity and Mechanism of a Sialidase That Products a Sialidase Inhibitor"; *J. Biol. Chem*; vol. 290, No. 46; Nov. 13, 2015; pp. 27736-27748.
Li, Y. et al.; "*Pasteurella multocide* sialic acid aldolase: a promising biocatalyst"; *Appl. Microbiol. Biotechnol.*; vol. 79, No. 6; Jul. 2008; pp. 963-970.
Yu, H. et al.; "Chemoenzymatic synthesis of CMP-sialic acid derivatives by a one-pot two-enzyme system: comparison of substrate flexibility of three microbial CMP-sialic acid synthetases"; *Bioorganic and Medicinal Chemistry*; vol. 12; 2004: pp. 6427-6435.
Yu, H. et al.; "A Multifunctional *Pasteurella multocida* Sialyltransferase: A Powerful Tool for the Synthesis of Sialoside Libraries"; *J Am Chem Soc*.; vol. 127; 2005; pp. 17618-17619.
Sugiarto, G. et al.; "A Sialyltransferase Mutant with Decreased Donor Hydrolysis and Reduced Sialidase Activities for Directly Sialylating Lewis"; *ACS Chem. Biol.*; vol. 7; May 14, 2012; pp. 1232-1240.
Parker, R.B. et al.; "Sialidase specificity determined by chemoselective modification of complex sialylated glycans"; *ACS Chem. Biol.*; vol. 7, No. 9; Sep. 21, 2012; pp. 1509-1514.
Bardor, M. et al.; "Mechanism of Uptake and Incorporation of the Non-human Sialic Acid N-Glycolylneuraminic Acid into Human Cells"; *J. Biol. Chem.*; vol. 280, No. 6; Feb. 11, 2005; pp. 4228-4237.
Yu, H. et al.; "One-pot three-enzyme chemoenzymatic approach to the synthesis of sialosides containing natural and non-natural functionalities"; *Nature Protocols*; vol. 1, No. 5; 2006; pp. 2485-2492.
Li, Y. et al.; "*Pasteurella multocida* CMP-sialic acid synthetase and mutants of *Neisseria meningitides* CMP-sialic acid synthetase with improved substrate promiscuity "; *Appl. Microbiol. Biotechnol*;. vol. 93; 2012; pp. 2411-2423.
Khedri, Z. et al.; "A Chemical Biology Solution to Problems with Studying Biologically Important but Unstable 9-O-Acetyl Sialic Acids"; *ACS Chem. Biol.*; vol. 12, No. 1; Jan. 20, 2017; pp. 214-224.
Zbiral, E. et al.; "Synthesis of 2,7-, 2,8-, and 2,9-Dideoxy- and 2,4,7-Trideoxy-2,3-didehydro-N-acetylneuraminic Acids and Their Behavior Towards Sialidase from *Vibrio cholerae*"; *Liebigs Annalen der Chemie*; 1989; pp. 159-165.
Honda, T. et al.; "Synthesis and Anti-Influenza Virus Activity of 4-Guanidino-7-substituted Neu5Ac2en Derivatives"; *Bioorg. Med. Chem. Lett.*; vol. 12; 2002; pp. 1921-1924.
Magesh, S. et al.; "Design, synthesis, and biological evaluation of human sialidase inhibitors. Part 1: Selective inhibitors of lysosomal sialidase (NEU1)"; *Bioorg. Med. Chem. Lett.*; vol. 18; 2008; pp. 532-537.
Magesh, S. et al.; "Evaluation of a Set of C9 N-acyl Neu5Ac2en Mimetics as Viral Sialidase Selective Inhibitors"; *Int. J. Med. Chem.*; 2011; Article ID 539245; 7 pages.
Sriwilaijaroen, N. et al.; "A Novel Potent and Highly Specific Inhibitor against Influenza Viral N1-N9 Neuraminidases: Insight into Neuraminidase-Inhibitor Interactions"; *J. Med. Chem.*; vol. 59; 2016; pp. 4563-4577.

(56) References Cited

OTHER PUBLICATIONS

Gut, H. et al.; "Structural and functional studies of *Streptococcus pneumonia* neuraminidase B: An intramolecular trans-sialidase"; *FEBS Letters*; vol. 582; 2008; pp. 3348-3352.

Xiao, A. et al.; "Sialidase-catalyzed one-pot multienzyme (OPME) synthesis of sialidase transition-state analogue inhibitors"; *ACS Catal.*; vol. 8, No. 1; Jan. 5, 2018; pp. 43-47.

Xiao, A. et al.; "Supporting Information; Sialidase-catalyzed one-pot multienzyme (OPME) synthesis of sialidase transition-state analogue inhibitors"; *ACS Catal.*; vol. 8, No. 1; Jan. 5, 2018; pp. S1-820.

Xu, G. et al.; "Crystal Structure of the NanB Sialidase from *Streptococcus pneumonia*"; *J. Mol. Biol.*; vol. 384; 2008; pp. 436-449.

Berry, A.M. et al.; "Cloning and Characterization of *nanB*, a Second *Streptococcus pneumonia* Neuraminidase Gene, and Purification of the NanB Enzyme from Recombinant *Escherichia coli*"; *J. Bacteriol.*; vol. 178, No. 16; Aug. 1996; pp. 4854-4860.

Lifely, M.R. et al.; "Formation and Identification of two Novel Anhydro Compounds Obtained by Methanolysis of N-Acetylneuraminic Acid and Carboxyl-Reduced, Meningococcal B Polysaccharide"; *Carbohydrate Ressearch*; vol. 107; 1982; pp. 187-197.

Suzuki, M. et al.; "Characterization of 2,7-Anhydro-N-Acetylneuraminic Acid in Human Wet Cerumen"; *J. Biochem.*; vol. 97; 1985; pp. 509-515.

Crost, E.H. et al.; "The mucin-degradation strategy of *Ruminococcus gnavus*: The importance of intramolecular trans-sialidases"; *Gut Microbes*; vol. 7, No. 4; 2016; pp. 302-312.

Furuhata, K. et al.; "Studies on Sialic Acids XXIV. Synthesis of 2,7-Anhydro-N-Aacetylneuraminic Acid"; *Chem. Pharm. Bull.*; vol. 39, No. 3; Mar. 1991; pp. 817-819.

Furuhata, K. et al.; "Studies on Sialic Acids XXX. Synthesis of 2,7-Anhydrosialic Acid"; *Chem. Pharm. Bull.*; vol. 40, No. 12; Dec. 1992; pp. 3197-3200.

Asressu, K.H. et al.; "Concise synthesis of 2,7-anhydrosialic acid derivatives and its application"; *Carbohydrate Research*; vol. 453-454; 2017; pp. 44-53.

Monestier, M. et al.; "Membrane-enclosed multienzyme (MEME) synthesis of 2,7-anhydro-sialic acid derivatives"; *Carbohydrate Research*; vol. 451; Nov. 8, 2017; pp. 110-117.

Owen, C.D. et al.; "Unravelling the specificity and mechanism of sialic acid recognition by the gut symbiont *Ruminococcus gnavus*"; *Nature Communications*; vol. 8, No. 2196; 2017; 15 pages.

\* cited by examiner

```
SEQUENCE LISTING

<160> NUMBER OF SEQ ID NOS: 12

<210> SEQ ID NO 1
<211> LENGTH: 739
<212> TYPE: PRT
<213> ORGANISM: Streptococcus pneumoniae

<400> SEQUENCE: 1

Lys Lys Asn Ile Lys Gln Tyr Val Thr Leu Gly Thr Val Val Leu
1               5                   10                  15

Ser Ala Phe Val Ala Asn Ser Val Ala Ala Gln Glu Thr Glu Thr Ser
            20                  25                  30

Glu Val Ser Thr Pro Glu Leu Val Gln Pro Val Ala Pro Thr Thr Ser
        35                  40                  45

Ile Ser Glu Val Gln His Lys Ser Gly Asn Ser Ser Glu Val Thr Val
    50                  55                  60

Gln Pro Arg Thr Val Glu Thr Thr Val Lys Asp Pro Ser Ser Thr Ala
65                  70                  75                  80

Glu Glu Thr Leu Val Leu Glu Lys Asn Asn Val Thr Leu Thr Gly Gly
                85                  90                  95

Gly Glu Asn Val Thr Lys Glu Leu Lys Asp Lys Phe Thr Ser Gly Asp
            100                 105                 110

Phe Thr Val Val Ile Lys Tyr Asn Gln Ser Ser Glu Lys Gly Leu Gln
        115                 120                 125

Ala Leu Phe Gly Ile Ser Asn Ser Lys Pro Gly Gln Gln Asn Ser Tyr
    130                 135                 140

Val Asp Val Phe Leu Arg Asp Asn Gly Glu Leu Gly Met Glu Ala Arg
145                 150                 155                 160

Asp Thr Ser Ser Asn Lys Asn Asn Leu Val Ser Arg Pro Ala Ser Val
                165                 170                 175

Trp Gly Lys Tyr Lys Gln Glu Ala Val Thr Asn Thr Val Ala Val Val
            180                 185                 190

Ala Asp Ser Val Lys Lys Thr Tyr Ser Leu Tyr Ala Asn Gly Thr Lys
        195                 200                 205

Val Val Glu Lys Lys Val Asp Asn Phe Leu Asn Ile Lys Asp Ile Lys
    210                 215                 220

Gly Ile Asp Tyr Tyr Met Leu Gly Gly Val Lys Arg Ala Gly Lys Thr
225                 230                 235                 240

Ala Phe Gly Phe Asn Gly Thr Leu Glu Asn Ile Lys Phe Phe Asn Ser
                245                 250                 255

Ala Leu Asp Glu Glu Thr Val Lys Lys Met Thr Thr Asn Ala Val Thr
            260                 265                 270

Gly His Leu Ile Tyr Thr Ala Asn Asp Thr Thr Gly Ser Asn Tyr Phe
        275                 280                 285

Arg Ile Pro Val Leu Tyr Thr Phe Ser Asn Gly Arg Val Phe Ser Ser
    290                 295                 300

Ile Asp Ala Arg Tyr Gly Gly Thr His Asp Phe Leu Asn Lys Ile Asn
305                 310                 315                 320
```

```
Ile Ala Thr Ser Tyr Ser Asp Asn Gly Lys Thr Trp Thr Lys Pro
                325                 330                 335

Lys Leu Thr Leu Ala Phe Asp Asp Phe Ala Pro Val Pro Leu Glu Trp
                340                 345                 350

Pro Arg Glu Val Gly Gly Arg Asp Leu Gln Ile Ser Gly Gly Ala Thr
                355                 360                 365

Tyr Ile Asp Ser Val Ile Val Glu Lys Lys Asn Lys Gln Val Leu Met
                370                 375                 380

Phe Ala Asp Val Met Pro Ala Gly Val Ser Phe Arg Glu Ala Thr Arg
385                 390                 395                 400

Lys Asp Ser Gly Tyr Lys Gln Ile Asp Gly Asn Tyr Tyr Leu Lys Leu
                405                 410                 415

Arg Lys Gln Gly Asp Thr Asp Tyr Asn Tyr Thr Ile Arg Glu Asn Gly
                420                 425                 430

Thr Val Tyr Asp Asp Arg Thr Asn Arg Pro Thr Glu Phe Ser Val Asp
                435                 440                 445

Lys Asn Phe Gly Ile Lys Gln Asn Gly Asn Tyr Leu Thr Val Glu Gln
                450                 455                 460

Tyr Ser Val Ser Phe Glu Asn Asn Lys Lys Thr Glu Tyr Arg Asn Gly
465                 470                 475                 480

Thr Lys Val His Met Asn Ile Phe Tyr Lys Asp Ala Leu Phe Lys Val
                485                 490                 495

Val Pro Thr Asn Tyr Ile Ala Tyr Ile Ser Ser Asn Asp His Gly Glu
                500                 505                 510

Ser Trp Ser Ala Pro Thr Leu Leu Pro Pro Ile Met Gly Leu Asn Arg
                515                 520                 525

Asn Ala Pro Tyr Leu Gly Pro Gly Arg Gly Ile Ile Glu Ser Ser Thr
                530                 535                 540

Gly Arg Ile Leu Ile Pro Ser Tyr Thr Gly Lys Glu Ser Ala Phe Ile
545                 550                 555                 560

Tyr Ser Asp Asp Asn Gly Ala Ser Trp Lys Val Lys Val Val Pro Leu
                565                 570                 575

Pro Ser Ser Trp Ser Ala Glu Ala Gln Phe Val Glu Leu Ser Pro Gly
                580                 585                 590

Val Ile Gln Ala Tyr Met Arg Thr Asn Asn Gly Lys Ile Ala Tyr Leu
                595                 600                 605

Thr Ser Lys Asp Ala Gly Thr Thr Trp Ser Ala Pro Glu Tyr Leu Lys
                610                 615                 620

Phe Val Ser Asn Pro Ser Tyr Gly Thr Gln Leu Ser Ile Ile Asn Tyr
625                 630                 635                 640

Ser Gln Leu Ile Asp Gly Lys Lys Ala Val Ile Leu Ser Thr Pro Asn
                645                 650                 655

Ser Thr Asn Gly Arg Lys His Gly Gln Ile Trp Ile Gly Leu Ile Asn
                660                 665                 670

Asp Asp Asn Thr Ile Asp Trp Arg Tyr His His Asp Val Asp Tyr Ser
                675                 680                 685

Asn Tyr Gly Tyr Ser Tyr Ser Thr Leu Thr Glu Leu Pro Asn His Glu
                690                 695                 700

Ile Gly Leu Met Phe Glu Lys Phe Asp Ser Trp Ser Arg Asn Glu Leu
705                 710                 715                 720

His Met Lys Asn Val Val Pro Tyr Ile Thr Phe Lys Ile Glu Asp Leu
                725                 730                 735
```

Lys Lys Asn

<210> SEQ ID NO 2
<211> LENGTH: 739
<212> TYPE: PRT
<213> ORGANISM: Streptococcus pneumoniae

<400> SEQUENCE: 2

```
Lys Lys Asn Ile Lys Gln Tyr Val Thr Leu Gly Thr Val Val Leu
1               5                   10                  15

Ser Ala Phe Val Ala Asn Ser Val Ala Ala Gln Glu Thr Glu Thr Ser
            20                  25                  30

Glu Val Ser Thr Pro Lys Leu Val Gln Pro Val Ala Pro Thr Thr Pro
            35                  40                  45

Ile Ser Glu Val Gln Pro Thr Ser Asp Asn Ser Ser Glu Val Thr Val
    50                  55                  60

Gln Pro Arg Thr Val Glu Thr Val Lys Asp Pro Ser Ser Thr Ala
65                  70                  75                  80

Glu Glu Thr Pro Val Leu Glu Lys Asn Asn Val Thr Leu Thr Gly Gly
                    85                  90                  95

Gly Glu Asn Val Thr Lys Glu Leu Lys Asp Lys Phe Thr Ser Gly Asp
                100                 105                 110

Phe Thr Val Val Ile Lys Tyr Asn Gln Ser Ser Glu Lys Gly Leu Gln
            115                 120                 125

Ala Leu Phe Gly Ile Ser Asn Ser Lys Pro Gly Gln Gln Asn Ser Tyr
130                 135                 140

Val Asp Val Phe Leu Arg Asp Asn Gly Glu Leu Gly Met Glu Ala Arg
145                 150                 155                 160

Asp Thr Ser Ser Asn Lys Asn Asn Leu Val Ser Arg Pro Ala Ser Val
                165                 170                 175

Trp Gly Lys Tyr Lys Gln Glu Ala Val Thr Asn Thr Val Ala Val Val
            180                 185                 190

Ala Asp Ser Val Lys Lys Thr Tyr Ser Leu Tyr Ala Asn Gly Thr Lys
            195                 200                 205

Val Val Glu Lys Lys Val Asp Asn Phe Leu Asn Ile Lys Asp Ile Lys
210                 215                 220

Gly Ile Asp Tyr Tyr Met Leu Gly Gly Val Lys Arg Ala Gly Lys Thr
225                 230                 235                 240

Ala Phe Gly Phe Asn Gly Thr Leu Glu Asn Ile Lys Phe Phe Asn Ser
                245                 250                 255

Ala Leu Asp Glu Glu Thr Val Lys Lys Met Thr Thr Asn Ala Val Thr
            260                 265                 270

Gly His Leu Ile Tyr Thr Ala Asn Asp Thr Thr Gly Ser Asn Tyr Phe
            275                 280                 285

Arg Ile Pro Val Leu Tyr Thr Phe Ser Asn Gly Arg Val Phe Ser Ser
290                 295                 300

Ile Asp Ala Arg Tyr Gly Gly Thr His Asp Phe Leu Asn Lys Ile Asn
305                 310                 315                 320

Ile Ala Thr Ser Tyr Ser Asp Asp Asn Gly Lys Thr Trp Thr Lys Pro
                325                 330                 335

Lys Leu Thr Leu Ala Phe Asp Asp Phe Ala Pro Val Pro Leu Glu Trp
            340                 345                 350

Pro Arg Glu Val Gly Gly Arg Asp Leu Gln Ile Ser Gly Gly Ala Thr
            355                 360                 365
```

Tyr Ile Asp Ser Val Ile Val Glu Lys Lys Asn Lys Gln Val Leu Met
    370                 375                 380

Phe Ala Asp Val Met Pro Ala Gly Val Ser Phe Arg Glu Ala Thr Arg
385                 390                 395                 400

Lys Asp Ser Gly Tyr Lys Gln Ile Asp Gly Asn Tyr Tyr Leu Lys Leu
                405                 410                 415

Arg Lys Gln Gly Asp Thr Asp Tyr Asn Tyr Thr Ile Arg Glu Asn Gly
            420                 425                 430

Thr Val Tyr Asp Asp Arg Thr Asn Arg Pro Thr Glu Phe Ser Val Asp
        435                 440                 445

Lys Asn Phe Gly Ile Lys Gln Asn Gly Asn Tyr Leu Thr Val Glu Gln
450                 455                 460

Tyr Ser Val Ser Phe Glu Asn Asn Lys Lys Thr Glu Tyr Arg Asn Gly
465                 470                 475                 480

Thr Lys Val His Met Asn Ile Phe Tyr Lys Asp Ala Leu Phe Lys Val
                485                 490                 495

Val Pro Thr Asn Tyr Ile Ala Tyr Ile Ser Ser Asn Asp His Gly Glu
            500                 505                 510

Ser Trp Ser Ala Pro Thr Leu Leu Pro Pro Ile Met Gly Leu Asn Arg
        515                 520                 525

Asn Ala Pro Tyr Leu Gly Pro Gly Arg Gly Ile Ile Glu Ser Ser Thr
530                 535                 540

Gly Arg Ile Leu Ile Pro Ser Tyr Thr Gly Lys Glu Ser Ala Phe Ile
545                 550                 555                 560

Tyr Ser Asp Asp Asn Gly Ala Ser Trp Lys Val Lys Val Val Pro Leu
                565                 570                 575

Pro Ser Ser Trp Ser Ala Glu Ala Gln Phe Val Glu Leu Ser Pro Gly
            580                 585                 590

Val Ile Gln Ala Tyr Met Arg Thr Asn Asn Gly Lys Ile Ala Tyr Leu
        595                 600                 605

Thr Ser Lys Asp Ala Gly Thr Thr Trp Ser Ala Pro Glu Tyr Leu Lys
610                 615                 620

Phe Val Ser Asn Pro Ser Tyr Gly Thr Gln Leu Ser Ile Ile Asn Tyr
625                 630                 635                 640

Ser Gln Leu Ile Asp Gly Lys Lys Ala Val Ile Leu Ser Thr Pro Asn
                645                 650                 655

Ser Thr Asn Gly Arg Lys His Gly Gln Ile Trp Ile Gly Leu Ile Asn
            660                 665                 670

Asp Asp Asn Thr Ile Asp Trp Arg Tyr His His Asp Val Asp Tyr Ser
        675                 680                 685

Asn Tyr Gly Tyr Ser Tyr Ser Thr Leu Thr Glu Leu Pro Asn His Glu
690                 695                 700

Ile Gly Leu Met Phe Glu Lys Phe Asp Ser Trp Ser Arg Asn Glu Leu
705                 710                 715                 720

His Met Lys Asn Val Val Pro Tyr Ile Thr Phe Lys Ile Glu Asp Leu
                725                 730                 735

Lys Lys Asn

<210> SEQ ID NO 3
<211> LENGTH: 668
<212> TYPE: PRT
<213> ORGANISM: Streptococcus pneumoniae

<400> SEQUENCE: 3

-continued

```
Asn Glu Leu Asn Tyr Gly Gln Leu Ser Ile Ser Pro Ile Phe Gln Gly
1               5                   10                  15

Gly Ser Tyr Gln Leu Asn Asn Lys Ser Ile Asp Ile Ser Pro Leu Leu
            20                  25                  30

Leu Asp Lys Leu Ser Gly Asp Ser Gln Thr Val Val Met Lys Phe Lys
        35                  40                  45

Ala Asp Lys Pro Asn Ser Leu Gln Ala Leu Phe Gly Leu Ser Asn Ser
    50                  55                  60

Lys Ala Gly Phe Lys Asn Asn Tyr Phe Ser Ile Phe Met Arg Asp Ser
65                  70                  75                  80

Gly Glu Ile Gly Val Glu Ile Arg Asp Ala Gln Lys Gly Ile Asn Tyr
                85                  90                  95

Leu Phe Ser Arg Pro Ala Ser Leu Trp Gly Lys His Lys Gly Gln Ala
            100                 105                 110

Val Glu Asn Thr Leu Val Phe Val Ser Asp Ser Lys Asp Lys Thr Tyr
            115                 120                 125

Thr Met Tyr Val Asn Gly Ile Glu Val Phe Ser Glu Thr Val Asp Thr
    130                 135                 140

Phe Leu Pro Ile Ser Asn Ile Asn Gly Ile Asp Lys Ala Thr Leu Gly
145                 150                 155                 160

Ala Val Asn Arg Glu Gly Lys Glu His Tyr Leu Ala Lys Gly Ser Ile
                165                 170                 175

Asp Glu Ile Ser Leu Phe Asn Lys Ala Ile Ser Asp Gln Glu Val Ser
            180                 185                 190

Thr Ile Pro Leu Ser Asn Pro Phe Gln Leu Ile Phe Gln Ser Gly Asp
            195                 200                 205

Ser Thr Gln Ala Asn Tyr Phe Arg Ile Pro Thr Leu Tyr Thr Leu Ser
    210                 215                 220

Ser Gly Arg Val Leu Ser Ser Ile Asp Ala Arg Tyr Gly Gly Thr His
225                 230                 235                 240

Asp Ser Lys Ser Lys Ile Asn Ile Ala Thr Ser Tyr Ser Asp Asp Asn
                245                 250                 255

Gly Lys Thr Trp Ser Glu Pro Ile Phe Ala Met Lys Phe Asn Asp Tyr
            260                 265                 270

Glu Glu Gln Leu Val Tyr Trp Pro Arg Asp Asn Lys Leu Lys Asn Ser
            275                 280                 285

Gln Ile Ser Gly Ser Ala Ser Phe Ile Asp Ser Ser Ile Val Glu Asp
    290                 295                 300

Lys Lys Ser Gly Lys Thr Ile Leu Leu Ala Asp Val Met Pro Ala Gly
305                 310                 315                 320

Ile Gly Asn Asn Asn Ala Asn Lys Ala Asp Ser Gly Phe Lys Glu Ile
                325                 330                 335

Asn Gly His Tyr Tyr Leu Lys Leu Lys Lys Asn Gly Asp Asn Asp Phe
            340                 345                 350

Arg Tyr Thr Val Arg Glu Asn Gly Val Val Tyr Asp Glu Thr Thr Asn
    355                 360                 365

Lys Pro Thr Asn Tyr Thr Ile Asn Asp Lys Tyr Glu Val Leu Glu Gly
    370                 375                 380

Gly Lys Ser Leu Thr Val Glu Gln Tyr Ser Val Asp Phe Asp Ser Gly
385                 390                 395                 400

Ser Leu Arg Glu Arg His Asn Gly Lys Gln Val Pro Met Asn Val Phe
            405                 410                 415

Tyr Lys Asp Ser Leu Phe Lys Val Thr Pro Thr Asn Tyr Ile Ala Met
```

```
                    420             425             430
Thr Thr Ser Gln Asn Arg Gly Glu Ser Trp Glu Gln Phe Lys Leu Leu
            435             440             445

Pro Pro Phe Leu Gly Glu Lys His Asn Gly Thr Tyr Leu Cys Pro Gly
            450             455             460

Gln Gly Leu Ala Leu Lys Ser Ser Asn Arg Leu Ile Phe Ala Thr Tyr
465             470             475             480

Thr Ser Gly Glu Leu Thr Tyr Leu Ile Ser Asp Asp Ser Gly Gln Thr
            485             490             495

Trp Lys Lys Ser Ser Ala Ser Ile Pro Phe Glu Asn Ala Thr Ala Glu
            500             505             510

Ala Gln Met Val Glu Leu Arg Asp Gly Val Ile Arg Thr Phe Phe Arg
            515             520             525

Thr Thr Thr Gly Lys Ile Ala Tyr Met Thr Ser Arg Asp Ser Gly Glu
            530             535             540

Thr Trp Ser Glu Val Ser Tyr Ile Asp Gly Ile Gln Gln Thr Ser Tyr
545             550             555             560

Gly Thr Gln Val Ser Ala Ile Lys Tyr Ser Gln Leu Ile Asp Gly Lys
            565             570             575

Glu Ala Val Ile Leu Ser Thr Pro Asn Ser Arg Ser Gly Arg Lys Gly
            580             585             590

Gly Gln Leu Val Val Gly Leu Val Asn Lys Glu Asp Asp Ser Ile Asp
            595             600             605

Trp Lys Tyr His Tyr Asp Ile Asp Leu Pro Ser Tyr Gly Tyr Ala Tyr
            610             615             620

Ser Ala Ile Thr Glu Leu Pro Asn His His Ile Gly Val Leu Phe Glu
625             630             635             640

Lys Tyr Asp Ser Trp Ser Arg Asn Glu Leu His Leu Ser Asn Val Val
            645             650             655

Gln Tyr Ile Asp Leu Glu Ile Asn Asp Leu Thr Lys
            660             665

<210> SEQ ID NO 4
<211> LENGTH: 387
<212> TYPE: PRT
<213> ORGANISM: Pasteurella multocida

<400> SEQUENCE: 4

Lys Thr Ile Thr Leu Tyr Leu Asp Pro Ala Ser Leu Pro Ala Leu Asn
1               5               10              15

Gln Leu Met Asp Phe Thr Gln Asn Asn Glu Asp Lys Thr His Pro Arg
            20              25              30

Ile Phe Gly Leu Ser Arg Phe Lys Ile Pro Asp Asn Ile Ile Thr Gln
            35              40              45

Tyr Gln Asn Ile His Phe Val Glu Leu Lys Asp Asn Arg Pro Thr Glu
        50              55              60

Ala Leu Phe Thr Ile Leu Asp Gln Tyr Pro Gly Asn Ile Glu Leu Asn
65              70              75              80

Ile His Leu Asn Ile Ala His Ser Val Gln Leu Ile Arg Pro Ile Leu
            85              90              95

Ala Tyr Arg Phe Lys His Leu Asp Arg Val Ser Ile Gln Gln Leu Asn
            100             105             110

Leu Tyr Asp Asp Gly Ser Asp Glu Tyr Val Asp Leu Glu Lys Glu Glu
            115             120             125
```

-continued

```
Asn Lys Asp Ile Ser Ala Glu Ile Lys Gln Ala Glu Lys Gln Leu Ser
    130                 135                 140

His Tyr Leu Leu Thr Gly Lys Ile Lys Phe Asp Asn Pro Thr Ile Ala
145                 150                 155                 160

Arg Tyr Val Trp Gln Ser Ala Phe Pro Val Lys Tyr His Phe Leu Ser
                165                 170                 175

Thr Asp Tyr Phe Glu Lys Ala Glu Phe Leu Gln Pro Leu Lys Glu Tyr
            180                 185                 190

Leu Ala Glu Asn Tyr Gln Lys Met Asp Trp Thr Ala Tyr Gln Gln Leu
        195                 200                 205

Thr Pro Glu Gln Gln Ala Phe Tyr Leu Thr Leu Val Gly Phe Asn Asp
    210                 215                 220

Glu Val Lys Gln Ser Leu Glu Val Gln Gln Ala Lys Phe Ile Phe Thr
225                 230                 235                 240

Gly Thr Thr Thr Trp Glu Gly Asn Thr Asp Val Arg Glu Tyr Tyr Ala
                245                 250                 255

Gln Gln Gln Leu Asn Leu Leu Asn His Phe Thr Gln Ala Glu Gly Asp
            260                 265                 270

Leu Phe Ile Gly Asp His Tyr Lys Ile Tyr Phe Lys Gly His Pro Arg
        275                 280                 285

Gly Gly Glu Ile Asn Asp Tyr Ile Leu Asn Asn Ala Lys Asn Ile Thr
    290                 295                 300

Asn Ile Pro Ala Asn Ile Ser Phe Glu Val Leu Met Met Thr Gly Leu
305                 310                 315                 320

Leu Pro Asp Lys Val Gly Gly Val Ala Ser Ser Leu Tyr Phe Ser Leu
                325                 330                 335

Pro Lys Glu Lys Ile Ser His Ile Ile Phe Thr Ser Asn Lys Gln Val
            340                 345                 350

Lys Ser Lys Glu Asp Ala Leu Asn Asn Pro Tyr Val Lys Val Met Arg
        355                 360                 365

Arg Leu Gly Ile Ile Asp Glu Ser Gln Val Ile Phe Trp Asp Ser Leu
    370                 375                 380

Lys Gln Leu
385

<210> SEQ ID NO 5
<211> LENGTH: 307
<212> TYPE: PRT
<213> ORGANISM: Pasteurella multocida

<400> SEQUENCE: 5

Asn Leu Ile Ile Cys Cys Thr Pro Leu Gln Val Leu Ile Ala Glu Lys
1               5                   10                  15

Ile Ile Ala Lys Phe Pro His Thr Pro Phe Tyr Gly Val Met Leu Ser
            20                  25                  30

Thr Val Ser Asn Lys Lys Phe Asp Phe Tyr Ala Lys Arg Leu Ala Gln
        35                  40                  45

Gln Cys Gln Gly Phe Phe Ser Met Val Gln His Lys Asp Arg Phe Asn
    50                  55                  60

Leu Leu Lys Glu Ile Leu Tyr Leu Lys Arg Thr Phe Ser Gly Lys His
65                  70                  75                  80

Phe Asp Gln Val Phe Val Ala Asn Ile Asn Asp Leu Gln Ile Gln Phe
                85                  90                  95

Leu Leu Ser Ala Ile Asp Phe Asn Leu Leu Asn Thr Phe Asp Asp Gly
            100                 105                 110
```

```
Thr Ile Asn Ile Val Pro Asn Ser Leu Phe Tyr Gln Asp Asp Pro Ala
            115                 120                 125

Thr Leu Gln Arg Lys Leu Ile Asn Val Leu Leu Gly Asn Lys Tyr Ser
    130                 135                 140

Ile Gln Ser Leu Arg Ala Leu Ser His Thr His Tyr Thr Ile Tyr Lys
145                 150                 155                 160

Gly Phe Lys Asn Ile Ile Glu Arg Val Glu Pro Ile Glu Leu Val Ala
                165                 170                 175

Ala Asp Asn Ser Glu Lys Val Thr Ser Ala Val Ile Asn Val Leu Leu
            180                 185                 190

Gly Gln Pro Val Phe Ala Glu Asp Glu Arg Asn Ile Ala Leu Ala Glu
        195                 200                 205

Arg Val Ile Lys Gln Phe Asn Ile His Tyr Tyr Leu Pro His Pro Arg
    210                 215                 220

Glu Lys Tyr Arg Leu Ala Gln Val Asn Tyr Ile Asp Thr Glu Leu Ile
225                 230                 235                 240

Phe Glu Asp Tyr Ile Leu Gln Gln Cys Gln Thr His Lys Tyr Cys Val
                245                 250                 255

Tyr Thr Tyr Phe Ser Ser Ala Ile Ile Asn Ile Met Asn Lys Ser Asp
            260                 265                 270

Asn Ile Glu Val Val Ala Leu Lys Ile Asp Thr Glu Asn Pro Ala Tyr
        275                 280                 285

Asp Ala Cys Tyr Asp Leu Phe Asp Glu Leu Gly Val Asn Val Ile Asp
    290                 295                 300

Ile Arg Glu
305

<210> SEQ ID NO 6
<211> LENGTH: 266
<212> TYPE: PRT
<213> ORGANISM: Pasteurella multocida

<400> SEQUENCE: 6

Asp Lys Phe Ala Glu His Glu Ile Pro Lys Ala Val Ile Val Ala Gly
1               5                   10                  15

Asn Gly Glu Ser Leu Ser Gln Ile Asp Tyr Arg Leu Leu Pro Lys Asn
            20                  25                  30

Tyr Asp Val Phe Arg Cys Asn Gln Phe Tyr Phe Glu Glu Arg Tyr Phe
        35                  40                  45

Leu Gly Asn Lys Ile Lys Ala Val Phe Thr Pro Gly Val Phe Leu
    50                  55                  60

Glu Gln Tyr Tyr Thr Leu Tyr His Leu Lys Arg Asn Asn Glu Tyr Phe
65                  70                  75                  80

Val Asp Asn Val Ile Leu Ser Ser Phe Asn His Pro Thr Val Asp Leu
                85                  90                  95

Glu Lys Ser Gln Lys Ile Gln Ala Leu Phe Ile Asp Val Ile Asn Gly
            100                 105                 110

Tyr Glu Lys Tyr Leu Ser Lys Leu Thr Ala Phe Asp Val Tyr Leu Arg
        115                 120                 125

Tyr Lys Glu Leu Tyr Glu Asn Gln Arg Ile Thr Ser Gly Val Tyr Met
    130                 135                 140

Cys Ala Val Ala Ile Ala Met Gly Tyr Thr Asp Ile Tyr Leu Thr Gly
145                 150                 155                 160

Ile Asp Phe Tyr Gln Ala Ser Glu Glu Asn Tyr Ala Phe Asp Asn Lys
```

```
                    165                 170                 175

Lys Pro Asn Ile Ile Arg Leu Leu Pro Asp Phe Arg Lys Glu Lys Thr
                180                 185                 190

Leu Phe Ser Tyr His Ser Lys Asp Ile Asp Leu Glu Ala Leu Ser Phe
            195                 200                 205

Leu Gln Gln His Tyr His Val Asn Phe Tyr Ser Ile Ser Pro Met Ser
        210                 215                 220

Pro Leu Ser Lys His Phe Pro Ile Pro Thr Val Glu Asp Asp Cys Glu
225                 230                 235                 240

Thr Thr Phe Val Ala Pro Leu Lys Glu Asn Tyr Ile Asn Asp Ile Leu
                245                 250                 255

Leu Val Asp Lys Leu Ala Ala Ala Leu Glu
                260                 265

<210> SEQ ID NO 7
<211> LENGTH: 227
<212> TYPE: PRT
<213> ORGANISM: Neisseria meningitidis

<400> SEQUENCE: 7

Glu Lys Gln Asn Ile Ala Val Ile Leu Ala Arg Gln Asn Ser Lys Gly
1               5                   10                  15

Leu Pro Leu Lys Asn Leu Arg Lys Met Asn Gly Ile Ser Leu Leu Gly
                20                  25                  30

His Thr Ile Asn Ala Ala Ile Ser Ser Lys Cys Phe Asp Arg Ile Ile
            35                  40                  45

Val Ser Thr Asp Gly Gly Leu Ile Ala Glu Glu Ala Lys Asn Phe Gly
        50                  55                  60

Val Glu Val Val Leu Arg Pro Ala Glu Leu Ala Ser Asp Thr Ala Ser
65                  70                  75                  80

Ser Ile Ser Gly Val Ile His Ala Leu Glu Thr Ile Gly Ser Asn Ser
                85                  90                  95

Gly Thr Val Thr Leu Leu Gln Pro Thr Ser Pro Leu Arg Thr Gly Ala
                100                 105                 110

His Ile Arg Glu Ala Phe Ser Leu Phe Asp Glu Lys Ile Lys Gly Ser
            115                 120                 125

Val Val Ser Ala Cys Pro Met Glu His His Pro Leu Lys Thr Leu Leu
        130                 135                 140

Gln Ile Asn Asn Gly Glu Tyr Ala Pro Met Arg His Leu Ser Asp Leu
145                 150                 155                 160

Glu Gln Pro Arg Gln Leu Pro Gln Ala Phe Arg Pro Asn Gly Ala
                165                 170                 175

Ile Tyr Ile Asn Asp Thr Ala Ser Leu Ile Ala Asn Asn Cys Phe Phe
                180                 185                 190

Ile Ala Pro Thr Lys Leu Tyr Ile Met Ser His Gln Asp Ser Ile Asp
            195                 200                 205

Ile Asp Thr Glu Leu Asp Leu Gln Gln Ala Glu Asn Ile Leu His His
        210                 215                 220

Lys Glu Ser
225

<210> SEQ ID NO 8
<211> LENGTH: 222
<212> TYPE: PRT
<213> ORGANISM: Pasteurella multocida
```

-continued

<400> SEQUENCE: 8

```
Thr Asn Ile Ala Ile Pro Ala Arg Ala Gly Ser Lys Gly Ile Pro
1               5                   10                  15

Asp Lys Asn Leu Gln Pro Val Gly Gly His Ser Leu Ile Gly Arg Ala
                20                  25                  30

Ile Leu Ala Ala Lys Asn Ala Asp Val Phe Asp Met Ile Val Thr
            35                  40                  45

Ser Asp Gly Asp Asn Ile Leu Arg Glu Ala Glu Lys Tyr Gly Ala Leu
    50                  55                  60

Ala Leu Lys Arg Pro Ala Glu Leu Ala Gln Asp Asn Ser Arg Thr Ile
65                  70                  75                  80

Asp Ala Ile Leu His Ala Leu Glu Ser Leu Asn Ile Arg Glu Gly Thr
                85                  90                  95

Cys Thr Leu Leu Gln Pro Thr Ser Pro Leu Arg Asp His Leu Asp Ile
            100                 105                 110

Lys Asn Ala Met Asp Met Tyr Val Asn Gly Gly Val His Ser Val Val
        115                 120                 125

Ser Ala Cys Glu Cys Glu His His Pro Tyr Lys Ala Phe Ala Leu Ser
    130                 135                 140

Lys Asp His Glu Val Leu Pro Val Arg Glu Ile Ala Asp Phe Glu Ala
145                 150                 155                 160

Val Arg Gln Thr Leu Pro Lys Met Tyr Arg Ala Asn Gly Ala Ile Tyr
                165                 170                 175

Ile Asn Asp Ile Ala Gln Leu Leu Lys Glu Lys Tyr Phe Phe Ile Pro
            180                 185                 190

Pro Leu Lys Phe Tyr Leu Met Pro Thr Tyr His Ser Val Asp Ile Asp
        195                 200                 205

Val Lys Gln Asp Leu Glu Leu Ala Glu Ile Leu Ser Asn Lys
    210                 215                 220
```

<210> SEQ ID NO 9
<211> LENGTH: 35
<212> TYPE: DNA
<213> ORGANISM: Artificial Sequence
<220> FEATURE:
<223> OTHER INFORMATION: Synthetic Construct

<400> SEQUENCE: 9
gatcgaattc atgaaaaaaa atattaaaca atatg                         35

<210> SEQ ID NO 10
<211> LENGTH: 49
<212> TYPE: DNA
<213> ORGANISM: Artificial Sequence
<220> FEATURE:
<223> OTHER INFORMATION: Synthetic Construct

<400> SEQUENCE: 10
acgcaagctt ttagtggtgg tggtggtggt gattctttt cagatcttc            49

<210> SEQ ID NO 11
<211> LENGTH: 30
<212> TYPE: DNA
<213> ORGANISM: Artificial Sequence
<220> FEATURE:
<223> OTHER INFORMATION: Synthetic Construct

<400> SEQUENCE: 11
gatcgaattc ggctcaggag actgaaactt                               30

```
<210> SEQ ID NO 12
<211> LENGTH: 32
<212> TYPE: DNA
<213> ORGANISM: Artificial Sequence
<220> FEATURE:
<223> OTHER INFORMATION: Synthetic Construct

<400> SEQUENCE: 12
acgcctcgag attcttttc agatcttcaa tc                                32
```

SIALIDASE INHIBITORS AND PREPARATION THEREOF

CROSS REFERENCES TO RELATED APPLICATIONS

The present application is a US National Phase Application Under 371 of PCT/US2018/025254 filed Mar. 29, 2018, which claims priority to U.S. Provisional Pat. Appl. No. 62/491,083, filed on Apr. 27, 2017, and U.S. Provisional Pat. Appl. No. 62/542,540, filed on Aug. 8, 2017, each of which applications are incorporated herein by reference in their entirety.

STATEMENT AS TO RIGHTS TO INVENTIONS MADE UNDER FEDERALLY SPONSORED RESEARCH AND DEVELOPMENT

This invention was made with government support under Grant Nos. R01AI130684 and U01GM120419 awarded by the National Institutes of Health. The government has certain rights in the invention.

REFERENCE TO SUBMISSION OF A SEQUENCE LISTING AS A TEXT FILE

The Sequence Listing written in file SequenceListing_1160271.txt created on Oct. 4, 2019, 32,010 bytes, machine format IBM-PC, MS-Windows operating system, is hereby incorporated by reference in its entirety for all purposes.

BACKGROUND OF THE INVENTION

Microbial sialidases are important targets for designing anti-viral and anti-bacterial drugs. Sialic acids are common terminal monosaccharides on the carbohydrate moieties of mammalian cell surface glycoconjugates and play important biological roles. Sialidases or neuraminidases, the exoglycosidases that catalyze the cleavage of the terminal sialic acids, are widely spread in vertebrates and microbes residing in or infecting vertebrates. Viral and bacterial sialidases are therefore attractive targets for designing inhibitors as potent antimicrobial therapeutics.

Sialidase transition state analog inhibitor 2-deoxy-2,3-dehydro-N-acetylneuraminic acid (Neu5Ac2en, DANA) has played a leading role in developing clinically used anti-influenza virus drugs. It was also a lead compound for rational design of clinical anti-influenza virus drugs Relenza (Zanamivir or 4-deoxy-4-guanidino-Neu5Ac2en) and Tamiflu (Oseltamivir). Numerous 2,3-dehydro-2-deoxy-sialic acids (Sia2ens) have been synthesized according to previously reported chemical methods. Chemical modification of selectively protected sialic acids is a common strategy to obtain Sia2ens, which is considered too environmentally unfriendly as organic solvents are used. It also requires multiple protection and deprotection steps.

BRIEF SUMMARY OF THE INVENTION

In some embodiments, there is provided a method for forming a sialic acid product selected from the group consisting of a 2-deoxy-2,3-dehydro-sialic acid, a 2,7-anhydro-sialic acid, and derivatives thereof. The method includes: forming a reaction mixture comprising a glycoside acceptor, a sialic acid donor, and a sialyltransferase; maintaining the reaction mixture under conditions sufficient to form a sialoside; and contacting the sialoside with a *Streptococcus pneumoniae* sialidase to form the sialic acid product.

In some embodiments, SpNanC is used for forming 2-deoxy-2,3-dehydro-sialic acids. In some embodiments, SpNanB is use for forming 2,7-anhydro-sialic acids.

In some embodiments, the method further includes contacting a sialic acid and a CMP-sialic acid synthetase in the presence of CTP to form a CMP-sialic acid for use as the sialic acid donor. In some embodiments, the method further includes contacting a $C_6$-monosaccharide and a sialic acid aldolase in the presence of pyruvate to form to the sialic acid. In some embodiments, forming the sialic acid, forming the CMP-sialic acid, forming the sialoside, and forming the sialic acid product are conducted in one pot.

Compounds according to Formula I, and salts thereof, are also provided:

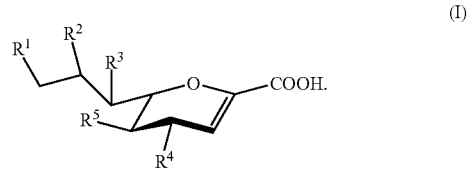

(I)

For compounds of Formula I:
$R^1$, $R^2$, $R^3$, and $R^4$ are independently selected from the group consisting of —NHC(O)$R^a$, —$N_3$, —$NH_2$, —NH$R^a$, —OC(O)$R^a$, —OH, and hydrogen;
$R^5$ is selected from the group consisting of —NHAc, —NHGc, —NHC(O)$R^a$, —$N_3$, —$NH_2$, —OC(O)$R^a$, —OH, and hydrogen;
each $R^a$ is independently selected from the group consisting of optionally substituted $C_{1-12}$ alkyl, optionally substituted $C_{1-12}$ haloalkyl, optionally substituted $C_{3-10}$ cycloalkyl, optionally substituted $C_{6-10}$ aryl, and optionally substituted $C_{7-22}$ arylalkyl;
Ac is —C(O)$CH_3$; and
Gc is —C(O)$CH_2$OH;
provided that at least one of $R^1$, $R^2$, $R^3$, and $R^4$ is other than —OH when $R^5$ is —NHAc or —NHGc.

Compounds of Formula II, and salts thereof, are also provided:

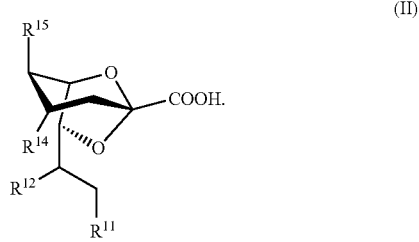

(II)

For compounds of Formula II:
$R^{11}$, $R^{12}$, and $R^{14}$ are independently selected from the group consisting of —NHC(O)$R^a$, —$N_3$, —$NH_2$, —NH$R^a$, —OC(O)$R^a$, —OH, and hydrogen;
$R^{15}$ is selected from the group consisting of —NHAc, —NHGc, —NHC(O)$R^a$, —$N_3$, —$NH_2$, —OC(O)$R^a$, —OH, and hydrogen;
$R^a$ is selected from the group consisting of optionally substituted $C_{1-12}$ alkyl, optionally substituted $C_{1-12}$ haloalkyl, optionally substituted $C_{3-10}$ cycloalkyl, optionally substituted $C_{6-10}$ aryl, and optionally substituted $C_{7-22}$ arylalkyl;

Ac is —C(O)CH$_3$; and

Gc is —C(O)CH$_2$OH;

provided that at least one of $R^{11}$, $R^{12}$, and $R^{14}$ is other than —OH when $R^{15}$ is —NHAc or —NHGc.

Compounds of Formula I and Formula II can be used as sialidase inhibitors, as well as for the study of sialidase activity and for the chemical or chemoenzymatic synthesis of sialosides.

DETAILED DESCRIPTION OF THE INVENTION

I. Introduction

Figure 1:
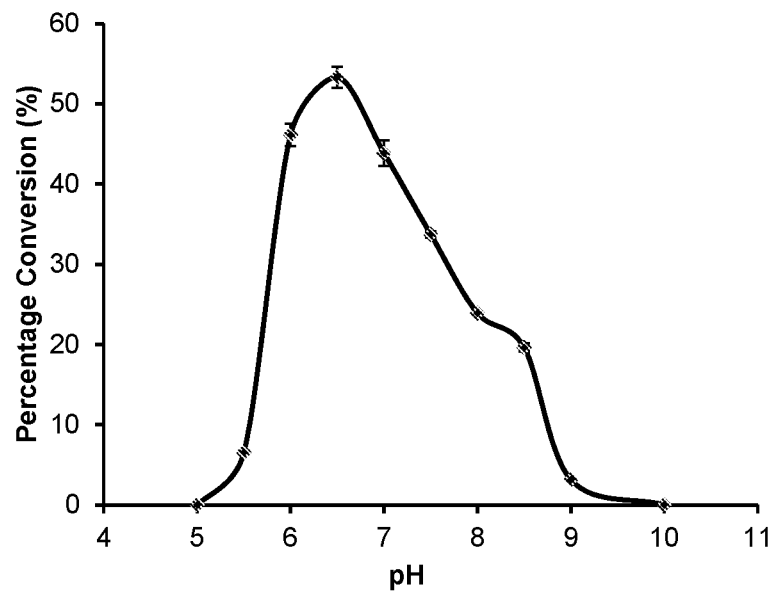
FIG. 1 shows the pH profile of SpNanC using Neu5Acα2-3GalβpNP as the substrate. Buffers used: MES, pH 5.0-6.5; Tris-HCl, pH 7.0-9.0; CAPS, pH 10.0.

Taking advantage of the unique Neu5Ac2en-forming property of *Streptococcus pneumoniae* sialidase SpNanC, an effective one-pot multienzyme (OPME) strategy has been developed to directly access Neu5Ac2en and its C-5, C-9, and C-7 derivatives from N-acetylmannosamine (ManNAc) and derivatives. In this OPME synthesis, sialosides are synthesized from simple carbohydrate precursors using a sialic acid aldolase (e.g., PmAldolase), a CMP-sialic acid synthetase (e.g., NmCSS), and a sialyltransferase (e.g., PmST1_M144D). The sialosides are then utilized by SpNanC to produce 2-deoxy-2,3-dehydro-sialic acids (Sia2ens).

Using the methods described herein, the synthesis of Sia2ens can be completed in one pot starting directly from the corresponding sialic acids or their six-carbon precursors. This method provides a fast and efficient access to a library of Sia2ens. An inexpensive sialyltransferase acceptor such as lactose can be used in a catalytic amount for the production of Sia2en, which allows the economic production of the desired Sia2en inhibitors in an environmentally friendly way.

Alternatively, the reaction can be carried out in two steps. In the first step, a one-pot, multi-enzyme sialylation reaction can be performed to form a sialoside a lactoside tagged with a hydrophobic aglycon to allow easy purification of the product. In the second step, the purified sialoside is used as the substrate for SpNanC-catalyzed reaction for the production of Sia2en. The tagged sialoside and the corresponding tagged lactoside product can be easily separated from Sia2en produced by SpNanC using reverse phase chromatography (e.g., using a C18 cartridge or column).

In addition, the 2,7-anhydro-sialic acid-forming property of *S. pneumoniae* sialidase SpNanB can be leveraged in an effective one-pot multienzyme (OPME) strategy for obtaining direct access to 2,7-anhydro-Sia and its C-5, C-9, and C-7 derivatives from N-acetylmannosamine (ManNAc) and derivatives. Sialosides are synthesized using the multi-enzyme strategy described above, and they can then be utilized by SpNanB to produce 2,7-anhydro-sialic acids (2,7-anhydro-Sias).

A two-step reaction can also be performed to allow easy production and separation of the 2,7-anhydro-Sias. In the first step, a one-pot, multi-enzyme sialylation reaction can be performed to form a sialoside a lactoside tagged with a hydrophobic aglycon to allow easy purification of the product. In the second step, the purified sialoside is used as the substrate for SpNanB-catalyzed reaction for the production of 2,7-anhydro-Sias. The tagged sialoside and the corresponding tagged lactoside product can be easily separated from 2,7-anhydro-Sias produced by SpNanB using reverse phase chromatography (e.g., using a C18 cartridge or column).

II. Definitions

As used herein, the term "sialic acid" refers to N- and O-substituted derivatives of neuraminic acid (i.e., N- and O-substituted derivatives of 5-amino-2-keto-3,5-dideoxy-D-glycero-D-galactononulosonic acid—also referred to as (4S,5R,6R,7S,8R)-5-amino-4,6,7,8,9-pentahydroxy-2-oxo-nonanoic acid). Sialic acids include, but are not limited to, N-acetyl neuraminic acid (Neu5Ac), N-glycolyl neuraminic acid (Neu5Gc), and 2-keto-3-deoxy-D-glycero-D-galactonononic acid (KDN), as well as O-acetyl, O-lactyl, O-methyl, O-sulfate and O-phosphate derivatives.

The terms "2-deoxy-2,3-dehydro-sialic acid" and "Sia2en" refer to sialic acids having a double bond between C2 and C3 of the neuraminic acid core. Sia2ens include, but are not limited to, compounds of Formula I as described herein.

The term "2,7-anhydro-sialic acid" refers to sialic acids wherein the C2 and C7 of the pyranose form of the neuraminic acid core are linked via an oxygen atom. 2,7-Anhydro-sialic acids include, but are not limited to, compounds of Formula II as described herein.

As used herein, the term "glycoside" refers to a saccharide compound having a moiety "—OR" replacing a hydroxyl group of the hemiacetal at the anomeric carbon of the cyclic form of the parent compound, wherein R is another saccharide (e.g., a monosaccharide, oligosaccharide, or polysaccharide) or a non-saccharide moiety (e.g., a lipid, a protein, a peptide, a linker moiety, a label moiety, etc.). A "glycoside acceptor" refers to a glycoside which is used for further elaboration via covalent modification with another saccharide moiety such as a sialic acid.

A "sialoside" refers to a sialic acid pyranose moiety wherein a hydroxyl group of the hemiacetal at the anomeric carbon (i.e., carbon 2) of the cyclic form of the parent compound is replaced with a moiety —OR as described above. Sialosides include, but are not limited to, sialyl lactose, sialyl lactosides, sialyl Tn antigen, and sialyl Lewis$^x$.

As used herein, the term "sialidase" refers to an enzyme that catalyzes the cleavage of a terminal sialic acid from a sialylated substrate (i.e., a sialoside) such as an oligosaccharide, a polysaccharide, a glycosylated protein, a glycosylated lipid, a glycosylated small molecule, or a glycosylated peptide.

As used herein, the term "sialyltransferase" refers to an enzyme that catalyzes the transfer of a sialic acid residue from a sialic acid donor (e.g., a sialic acid nucleotide donor) to an acceptor such as an oligosaccharide, a polysaccharide, a glycosylated protein, a glycosylated lipid, a glycosylated small molecule, or a glycosylated peptide.

As used herein, the term "CMP-sialic acid synthetase" refers to a polypeptide that catalyzes the synthesis of cytidine monophosphate sialic acid (CMP-sialic acid) from cytidine triphosphate (CTP) and sialic acid.

As used herein, the term "sialic acid aldolase" refers to an aldolase that catalyzes a reversible reaction that converts a suitable hexosamine, hexose, pentose, or derivative (such as N-acetyl mannosamine) to sialic acid via reaction with pyruvate.

As used herein, the term "lactose" refers to β-D-galactopyranosyl-(1→4)-D-glucose (i.e., β-lactose) and isomers thereof such as α-lactose.

As used herein, the term "lactoside" refers to refers to a disaccharide derivative wherein a hydroxyl group of the hemiacetal at the anomeric carbon (carbon 1) of glucopyranose in lactose is replaced with a moiety —OR, as described above. In some embodiments, R is a non-sugar structure such as propyl azide, carboxybenzyl (Cbz)-protected propyl amine, fluorenylmethyloxycarbonyl (Fmoc)-protected propyl amine, or the like.

As used herein, the term "pyruvate" refers to the anion of 2-oxopropanoic acid having the formula $CH_3C(O)C(O)O^-$. One of skill in the art will appreciate that pyruvate can be provided in reactions mixtures as the protonated acid or a salt such as sodium pyruvate.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. Unless otherwise specified, "substituted alkyl" groups can be substituted with one or more groups selected from halo, hydroxy, amino, alkylamino, amido, acyl, nitro, cyano, and alkoxy.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbomene, and norbomadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Unless otherwise specified, "substituted cycloalkyl" groups can be substituted with one or more groups selected from halo, hydroxy, amino, alkylamino, amido, acyl, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl.

As used herein, the terms "halo" and "halogen," by themselves or as part of another substituent, refer to a fluorine, chlorine, bromine, or iodine atom.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)$NR_2$, wherein each R group is H or alkyl.

As used herein, the term "nitro" refers to the moiety —$NO_2$.

As used herein, the term "acylating" refers to the conversion of an alcohol group (—OH) to an ester group (—OC(O)R) or to the conversion of an amino group (—$NH_2$) to an amide group (—NHC(O)R), where R is an alkyl group as described below.

III. Methods for Preparing Sialic Acid Products

Some embodiments disclosed herein provide methods which include contacting a sialoside with a *Streptococcus pneumoniae* sialidase to form a sialic acid product such as a 2-deoxy-2,3-dehydro-sialic acid or a 2,7-anhydro-sialic acid.

A number of useful sialic products can be prepared using the methods disclosed herein. Deoxy-2,3-dehydro-sialic acids (Sia2ens), for example, can be used as antimicrobial therapeutics or as materials for the synthesis of other carbohydrates. Examples of Sia2ens include, for example, certain compounds described by Li and Chen (Mol. BioSyst. 2011, 7, 1060-1072); Khedri and Chen (Org. Biomol. Chem. 2012, 10, 6112-6120); Meindl (Monatshefte für Chemie 1969, 100, 1295-1306); Nitabaru (Angew. Chem. Int. Ed. 2012, 51, 1644-1647); Tian (Angew. Chem. Int. Ed. 2014, 53, 13885-13888); Kiefel (Chem. Rev. 2002, 102, 471-490); Laborda (Molecules 2016, 21, 1513); Hemeon (Synthesis 2007, 2007, 1899-1926); Claesson (Acta Chem. Scand. 1982, 36B, 719-720); Albohy (ACS Med. Chem. Lett. 2013, 4, 532-537); Magesh (Bioorg. Med. Chem. Lett. 2008, 18, 532-537); Maring (WO 01/28981); and Von Itzstein (WO 2016/033660).

In some embodiments, the sialic acid product is a 2-deoxy-2,3-dehydro-sialic acid or a derivative thereof. For example, a sialidase can be used to convert a sialoside according to Formula III to a Sia2en as shown in Scheme 1:

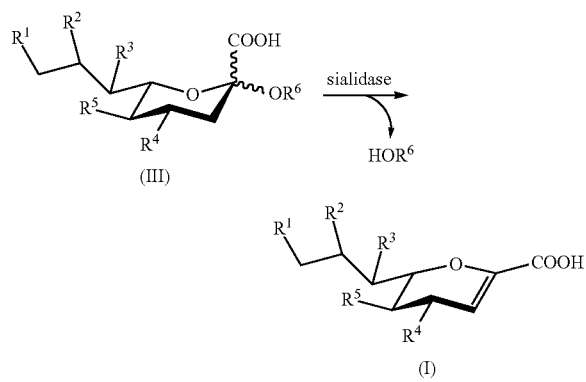

In Scheme 1, $R^1$, $R^2$, $R^3$, and $R^4$ can independently be —NHC(O)$R^a$, —N$_3$, —NH$_2$, —NHR$^a$, —OC(O)$R^a$, —OH, or hydrogen; $R^5$ can be —NHAc, —NHGc, —NHC(O)$R^a$, —N$_3$, —NH$_2$, —OC(O)$R^a$, —OH, or hydrogen (wherein Ac is —C(O)CH$_3$ and Gc is —C(O)CH$_2$OH); and each $R^a$ can independently be optionally substituted C$_{1-12}$ alkyl, optionally substituted C$_{1-12}$ haloalkyl, optionally substituted C$_{3-10}$ cycloalkyl, optionally substituted C$_{6-10}$ aryl, and optionally substituted C$_{7-22}$ arylalkyl. $R^6$ can be a monosaccharide, an oligosaccharide, a polysaccharide, a glycosylated lipid, a glycosylated protein, a glycosylated peptide, a glycosylated small molecule, or a non-saccharide moiety.

In some embodiments, a sialidase can be used to convert a sialoside according to Formula IIIa to a Sia2en according to Formula Ia as shown in Scheme 1A (wherein $R^1$-$R^6$ are defined as for Scheme 1).

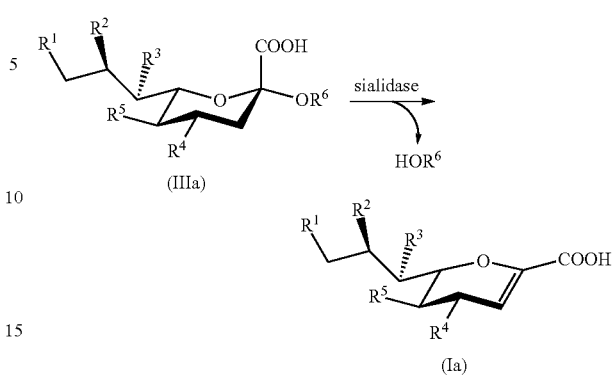

In some embodiments, the *Streptococcus pneumoniae* sialidase used for preparing Sia2ens is SpNanC (NCBI Accession No. WP_024478413.1), comprising the amino acid sequence set forth in SEQ ID NO: 1, or a catalytically active variant thereof.

In some embodiments, an SpNanC variant containing an amino acid sequence having at least about 80% sequence identity to the amino acid sequence set forth in SEQ ID NO:1 is used in the method. The SpNanC variant can have, for example, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO: 1.

Percentage of sequence identity is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

"Identical" and "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 75%, at least 80%, at least 85%, at least 90%, at least 95%, or at least 99% identical over a specified region), when compared and aligned for maximum correspondence over a comparison window, or designated region as measured using one of the following sequence comparison algorithms or by manual alignment and visual inspection. These definitions also refer to the complement of a nucleic acid test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, for example, BLAST and BLAST 2.0 algorithms can be used, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The BLAST algorithms provide a statistical analysis of the similarity between two sequences (see, e.g., Karlin and Altschul, *Proc. Nat'l. Acad. Sci. USA,* 90: 5873-5787 (1993)). One measure of similarity provided by the BLAST algorithm is the smallest sum probability (P(N)), which provides an indication of the probability by which a match between two nucleotide or amino acid sequences would occur by chance.

In some embodiments, the SpNanC is *S. pneumoniae* TIGR4 SpNanC, comprising the amino acid sequence set forth in SEQ ID NO:2, or a catalytically active variant thereof.

In some embodiments, an *S. pneumoniae* TIGR4 SpNanC variant containing an amino acid sequence having at least about 80% sequence identity to the amino acid sequence set forth in SEQ ID NO:2 is used in the method. The *S. pneumoniae* TIGR4 SpNanC variant can have, for example, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO:2.

In some embodiments, the sialic acid product is a 2,7-anhydro-sialic acid or a derivative thereof. For example, a sialidase can be used to convert a sialoside according to Formula IIa to a 2,7-anhydro-sialic acid as shown in Scheme 2:

Scheme 2

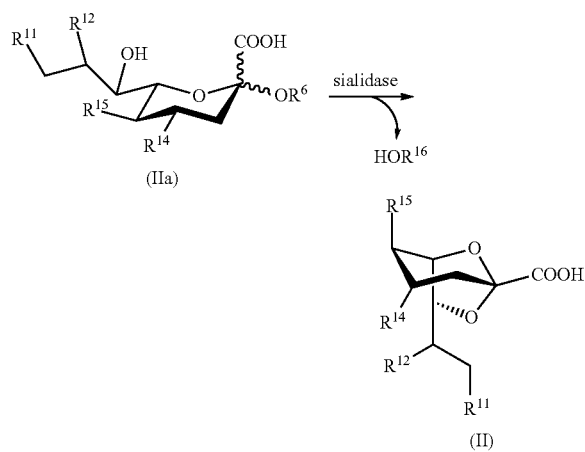

In Scheme 2, $R^{11}$, $R^{12}$, and $R^{14}$ can independently be —NHC(O)$R^a$, —N$_3$, —NH$_2$, —NHR$^a$, —OC(O)R$^a$, —OH, or hydrogen; $R^{15}$ can be —NHAc, —NHGc, —NHC(O)$R^a$, —N$_3$, —NH$_2$, —OC(O)R$^a$, —OH, or hydrogen (wherein Ac is —C(O)CH$_3$ and Gc is —C(O)CH$_2$OH); and each $R^a$ can independently be optionally substituted C$_{1-12}$ alkyl, optionally substituted C$_{1-12}$ haloalkyl, optionally substituted C$_{3-10}$ cycloalkyl, optionally substituted C$_{6-10}$ aryl, and optionally substituted C$_{7-22}$ arylalkyl. $R^{16}$ can be a monosaccharide, an oligosaccharide, a polysaccharide, a glycosylated lipid, a glycosylated protein, a glycosylated peptide, a glycosylated small molecule, or a non-saccharide moiety.

In some embodiments, a sialidase can be used to convert a sialoside according to Formula IVa to a 2,7-anhydro-sialic acid according to Formula IIa as shown in Scheme 2A (wherein $R^{11}$, $R^{12}$, $R^{14}$, $R^{15}$, and $R^{16}$ as defined as for Scheme 2):

Scheme 2A

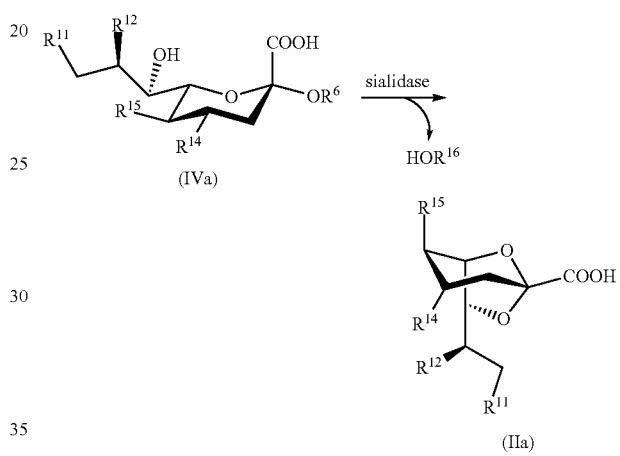

In some embodiments, the *Streptococcus pneumoniae* sialidase used for forming 2,7-anhydro-sialic acids is SpNanB, having the amino acid sequence set forth in SEQ ID NO:3, or a catalytically active variant thereof.

In some embodiments, an SpNanB variant containing an amino acid sequence having at least about 80% sequence identity to the amino acid sequence set forth in SEQ ID NO:3 is used in the method. The SpNanB variant can have, for example, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO:3.

The methods include providing reaction mixtures that contain the *S. pneumoniae* sialidases described herein. The sialidases can be, for example, isolated or otherwise purified prior to addition to the reaction mixture. As used herein, a "purified" enzyme (e.g., an SpNanC or variant thereof, an SpNanB or variant thereof, a sialyltransferase, a CMP-sialic acid synthetase, or a sialic acid aldolase) refers to an enzyme which is provided as a purified protein composition wherein the enzyme constitutes at least about 50% of the total protein in the purified protein composition. For example, the enzyme (e.g., an SpNanC or SpNanB) can constitute about 50%, 60%, 70%, 75%, 80%, 85%, 90%, 95%, or 99% of the total protein in the purified protein composition. In some embodiments, the sialidase in the reaction mixture is provided as a purified protein composition wherein the sialidase constitutes at least about 95% of the total protein in purified protein composition. The amount of the sialidase in a purified protein composition can be determined by any number of known methods including, for example, by polyacrylamide gel electrophoresis (e.g., SDS-PAGE) followed by detection with a staining reagent (e.g., Coomassie Brilliant Blue G-250, a silver nitrate stain, and/or a reagent containing a sialidase antibody). The reaction mixtures can be formed and used in vitro. The sialidases and other enzymes used in the methods can also be secreted by a cell present in the reaction mixture. Alternatively, a sialidase variant or another enzyme can catalyze the reaction within a cell expressing the variant.

Reaction mixtures can contain additional reagents for use in glycosylation techniques. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)), reducing agents (e.g., dithiothreitol (DTT), β-mercaptoethanol (BME), and tris(2-carboxyethyl)phosphine (TCEP)), and labels (e.g., fluorophores, radiolabels, and spin labels). Buffers, cosolvents, salts, detergents/surfactants, chelators, reducing agents, and labels can be used at any suitable concentration, which can be readily determined by one of skill in the art. In general, buffers, cosolvents, salts, detergents/surfactants, chelators, reducing agents, and labels are included in reaction mixtures at concentrations ranging from about 1 µM to about 1 M. For example, a buffer, a cosolvent, a salt, a detergent/surfactant, a chelator, a reducing agent, or a label can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, the reaction mixtures contain a sialoside and a sialoside as described herein, as well as one or more components selected from a buffer, a cosolvent, a salt, a detergent/surfactant, a chelator, a reducing agent, and a label. In some embodiments, the reaction mixtures contain a sialoside and a sialoside as described herein, as well as one or more components selected from a buffer, a cosolvent, a salt, a detergent/surfactant, a chelator, and a reducing agent. In some embodiments, the reaction mixtures consist essentially of a sialoside and a sialidase as described herein, and one or more components selected from a buffer, a cosolvent, a salt, a detergent/surfactant, a chelator, and a reducing agent.

Reactions are conducted under conditions sufficient to convert the sialoside to the sialic acid product (e.g., a 2-deoxy-2,3-dehydro-sialic acid, a 2,7-anhydro-sialic acid, or a derivative thereof). The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours, or about 96 hours, or about 120 hours, or about 144 hours, or about 168 hours. Other reaction conditions may be employed in the methods, depending on the identity of a particular sialoside or sialidase.

A number of sialosides can be used in the methods disclosed herein, including sialosides according to Formula III, Formula IIIa, Formula IV, and Formula IVa as described above. In general, a sialoside will include at least one sialic acid covalently linked to another carbohydrate moiety or a non-carbohydrate moiety. The covalent linkages generally consist of glycosidic linkages (i.e., C—O—C bonds) formed from a hydroxyl group of the hemiacetal at the sialic acid anomeric carbon and a hydroxyl group of an adjacent sugar or an adjacent non-carbohydrate moiety. Linkages can occur, for example, between the carbon-2 of a sialic acid and the carbon-3 of an adjacent sugar (i.e., a 2-3 linkage). The sialic acid can be linked in the sialoside such that the bond at the anomeric carbon is in the α-configuration.

In some embodiments, the sialoside is a compound according to Formula III or Formula IIIa, wherein $R^6$ is a galactoside (e.g., lactose or a lactoside). In some embodiments, $R^6$ is bonded to the compound via a 2-3 linkage (i.e., between carbon-2 of the sialic acid and carbon-3 of the galactose). In some embodiments, the sialoside is a compound according to Formula IV or Formula IVa, wherein $R^{16}$ is a galactoside (e.g., lactose or a lactoside). In some embodiments, $R^{16}$ is bonded to the compound via a 2-3 linkage (i.e., between carbon-2 of the sialic acid and carbon-3 of the galactose).

In some embodiments, $R^6$ or $R^{16}$ is present as a member of an oligosaccharide, a polysaccharide, a glycosylated natural product, a glycopeptide, a glycoprotein, or a glycolipid. Suitable natural products include non-ribosomal glycopeptides (such as bleomycin), glycoalkaloids (such as solanine), ginsenosides (such as sanchinoside C1), aminoglycosides (such as gentamicin, kanamycin, neomycin, and streptomycin), avermectins, and anthracyclines (such as daunorubicin). Suitable glycolipids include glycoglycerolipids (such as monogalactosyldiacylglycerols, digalactosylmonoacylglycerols, and sulfoquinovosyl diacylglycerols), glycosphingolipids (such as lacto-, neolacto-, ganglio-, globo-, and iso-globo-series glycosphingolipids), and glycophosphatidylinositols (e.g., 1-phosphatidyl-L-myo-inositol 2,6-di-O-α-D-mannopyranoside.). Suitable glycoproteins include mucins, immunoglobulins, lectins, and collagens.

In some embodiments, the sialoside is a compound according to Formula V:

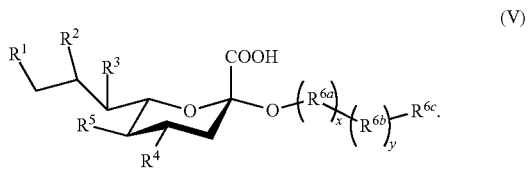

(V)

In compounds according to Formula Ib, $R^{6a}$ is a monosaccharide, disaccharide or oligosaccharide, and subscript x is 0 or 1. $R^{6b}$ is a linker, and subscript y is 0 or 1. In some embodiments, the linker is selected from $C_{1-6}$ alkylene; $C_{1-6}$ alkylene-NH—C(O)—$C_{1-6}$ alkylene; and $C_{1-6}$ alkylene-NH—C(O)—(CH$_2$—(CH$_2$CH$_2$O)$_p$—NH—C(O))$_m$—$C_{1-6}$ alkylene, where subscript m is 0 or 1, and subscript p is an integer from 1 to 6. In some embodiments, subscript y is 1 and $R^{6c}$ is $C_{1-6}$ alkylene (e.g., n-propylene), which is optionally substituted with one or more groups selected from halo, hydroxy, amino, azido (i.e., —$N_3$), alkylamino, amido, acyl, nitro, cyano, and alkoxy. Functional groups in sialosides can be modified protecting groups.

The term "protecting group" refers to a chemical moiety that renders a functional group (e.g., an amino group) unreactive, but is also removable so as to restore the reactive functional group. Examples of protecting groups include, but are not limited to, benzyloxycarbonyl (Z or Cbz); 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other protecting groups are known to those of skill in the art including, for example, those described by Green and Wuts (*Protective Groups in Organic Synthesis*, 4$^{th}$ Ed. 2007, Wiley-Interscience, New York).

In some embodiments, the sialoside is a compound according to Formula Va:

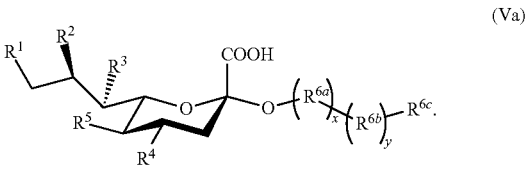

(Va)

Accordingly some embodiments disclosed herein provide methods wherein the sialoside is an α2-3-linked sialoside or a derivative thereof. In some embodiments, the α2-3-linked sialoside is selected from the group consisting of Neu5Acα2-3Lac, Neu5Gcα2-3Lac, Neu5TFAα2-3Lac, Neu5Acα2-3LacbProN$_3$, Neu5Acα2-3LacbProNHCbz, Neu5TFAα2-3LacbProN$_3$, Neu5TFAα2-3LacbProNHCbz, and derivatives thereof.

The sialoside can be prepared prior to forming the sialic acid product, or prepared in situ immediately prior to formation of the sialic acid product. In some embodiments, the methods disclosed herein also include forming a reaction mixture containing an acceptor glycoside, a sialic acid donor, and a sialyltransferase under conditions sufficient to form the sialoside. Sialic acid donors generally include a nucleotide and a sialic acid moiety. Suitable nucleotides include, but are not limited to, adenine, guanine, cytosine, uracil and thymine nucleotides with one, two or three phosphate groups. In some embodiments, the nucleotide can be cytidine monophosphate (CMP). The sialic acid donor can contain a number of sialic acid moieties. In some embodiments, the method includes contacting an acceptor sugar and a sialyltransferase in the presence of a CMP-sialic acid to form the α2-3-linked sialoside. In some embodiments, the acceptor sugar is lactose. In some embodiments, the lactose is β-lactose (i.e., β-D-galactopyranosyl-(1→4)-D-glucose; "Galβ1-4Glc"), or a or β-lactoside (e.g., Galβ1-4GlcβProNHCbz, where Pro is —(CH$_2$)$_3$—).

Any suitable sialyltransferase (also referred to as "ST") can be used in the methods for forming the sialosides disclosed herein. In some embodiments, the sialyltransferase is a beta-galactoside alpha-2,3-sialyltransferases belonging to Glycosyltransferase family 80 (GT80 using CAZy nomenclature), which catalyzes the following conversion: CMP-sialic acid+β-D-galactosyl-R=CMP+α-sialic acid-(2→3)-β-D-galactosyl-R, where the acceptor is GalβOR, where R is H, a monosaccharide, an oligosaccharide, a polysaccharide, a glycopeptide, a glycoprotein, a glycolipid, or a hydroxyl-containing compound.

In some embodiments, the sialyltransferase is selected from the group consisting of PmST1, a PmST1 variant, PmST2, a PmST2 variant, PmST3, a PmST3 variant, and a polysialyltransferase.

In some embodiments, the sialyltransferase is PmST1 (NCBI Accession No. WP_005753497.1) or a catalytically active variant thereof. In some embodiments, the sialyltransferase is PmST1_M144D or a catalytically active variant thereof. In some embodiments, the sialyltransferase comprises the polypeptide sequence set forth in SEQ ID NO:4, or a catalytically active variant thereof.

In some embodiments, the sialyltransferase is PmST2 (UniProtKB Accession No. Q9CNC4) or a catalytically active variant thereof. PmST2 are variants thereof are described in U.S. Pat. No. 9,102,967, which is incorporated herein by reference in its entirety. In some embodiments, the sialyltransferase comprises the polypeptide sequence set forth in SEQ ID NO:5, or a catalytically active variant thereof.

In some embodiments, the sialyltransferase is PmST3 or a catalytically active variant thereof, as described in U.S. Pat. No. 9,783,838, which is incorporated herein by reference in its entirety. In some embodiments, the sialyltransferase is PmST3Δ35 or a catalytically active variant thereof. In some embodiments, the sialyltransferase comprises the polypeptide sequence set forth in SEQ ID NO:6, or a catalytically active variant thereof.

In some embodiments, the sialyltransferase is PmST1_M144D, having the amino acid sequence set forth in SEQ ID NO:4 or a catalytically active variant thereof.

In some embodiments, a PmST1_M144D variant containing an amino acid sequence having at least about 80% sequence identity to the amino acid sequence set forth in SEQ ID NO:4 is used in the method. The PmST1_M144D variant can have, for example, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO:4.

Advantageously, lactose, lactosides, and other acceptors can be used in catalytic amounts for the economic production of the sialic acid products. By "catalytic," it is meant that less than one molar equivalent of the acceptor per molar equivalent of the sialic acid donor is used. For example, reaction mixture may contain an acceptor such as lactose in an amount ranging from about 0.1 mol % to about 50 mol % with respect to the amount of the sialic acid donor. The amount of the acceptor in the reaction mixture can range, for example, from about 1 mol % to about 50 mol %, or from about 5 mol % to about 45 mol %, or from about 10 mol % to about 30 mol %, with respect to the amount of the sialic acid donor. The amount of the acceptor in reaction mixture can be about 5, 10, 15, 20, 25, 30, 35, 40, or 45 mol % with respect to the amount of the sialic acid donor.

A sialic acid donor (e.g., a CMP-sialic acid) can be prepared prior to forming the sialoside, or prepared in situ immediately prior to formation of the sialoside. In some embodiments, the methods also include forming a reaction mixture including a CMP-sialic acid synthetase, cytidine triphosphate, and N-acetylneuraminic acid (Neu5Ac) or a Neu5Ac analog, under conditions suitable to form CMP-Neu5Ac or a CMP-Neu5Ac analog. In some embodiments, the method further includes contacting a sialic acid and a CMP-sialic acid synthetase in the presence of CTP to form the CMP-sialic acid.

Any suitable CMP-sialic acid synthetase (i.e., N-acetylneuraminate cytidylyltransferase, EC 2.7.7.43) can be used in the methods. For example, CMP-sialic acid synthetases from E. coli, C. thermocellum, S. agalactiae, P. multocida, H. ducreyi, or N. meningitidis can be used. In some embodiments, the CMP-sialic acid synthetase is NmCSS (NCBI Accession No. WP_025459740.1) or a catalytically active variant thereof. In some embodiments, the CMP-sialic acid synthetase comprises the polypeptide sequence set forth in SEQ ID NO:7 or a catalytically active variant thereof.

In some embodiments, an NmCSS variant containing an amino acid sequence having at least about 80% sequence identity to the amino acid sequence set forth in SEQ ID NO:7 is used in the method. The NmCSS variant can have, for example, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO:7.

In some embodiments, the CMP-sialic acid synthetase is a purified CMP-sialic acid synthetase as described above with respect to sialidases. Other components (e.g., buffers, cosolvents, salts, detergents/surfactants, chelators, and/or reducing agents, as described above) can be included in the reaction mixture for forming the CMP-Neu5Ac/CMP-Neu5Ac analog. In some embodiments, the step of forming the sialic acid donor and the step of forming the sialylated product are performed in one pot.

In some embodiments, the sialic acid moiety of the sialic acid donor is prepared separately prior to use in the methods. Alternatively, the sialic acid moiety can be prepared in situ immediately prior to use in the methods. In some embodiments, the methods include forming a reaction mixture including a sialic acid aldolase, pyruvic acid or derivatives thereof, and N-acetylmannosamine or derivatives thereof, under conditions suitable to form Neu5Ac or a Neu5Ac analog. In some embodiments, the method further includes contacting a $C_6$-monosaccharide and a sialic acid aldolase in the presence of pyruvate to form to the sialic acid.

Any suitable sialic acid aldolase (i.e., N-acetylneuraminate pyruvate lyase, EC 4.1.3.3) can be used in the methods. For example, sialic acid aldolases from E. coli, L. plantarum, P. multocida, or N. meningitidis can be used. In some embodiments, the sialic acid aldolase is PmAldolase (NCBI Accession No. WP_005723432.1) or a catalytically active variant thereof. In some embodiments, the sialic acid aldolase comprises the polypeptide sequence set forth in SEQ ID NO:8, or a catalytically active variant thereof.

In some embodiments, a PmAldolase variant containing an amino acid sequence having at least about 80% sequence identity to the amino acid sequence set forth in SEQ ID NO:8 is used in the method. The PmAldolase variant can have, for example, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO:8.

In some embodiments, the sialic acid aldolase is a purified sialic acid aldolase as described above with respect to sialidases. Other components (e.g., buffers, cosolvents, salts, detergents/surfactants, chelators, and/or reducing agents, as described above) can be included in the reaction mixture for forming the Neu5Ac/Neu5Ac analog. In some embodiments, the step of forming the sialic acid moiety, the step of forming the sialic acid donor, and the step of forming the sialylated product are performed in one pot.

The methods disclosed herein can further include one or more chemical transformations in addition to the enzymatic steps described above. In certain instances, for example, one or more of $R^1$, $R^2$, $R^3$, and $R^4$ in a Sia2en according to Formula I may be an azido group —$N_3$, which can be reduced via hydrogenolysis with Pd/C or another suitable catalyst to provide an amino group —$NH_2$. Amino groups and/or hydroxyl group in Sia2en products can be acylated to provide the corresponding esters and amides. As a non-limiting example, an amino group $R^1$ in a compound according to Formula I can be acylated to provide an amide having the formula —NHC(O)$R^a$, wherein $R^a$ is $C_{1-12}$ alkyl, $C_{1-12}$ haloalkyl, $C_{3-10}$ cycloalkyl, $C_{6-10}$ aryl, or $C_{7-22}$ arylalkyl. Esters and amides can be optionally substituted with one or more independently-selected substituents such as halo, hydroxy, amino, alkylamino, amido, acyl, nitro, cyano, and alkoxy.

Acylation can be conducted with a suitable carboxylic acid $R^a$COOH or a reactive carboxylic derivative such as an acid chloride or an activated ester (e.g., an N-hydroxysuccinimidyl ester or a pentafluorophenyl ester). The carboxylic acid or carboxylic acid derivative can be used with a coupling agent such as a carbodiimide (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), N-t-butyl-N-methylcarbodiimide (BMC), N-t-butyl-N-ethylcarbodiimide (BEC), 1,3-bis(2,2-dimethyl-1,3-dioxolan-4-ylmethyl)carbodiimide (BDDC), etc.), a phosphonium salt (HOBt, PyBOP, HOAt, etc.), or an aminium/uronium salt (e.g., tetramethyl aminium salts, bispyrrolidino aminium salts, bispiperidino aminium salts, imidazolium uronium salts, pyrimidinium uronium salts, uronium salts derived from N,N,N'-trimethyl-N'-phenylurea, morpholino-based aminium/uronium coupling reagents, antimoniate uronium salts, etc.). Coupling agents such as carbodiimides can be used in conjunction with nucleophilic catalysts such as 4-(N,N-dimethylamino)pyridine and the like to promote formation of the desired ester or amide.

Amino groups can also be modified via reductive amination. As used herein, the term "reductive amination conditions" refers to conditions suitable for converting an amine —$NH_2$ to a substituted amine —$NHCH(R^b)_2$, wherein one $R^b$ is $C_{1-12}$ alkyl, $C_{1-12}$ haloalkyl, $C_{3-10}$ cycloalkyl, $C_{6-10}$ aryl, or $C_{7-22}$ arylalkyl and the other $R^b$ is hydrogen, $C_{1-12}$ alkyl, $C_{1-12}$ haloalkyl, $C_{3-10}$ cycloalkyl, $C_{6-10}$ aryl, or $C_{7-22}$ arylalkyl. Reductive amination can be conducted with a suitable aldehyde or ketone $R^bC(O)R^b$ and a reducing agent such as sodium borohydride, sodium cyanoborohydride, or the like.

IV. 2-Deoxy-2,3-dehydro-sialic acids and 2,7-anhydro-sialic acids

Some embodiments disclosed herein provide a compound according to Formula I:

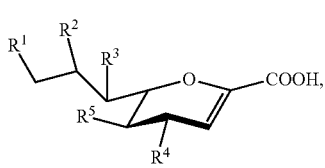

(I)

or a salt thereof, wherein:
$R^1$, $R^2$, $R^3$, and $R^4$ are independently selected from the group consisting of —$NHC(O)R^a$, —$N_3$, —$NH_2$, —$NHR^a$, —$OC(O)R^a$, —OH, and hydrogen;
$R^5$ is selected from the group consisting of —NHAc, —NHGc, —$NHC(O)R^a$, —$N_3$, —$NH_2$, —$OC(O)R^a$, —OH, and hydrogen;
each $R^a$ is independently selected from the group consisting of optionally substituted $C_{1-12}$ alkyl, optionally substituted $C_{1-12}$ haloalkyl, optionally substituted $C_{3-10}$ cycloalkyl, optionally substituted $C_{6-10}$ aryl, and optionally substituted $C_{7-22}$ arylalkyl;
Ac is —$C(O)CH_3$; and
Gc is —$C(O)CH_2OH$.

In general, at least one of $R^1$, $R^2$, $R^3$, and $R^4$ is other than —OH when $R^5$ is —NHAc or —NHGc.

In some embodiments, the compound has a structure according to Formula Ia:

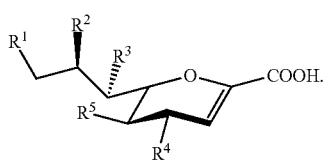

(Ia)

In some embodiments, $R^1$, $R^2$, $R^3$, and $R^4$ are independently selected from the group consisting of —$N_3$, —$NH_2$, —$NHC(O)R^a$, —$NHR^a$, and —OH in compounds of Formula I or Formula Ia. In some such embodiments, $R^5$ is selected from the group consisting of —NHAc, —NHGc, —$NHC(O)CF_3$ (i.e., —NHTFA), —OH, and —OAc. In some embodiments, $R^1$, $R^2$, $R^3$, and $R^4$ are independently selected from the group consisting of —$N_3$ and —OH, and $R^5$ is —NHAc, —NHGc, or —NHTFA. In some embodiments, $R^1$, $R^2$, $R^3$, and $R^4$ are independently selected from the group consisting of —$NHC(O)R^a$ (e.g., —NHAc) and —OH, and $R^5$ is —NHAc, —NHGc, or —NHTFA.

In some embodiments, at least one of $R^1$, $R^2$, $R^3$, and $R^4$ is independently —$N_3$, —$NH_2$, —$NHC(O)R^a$, or —$NHR^a$ in compounds of Formula I or Formula Ia. In some embodiments, at least two of $R^1$, $R^2$, $R^3$, and $R^4$ are independently —$N_3$, —$NH_2$, —$NHC(O)R^a$, or —$NHR^a$. In some embodiments, at least three of $R^1$, $R^2$, $R^3$, and $R^4$ are independently —$N_3$, —$NH_2$, —$NHC(O)R^a$, or —$NHR^a$. In some embodiments, remaining $R^1$, $R^2$, $R^3$, and $R^4$ groups are independently selected from —OH and —$OC(O)R^a$. In some such embodiments, the remaining $R^1$, $R^2$, $R^3$, and $R^4$ groups are —OH. In some embodiments, $R^1$, $R^2$, $R^3$, and $R^4$ are independently —$N_3$, —$NH_2$, —$NHC(O)R^a$, or —$NHR^a$.

In some embodiments, $R^5$ is —NHAc or —NHGc and at least one of $R^1$, $R^2$, $R^3$, and $R^4$ is independently —$N_3$, —$NH_2$, or —$NHC(O)R^a$ in compounds of Formula I or Formula Ia. In some embodiments, $R^5$ is —NHAc or —NHGc and at least two of $R^1$, $R^2$, $R^3$, and $R^4$ are independently —$N_3$, —$NH_2$, or —$NHC(O)R^a$. In some embodiments, $R^5$ is —NHAc or —NHGc and at least three of $R^1$, $R^2$, $R^3$, and $R^4$ are independently —$N_3$, —$NH_2$, or —$NHC(O)R^a$. In some embodiments, remaining $R^1$, $R^2$, $R^3$, and $R^4$ groups are independently selected from —OH and —$OC(O)R^a$. In some such embodiments, the remaining $R^1$, $R^2$, $R^3$, and $R^4$ groups are —OH. In some embodiments, $R^5$ is —NHAc or —NHGc and $R^1$, $R^2$, $R^3$, and $R^4$ are independently —$N_3$, —$NH_2$, or —$NHC(O)R^a$.

In some embodiments, $R^1$ is —$NHC(O)R^a$ or —$NHR^a$ in compounds of Formula I or Formula Ia. In some embodiments, $R^a$ is $C_{1-12}$ alkyl or $C_{3-10}$ cycloalkyl. $R^a$ can be, for example, methyl, ethyl, n-propyl, isopropyl, n-butyl, isobutyl, sec-butyl, tert-butyl, n-pentyl, branched pentyl, n-hexyl, branched hexyl, n-heptyl, branched heptyl, n-octyl, branched octyl, n-nonyl, branched nonyl, n-decyl, branched n-decyl, n-undecyl, branched undecyl, n-dodecyl, branched dodecyl, cyclopropyl, cyclobutyl, cyclopentyl, cyclohexyl, cycloheptyl, or cyclooctyl.

In some embodiments, $R^3$ is selected from the group consisting of —OH and hydrogen.

In some embodiments, $R^5$ is selected from the group consisting of —NHAc, —NHGc, and —$NHC(O)R^a$. In some such embodiments, $R^a$ is $C_{3-10}$ cycloalkyl. When $R^5$ is —$NHC(O)R^a$, for example, $R^a$ can be $C_{3-10}$ cycloalkyl or $C_{7-22}$ arylalkyl. $R^a$ can be, for example, cyclopropyl, cyclobutyl, cyclopentyl, cyclohexyl, cycloheptyl, or cyclooctyl. $R^a$ can be benzyl (i.e., phenylmethyl), (2-phenyl)ethyl, (3-phenyl)propyl, (2-phenyl)propyl, (4-phenyl)butyl, or the like.

In some embodiments, the compound is selected from the group consisting of:

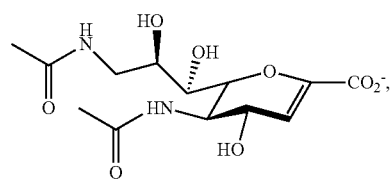

-continued

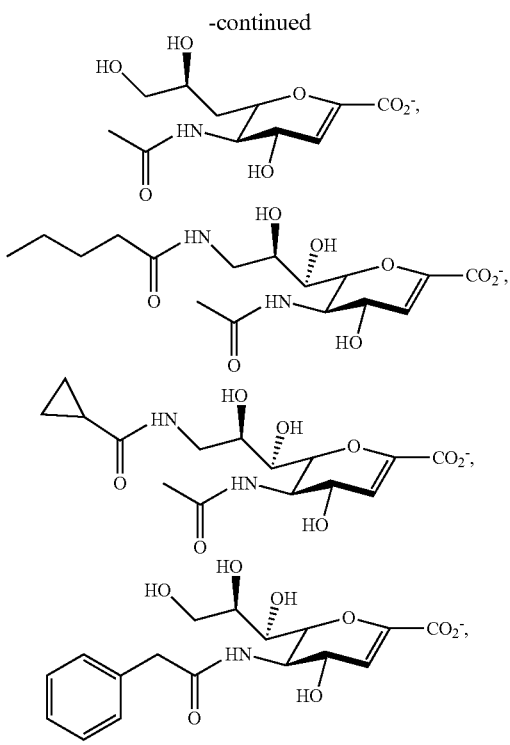

and salts thereof.

Some embodiments disclosed herein provide a compound according to Formula II:

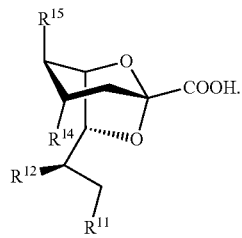

(II)

or a salt thereof, wherein:

$R^{11}$, $R^{12}$, and $R^{14}$ are independently selected from the group consisting of —NHC(O)$R^a$, —$N_3$, —$NH_2$, —NH$R^a$, —OC(O)$R^a$, —OH, and hydrogen;

$R^{15}$ is selected from the group consisting of —NHAc, —NHGc, —NHC(O)$R^a$, —$N_3$, —$NH_2$, —OC(O)$R^a$, —OH, and hydrogen;

$R^a$ is selected from the group consisting of optionally substituted $C_{1-12}$ alkyl, optionally substituted $C_{1-12}$ haloalkyl, optionally substituted $C_{3-10}$ cycloalkyl, optionally substituted $C_{6-10}$ aryl, and optionally substituted $C_{7-22}$ arylalkyl;

Ac is —C(O)CH$_3$; and

Gc is —C(O)CH$_2$OH.

In general, at least one of $R^{11}$, $R^{12}$, and $R^{14}$ is other than —OH when $R^{15}$ is —NHAc or —NHGc.

In some embodiments, the compound has a structure according to Formula IIa:

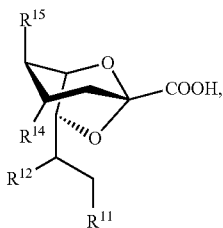

(IIa)

In some embodiments, $R^{11}$, $R^{12}$, and $R^{14}$ are independently selected from the group consisting of —$N_3$, —$NH_2$, —NHC(O)$R^a$, —NH$R^a$, and —OH in compounds of Formula II or Formula IIa. In some such embodiments, $R^{15}$ is selected from the group consisting of —NHC(O)$R^a$, —NHAc, —NHGc, —NHTFA, —OH, and —OAc. In some embodiments, $R^{11}$, $R^{12}$ and $R^{14}$ are independently selected from the group consisting of —$N_3$ and —OH, and $R^{15}$ is —NHC(O)$R^a$, —NHAc, —NHGc, or —NHTFA. In some embodiments, $R^{11}$, $R^{12}$, and $R^{14}$ are independently selected from the group consisting of —NHC(O)$R^a$ (e.g., —NHAc) and —OH, and $R^{15}$ is —NHAc, —NHGc, or —NHTFA.

In some embodiments, at least one of $R^{11}$, $R^{12}$, and $R^{14}$ is independently —$N_3$, —$NH_2$, —NHC(O)$R^a$, or —NH$R^a$ in compounds of Formula II or Formula IIa. In some embodiments, at least two of $R^{11}$, $R^{12}$, and $R^{14}$ are independently —$N_3$, —$NH_2$, —NHC(O)$R^a$, or —NH$R^a$. In some embodiments, remaining $R^{11}$, $R^{12}$, and $R^{14}$ groups are independently selected from —OH and —OC(O)$R^a$. In some such embodiments, the remaining $R^{11}$, $R^{12}$, and $R^{14}$ groups are —OH. In some embodiments, $R^{11}$, $R^{12}$, and $R^{14}$ are independently —$N_3$, —$NH_2$, —NHC(O)$R^a$, or —NH$R^a$.

In some embodiments, $R^{15}$ is —NHC(O)$R^a$, —NHAc, or —NHGc, and at least one of $R^{11}$, $R^{12}$, and $R^{14}$ is independently —$N_3$, —$NH_2$, or —NHC(O)$R^a$ in compounds of Formula II or Formula IIa. In some embodiments, $R^{15}$ is —NHC(O)$R^a$, —NHAc, or —NHGc, and at least two of $R^{11}$, $R^{12}$, and $R^{14}$ are independently —$N_3$, —$NH_2$, or —NHC(O)$R^a$. In some embodiments, remaining $R^{11}$, $R^{12}$, and $R^{14}$ groups are independently selected from —OH and —OC(O)$R^a$. In some such embodiments, the remaining $R^{11}$, $R^{12}$, and $R^{14}$ groups are —OH. In some embodiments, $R^{15}$ is —NHC(O)$R^a$, —NHAc, or —NHGc, and $R^{11}$, $R^{12}$, and $R^{14}$ are independently —$N_3$, —$NH_2$, or —NHC(O)$R^a$.

In some embodiments, $R^{15}$ is selected from the group consisting of —NHAc, —NHGc, and —NHC(O)$R^a$ in compounds of Formula II or Formula IIa. In some such embodiments, $R^a$ is selected from the group consisting of optionally substituted $C_{1-12}$ alkyl, optionally substituted $C_{1-12}$ haloalkyl, and optionally substituted $C_{3-10}$ cycloalkyl. $R^a$ can be, for example, methyl, ethyl, n-propyl, isopropyl, n-butyl, isobutyl, sec-butyl, tert-butyl, n-pentyl, branched pentyl, n-hexyl, branched hexyl, n-heptyl, branched heptyl, n-octyl, branched octyl, n-nonyl, branched nonyl, n-decyl, branched n-decyl, n-undecyl, branched undecyl, n-dodecyl, or branched dodecyl. $R^a$ can be chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, or the like. $R^a$ can be cyclopropyl, cyclobutyl, cyclopentyl, cyclohexyl, cycloheptyl, or cyclooctyl.

In some embodiments, the compound is selected from the group consisting of

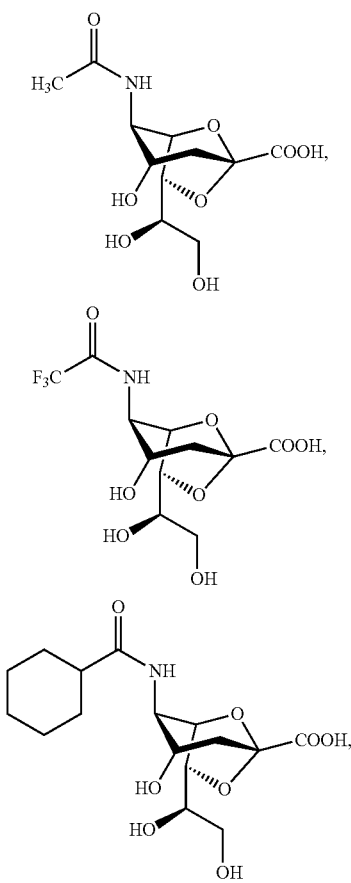

and salts thereof.

In some embodiments, the compound is selected from the group consisting of

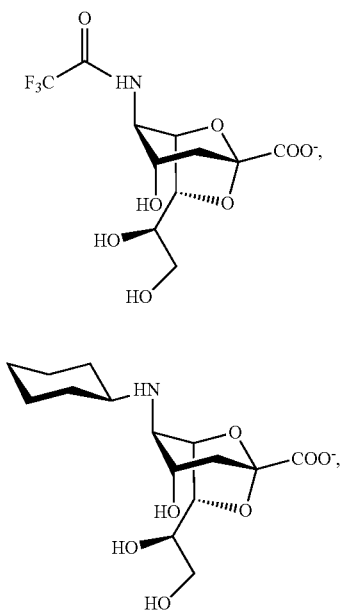

and salts thereof.

V. Methods and Compositions for Sialidase Inhibition and Disease Treatment

In some embodiments, methods for inhibiting sialidases are provided. The methods include contacting the sialidase with an effective amount of a 2-deoxy-2,3-dehydro-sialic acid or a 2,7-anhydro-sialic acid. In certain embodiments, the sialidase is a microbial sialidase or a viral sialidase. Organisms that contain sialidases include bacteria (including, but not limited to, *Vibrio cholerae, Clostridium perfringens, Streptococcus pneumoniae*, and *Arthrobacter sialophilus*) and viruses (including, but not limited to, orthomyxoviruses or paramyxoviruses such as influenza virus A and B, parainfluenza virus, mumps virus, Newcastle disease virus, fowl plague virus, and sendai virus). In some embodiments, the sialidase is SpNanA (NCBI Accession No. WP_010976603.1), SpNanB (NCBI Accession No. NP_359124.1), SpNanC (NCBI Accession No. WP_024478413.1), AuSialidase (NCBI Accession No. WP_062095054.1), CpNanI (NCBI Accession No. WP_011590331.1), CpNanH (UniProtKB Accession No. P10481), VcSialidase (NCBI Accession No. WP_001889713.1), BiNanH2 (NCBI Accession No. WP_012578573.1), hNEU2 (GenBank Accession No. CAB41449.1), hNEU3 (GenBank Accession No. AAI36398.1), or variants thereof containing one or more amino acid substitutions, deletions, and/or other peptide sequence variations. Variants may contain, for example, 1-2 amino acid substitutions or deletions, or 1-4 amino acid substitutions or deletions, or 1-10 amino acid substitutions or deletions, or 1-25 amino acid substitutions or deletions.

Inhibiting the sialidase generally includes contacting the sialidase with an amount of the compound sufficient to reduce the activity of the sialidase as compared to the sialidase activity in the absence of the compound. For example, contacting the sialidase with the sialidase inhibitor can result in from about 1% to about 99% sialidase inhibition (i.e., the activity of the inhibited sialidase ranges from 99% to 1% of the sialidase activity in the absence of the compound). The level of sialidase inhibition can range from about 1% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90%, or from about 90% to about 99%. The level of sialidase inhibition can range from about 5% to about 95%, or from about 10% to about 90%, or from about 20% to about 80%, or from about 30% to about 70%, or from about 40% to about 60%. In some embodiments, contacting the sialidase with a 2-deoxy-2,3-dehydro-sialic acid or a 2,7-anhydro-sialic acid will result in essentially complete (i.e., 100%) sialidase inhibition.

Aberrant sialylation is associated with cancer development as well as with sialic acid storage disease, which can lead to neurological complications. Inhibition of human sialidase NEU3 (hNEU3), in particular, can induce apoptosis in human breast cancer cells and colon cancer cells, which could be leveraged to prevent cancer progression. The diverse roles of sialidases in bacterial and viral pathogens are implicated in invasion, immunosuppression, and virulence. Degradation of human sialic acids by pathogen sialidases contributes to the severity of infectious diseases such as influenza, pneumonia, periodontitis, and bacterial vaginosis. The methods described herein can therefore be employed for the production of sialidase inhibitors for use in the treatment of cancer and infectious diseases, among other conditions.

Provided in some embodiments is a method for treating cancer which includes administering an effective amount of a 2-deoxy-2,3-dehydro-sialic acid (e.g., a compound of Formula I as described herein) or a 2,7-anhydro-sialic acid (e.g., a compound of Formula II) to a subject in need thereof. In some embodiments, there is provided a method for treating a viral infection or a bacterial infection which includes administering an effective amount of a 2-deoxy-2, 3-dehydro-sialic acid (e.g., a compound of Formula I as described herein) or a 2,7-anhydro-sialic acid (e.g., a compound of Formula II) to a subject in need thereof.

Sialidase inhibitors as described herein can be administered at any suitable dose in the methods for disease treatment. In general, a sialidase inhibitor is administered at a dose ranging from about 0.1 milligrams to about 1000 milligrams per kilogram of a subject's body weight (i.e., about 0.1-1000 mg/kg). The dose of sialidase inhibitor can be, for example, about 0.1-1000 mg/kg, or about 1-500 mg/kg, or about 25-250 mg/kg, or about 50-100 mg/kg. The dose of sialidase inhibitor can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the seizure disorder.

Sialidase inhibitors can be administered for periods of time which will vary depending upon the nature of the particular disorder, its severity, and the overall condition of the subject to whom the sialidase inhibitor is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the disorder. The dosage of the sialidase inhibitor can either be increased in the event the subject does not respond significantly to a particular dosage level, or the dose can be decreased if an alleviation of the symptoms of the disorder is observed, or if the disorder has been remedied, or if unacceptable side effects are seen with a particular dosage.

A therapeutically effective amount of a sialidase inhibitor can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 144, 168, 192, 216, or 240 hours (i.e., 3, 4, 5, 6, 7, 8, 9, or 10 days). In certain embodiments, administration of one or more sialidase inhibitors is conducted in periods ranging from several months to several years.

Also provided are pharmaceutical compositions for the administration of sialidase inhibitors, including 2-deoxy-2, 3-dehydro-sialic acids and 2,7-anhydro-sialic acids as described herein. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Aqueous suspensions contain the active materials in admixture with excipients including, but not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, *arachis* oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing the sialidase inhibitors described herein can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

The sialidase inhibitors described herein can also be administered topically as a solution, ointment, cream, gel, suspension, mouth washes, eye-drops, and the like. Still further, transdermal delivery of the sialidase inhibitors can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In some embodiments, an sialidase inhibitor described herein is administered via intraperitoneal injection. In some embodiments, the sialidase inhibitor is administered orally. In some embodiments, the sialidase inhibitor is administered intravenously.

Sialidase inhibitors can be administered alone or in combination with one or more additional therapeutically active agents including, but not limited to, additional sialidase inhibitors (e.g., oseltamivir, zanamivir, peramivir, and the like), viral replication inhibitors (e.g., rimantadine and the like), macrolide antibiotics (e.g., erythromycin and the like), cephalosporin antibiotics (e.g., cefuroxime, ceflacor and the like), and fluoroquinolone antibiotics (e.g., ciprofloxacin, moxifloxacin, and the like). Sialidase inhibitors can also be administered in combination with cytotoxic/anti-cancer agents including, but not limited to, angiogenesis inhibitors (e.g., bevacizumab, ranibizumab, and the like), anthracyclines (e.g., doxorubicin, daunorubicin, and the like), platins (e.g., cisplatin, oxaliplatin, carboplatin, and the like), antimetabolites (e.g., 5-fluorouracil, methotrexate, and the like), kinase inhibitors (e.g., erlotinib, gefitinib, and the like), nucleoside analogs (e.g., gemcitabine, cytarabine, and the like), and taxanes (e.g., paclitaxel, docetaxel, and the like).

VI. Examples

Example 1. Methods for the Preparation of Sia2ens

*E. coli* electrocompetent DH5α and chemically competent BL21 (DE3) cells were from Invitrogen (Carlsbad, Calif.). Herculase II Fusion DNA Polymerase was from Agilent Technologies (Santa Clara, Calif.). T4 DNA ligase and 1 kb DNA ladder were from Promega (Madison, Wis.). EcoRI and HindIII restriction enzymes and vector plasmid pMAL-c4X were from New England BioLabs (Beverly, Mass.). GeneJET PCR Purification Kit and GeneJET Plasmid Miniprep Kit were from Thermo Fisher Scientific (Waltham, Mass.). $Ni^{2+}$-NTA agarose (nickel-nitrilotriaceticacid agarose) was from 5 PRIME (Gaithersburg, Md.). Bicinchoninic acid (BCA) protein assay kit was from Pierce Biotechnology Inc. (Rockford, Ill.). Recombinant sialidases were expressed and purified as reported previously for human cytosolic sialidase hNEU2, as well as bacterial sialidases from *Streptococcus pneumoniae* (SpNanA, SpNanB, and SpNanC), *Pasteurella multocida* (PmST1), *Bifidobacterium infantis* (BiNanH2). Commercially available bacterial sialidases used included those from *Arthrobacter ureafaciens* (Prozyme), *Clostridium perfringens* CpNanI (Sigma-Aldrich) and CpNanH (Prozyme), and *Vibrio cholerae* (Prozyme). *Aspergillus oryzae* β-galactosidase was purchased from Sigma-Aldrich. *Pasteurella multocida* sialic acid aldolase (PmNanA), *Neisseria meningitidis* CMP-sialic acid synthetase (NmCSS), and *Pasteurella multocida* sialyltransferase 1 M144D mutant (PmST1_M144D) were expressed and purified as described previously. N-Acetylmannosamine (ManNAc) derivatives N-glycolylmannosamine (ManNGc, 2), 6-azido-6-deoxy-N-acetylmannosamine (ManNAc6N$_3$, 3), 6-acetamido-6-deoxy-N-acetylmannosamine (ManNAc6NAc, 4), 4-deoxy-N-acetylmannosamine (ManNAc4deoxy, 5) used for Sia2en synthesis as well as Siaα2-3GalβpNP used for substrate specificity studies were synthesized as described previously.

DNA sequencing was performed by Genewiz (South Plainfield, N.J.). Nuclear Magnetic Resonance (NMR) spectra were recorded in the NMR facility of the University of California, Davis on a Bruker Avance-400 NMR spectrometer (400 MHz for $^1$H, 100 MHz for $^{13}$C). Chemical shifts are reported in parts per million (ppm) on the δ scale. High resolution electrospray ionization (ESI) mass spectra were obtained using a Thermo Electron LTQ-Orbitrap Hybrid MS at the Mass Spectrometry Facility at the University of California, Davis. Column chromatography was performed using RediSep Rf silica columns or an ODS-SM (C18) column (51 g, 50 μm, 120 Å, Yamazen) on the CombiFlash® Rf 200i system. Thin layer chromatography (TLC) was performed on silica gel plates (Sorbent Technologies) using anisaldehyde sugar stain for detection. Gel filtration chromatography was performed with a column (100 cm×2.5 cm) packed with Bio-Gel P-2 Fine resins (Bio-Rad). All reagents were at least of reagent grade and were used as supplied without further purification unless indicated.

Cloning.

SpNanC was cloned as a N-maltose binding protein (MBP)-fused and C-His$_6$-tagged recombinant protein in pMAL-c4X vector using genomic DNA of *Streptococcus pneumoniae* TIGR4 (ATCC #BAA-334D-5) as the template for polymerase chain reactions (PCR). The primers used were: forward primer 5'-GATC GAATTCATGAGAAAAAAAATATT AAACAATATG-3' (SEQ ID NO: 9) (EcoRI restriction site is underlined) and reverse primer 5'-ACGC AAGCTTTTAGTGGTGGTGGTGGTGGTGATTC-TTTTTCAGATCTTC-3' (SEQ ID NO: 10) (HindIII restriction site is underlined and the sequence that encodes the hexahistidine tag is italicized). Δ26SpNanC-His$_6$ (abbreviated as SpNanC) was cloned as a C-His$_6$-tagged recombinant protein in pET22b(+) vector with N-terminal 26 amino acids truncation using genomic DNA of Streptococcus pneumoniae TIGR4 (ATCC #BAA-334D-5) as the template for polymerase chain reactions (PCR). The primers used were: forward primer 5'-GATC GAATTCGGCTCAGGAGACTGAAACTT-3' (SEQ ID NO: 11) (EcoRI restriction site is underlined) and reverse primer 5'-ACGC CTCGAGATTCTTTTTCAGATCTTCAATC-3' (SEQ ID NO: 12) (XhoI restriction site is underlined).

PCR was performed in a 50 μL reaction mixture containing S. pneumonia TIGR4 genomic DNA (10 ng), forward and reverse primers (0.25 μM each), 5× Herculase reaction buffer (10 μL), dNTP mixture (0.4 mM), and Herculase II fusion DNA polymerase (1 μL). The PCR procedure included an initial cycle of 4 min at 95° C., followed by 35 cycles of 45 s at 95° C., 45 s at 52° C., and 2 min at 72° C. For the final extension, the reaction was held at 72° C. for 10 min. For MBP-SpNanC-His$_6$, the resulting PCR product was purified and digested with EcoRI and HindIII restriction enzymes. The purified and digested PCR product was ligated with pre-digested pMAL-c4X vector and transformed into electrocompetent E. coli DH5a cells. For Δ26SpNanC-His$_6$ (abbreviated as SpNanC), the resulting PCR product was purified and digested with EcoRI and XhoI restriction enzymes. The purified and digested PCR product was ligated with pre-digested pET22b(+) vector and transformed into electrocompetent E. coli DH5α cells. Selected clones were grown for minipreps and characterization by restriction mapping. DNA sequences were confirmed by DNA sequencing performed by Genewiz (South Plainfield, N.J.).

Expression.

Positive plasmids were selected and transformed into E. coli BL21 (DE3) chemical competent cells. The plasmid-bearing E. coli strains were cultured in LB-rich medium (10 g L$^{-1}$ tryptone, 5 g L$^{-1}$ yeast extract and 10 g L$^{-1}$ NaCl) supplemented with ampicillin (100 μg mL$^{-1}$). Expression of the target protein was achieved by inducing the E. coli culture with 0.5 mM of isopropyl-1-thio-β-D-galactopyranoside (IPTG) when OD$_{600\,nm}$ reached 0.8-1.0 followed by incubating at 20° C. for 20 h with shaking at 190 rpm in a C25KC incubator shaker (New Brunswick Scientific, Edison, N.J.).

Purification.

His$_6$-tagged target proteins were purified from cell lysate. To obtain the cell lysate, cell pellet harvested by centrifugation at 4000 rpm for 50 min was resuspended (25 mL L$^{-1}$ cell culture) in lysis buffer (100 mM Tris-HCl pH 8.0 with 0.1% Triton X-100). Sonication protocol was 3 s (sonication)/3 s (rest) for a total of 4 min on ice. Lysed cells were centrifuged at 8,000 rpm for 50 min and the supernatant was collected as the supernatant. Purification of His$_6$-tagged proteins from the lysate was achieved using a Ni$^{2+}$-resin column. The column was pre-equilibrated with 10 column volumes of binding buffer (5 mM imidazole, 0.5 M NaCl, 50 mM Tris-HCl pH 7.5) before the lysate was loaded. After washing with 10 column volumes of binding buffer, the protein was eluted with an elution buffer (200 mM imidazole, 0.1 M NaCl, 50 mM Tris-HCl pH 7.5). Fractions containing the purified enzymes were combined and dialyzed against dialysis buffer (20 mM Tris-HCl pH 7.5 with 10% glycerol) and stored at −80° C.

Quantification of Purified Protein.

Protein concentration was determined in a 96-well plate using a Bicinchoninic Acid (BCA) Protein Assay Kit (Pierce Biotechnology, Rockford, Ill.) with bovine serum albumin as a protein standard. The absorbance of each sample was measured at 562 nm by a BioTek Synergy™ HT Multi-Mode Microplate Reader.

Sodium dodecylsulfate-polyacrylamide gel electrophoresis (SDS-PAGE). SDS-PAGE was performed in a 10% Tris-glycine gel using a Bio-Rad Mini-protein III cell gel electrophoresis unit (Bio-Rad, Hercules, Calif.) at DC=150 V. Bio-Rad Precision Plus Protein Standards (10-250 kDa) were used as molecular weight standards. Gels were stained with Coomassie Blue R-250.

pH Profile by Capillary Electrophoresis (CE) Assays.

Enzymatic assays were performed in a 10 μL reaction mixture containing a buffer (100 mM) with a pH in the range of 5.0-11.0, Neu5Acα2-3GalβpNP (2 mM) and SpNanC (10 ng). Buffers used were: MES, pH 5.0-6.5; Tris-HCl, pH 7.0-9.0; N-cyclohexyl-3-aminopropanesulfonic acid (CAPS), pH 10.0. Reactions were allowed to proceed for 30 min at 37° C. and were stopped by adding 10 μL of cold ethanol to each reaction mixture. Samples were centrifuged and the supernatants were analyzed by a P/ACETM Capillary Electrophoresis (CE) system equipped with a Photodiode Array (PDA) detector (Beckman Coulter Inc., Fullerton, Calif.). CE conditions were as follows: 75 μm i.d. capillary, 25 KV/80 μÅ, 5 s vacuum injections, monitored at 300 nm, the running buffer used was sodium tetraborate (25 mM, pH 11.0).

Effects of MgCl$_2$, Ethylenediaminetetraacetic Acid (EDTA) and Dithiothreitol (DTT).

Microtiter plate assays were used to study the effect of MgCl$_2$ or DTT. Reactions were carried out at 37° C. in duplicate in 384-well plates with a final volume of 20 μL containing the Tris-HCl buffer (100 mM, pH 7.0), SpNanC (40 ng), Neu5Acα2-3GalβpNP (0.3 mM), β-galactosidase (12 μg) and different concentrations of MgCl$_2$ (5 mM, 10 mM, 20 mM, 50 mM) or EDTA (0.2 mM, 1 mM, 5 mM, 10 mM) or DTT (5 mM, 10 mM). Reactions were allowed to proceed for 30 min and were stopped by adding 40 μL CAPS buffer (0.5 M, pH 10.5). The amount of the p-nitrophenolate formed was determined by measuring the absorbance of the reaction mixtures at 405 nm using a microtiter plate reader. Reactions with GalβpNP (0.3 mM) and β-galactosidase (12 μg) in Tris-HCl buffer (100 mM, pH 7.0) were used as controls. The amount of excess β-galactosidase to be used was predetermined to ensure the complete and fast hydrolysis of the GalβpNP.

Kinetics of α2-3-Sialidase Activity by Capillary Electrophoresis (CE) Assays.

Assays were carried out in duplicate in a total volume of 10 μL in Tris-HCl buffer (pH 7.0, 100 mM) containing SpNanC (12 ng) and Neu5Acα2-3GalβpNP. All reactions were allowed to proceed for 10 min at 37° C. Apparent kinetic parameters were obtained by varying the Neu5Acα2-3GalβpNP concentration from 0.5 to 10.0 mM (0.5 mM, 1.0 mM, 2.0 mM, 4.0 mM, 8.0 mM and 10.0 mM). The reaction mixture was stopped were stopped by adding 10 μL of cold ethanol. Apparent kinetic parameters were obtained by fitting the data into the Michaelis-Menten equation using Grafit 5.0.

Substrates Specificity Assays.

Sialidase substrate specificity assays were carried out at 37° C. in duplicate in 384-well plates in a final volume of 20 μL containing the Tris-HCl buffer (100 mM, pH 7.0), SpNanC (2 μg), a sialoside substrate (0.3 mM), and a β-galactosidase (12 μg). Reactions were carried out for 30 min and were stopped by adding the 40 μL CAPS buffer (0.5 M, pH 10.5).

To produce Sia2ens from the corresponding six-carbon precursors of sialic acids, four enzymes were employed (Scheme 3): a sialic acid aldolase from *Pasteurella multocida* (PmAldolase), a CMP-sialic acid synthetase from *Neisseria meningitidis* (NmCSS), a *Pasteurella multocida* sialyltransferase 1 mutant (PmST1_M144D), and SpNanC. The PmAldolase catalyzes the formation of sialic acid from its six-carbon monosaccharide precursor and pyruvate. The NmCSS catalyzes the conversion of cytidine 5'-triphosphate (CTP) and sialic acid for the formation CMP-sialic acid, which was used together with an acceptor such as lactose by PmST1_M144D for the synthesis of the corresponding α2-3-linked sialosides, providing the substrates for SpNanC for the production of the desired Sia2ens.

sulfate polyacrylamide gel electrophoresis (SDS-PAGE) analysis, in addition to a faint band at around 120 kDa with the expected size of the fusion protein, there was a major band at about 80 kDa corresponding to the protein without the MBP-tag. N-Terminal protein sequencing of the major band indicated that the MBP tag and the first twenty-six amino acids (26 aa) of SpNanC was cleaved during the expression and purification. The resulting protein retained its activity. The N-terminal 26 aa-truncated protein was re-cloned in pET22b(+) vector as a C-His$_6$-tagged recombinant protein (Δ26SpNanC-His$_6$). About 108 mg Ni$^{2+}$-column purified Δ26SpNanC-His$_6$ (abbreviated as SpNanC) can be routinely obtained from one liter *E. coli* culture.

pH profile study of SpNanC using Neu5Acα2-3GalβpNP as the substrate and capillary electrophoresis (CE) detection at A$_{300\ nm}$ (FIG. 1) indicated that the enzyme is active in a pH range of 6.0-9.0 and has highest activity at pH 7.0. It

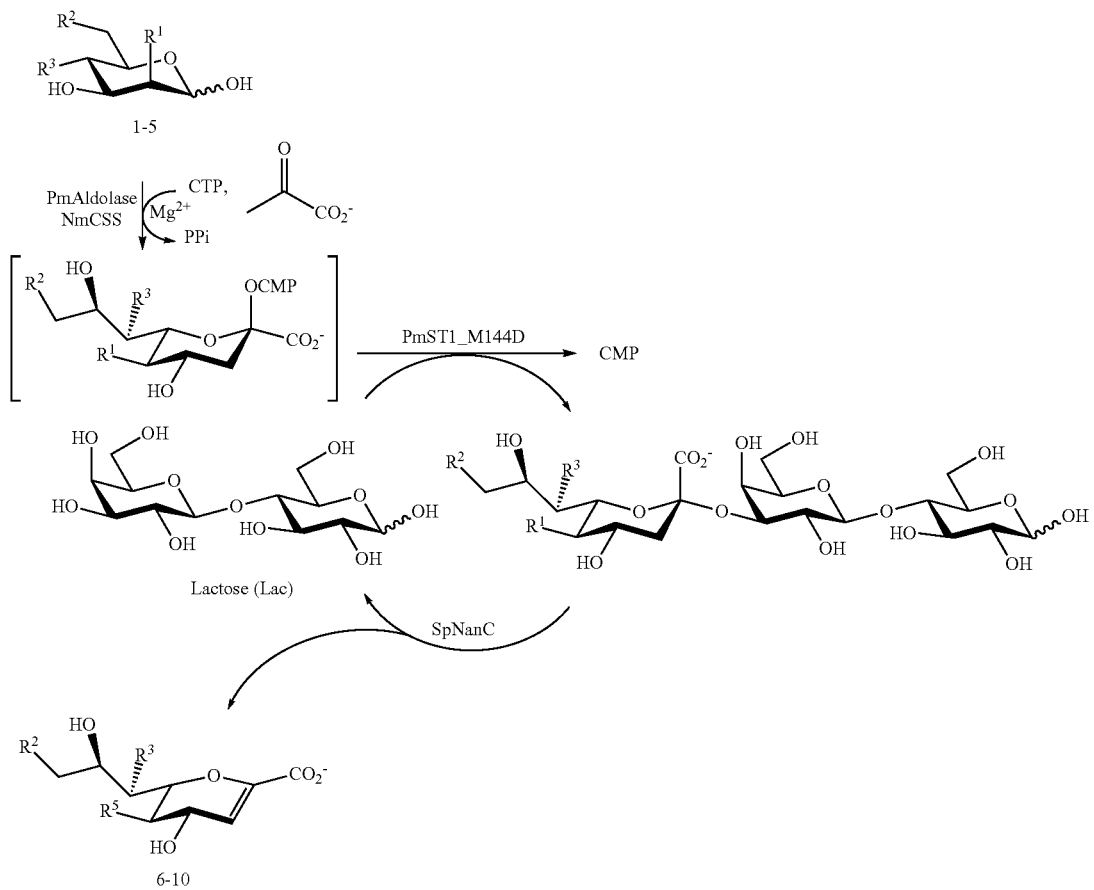

Scheme 3. One-pot four-enzyme (OP4E) synthesis of Sia2ens.

Figure 2:
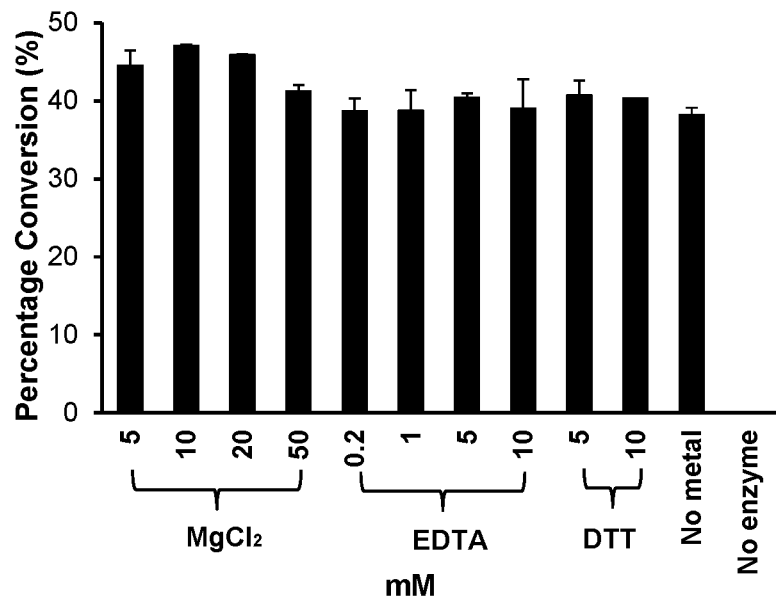
FIG. 2 shows the effects of Mg$^{2+}$, EDTA and DTT on the sialidase activity of SpNanC when Neu5Acα2-3GalβpNP was used as a substrate.
Figure 3:
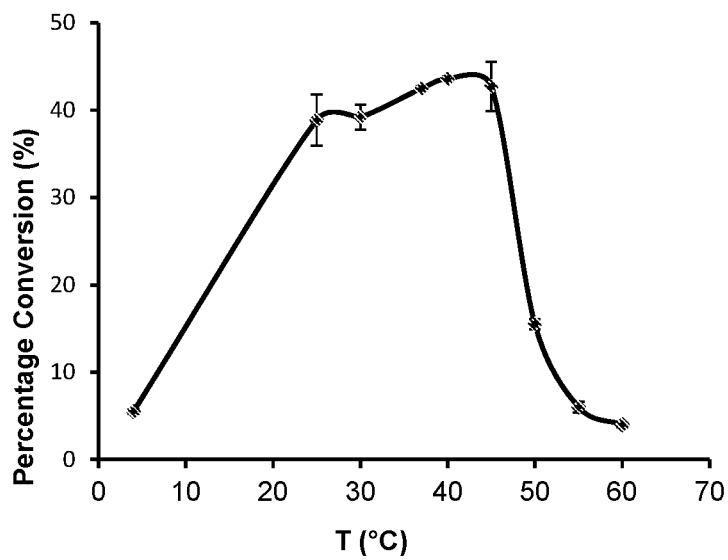
FIG. 3 shows the temperature profile of SpNanC using Neu5Acα2-3GalβpNP as the substrate. The assay was done at temperatures ranging from 4° C. to 60° C. Reactions were allowed to proceed in MES buffer (pH 6.5, 100 mM) for 10 min.
Figure 4:
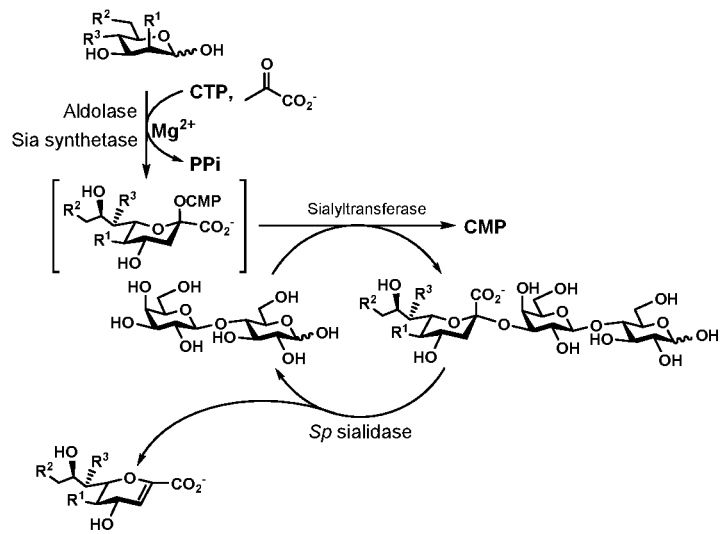
FIG. 4 shows one embodiment of a procedure for one-pot, multi-enzyme synthesis of 2-deoxy-2,3-dehydro-sialic acids according to the present disclosure.

ManNAc (1) & Neu5Ac2en (6): R$^1$ = NHAc, R$^2$ = OH; R$^3$ = OH
ManNGc (2) & Neu5Gc2en (7): R$^1$ = NHGc, R$^2$ = OH; R$^3$ = OH
ManNAc6N$_3$ (3) & Neu5Ac9N$_3$2en (8): R$^1$ = NHAc, R$^2$ = N$_3$; R$^3$ = OH
ManNAc6NAc (4) & Neu5Ac9NAc2en (9): R$^1$ = NHAc, R$^2$ = NHAc; R$^3$ = OH
ManNAc4deoxy (5) & Neu5Ac7deoxy2en (10): R$^1$ = NHAc, R$^2$ = OH; R$^3$ = H To obtain sufficient amounts of SpNanC for the OPME synthesis of Sia2ens, full length SpNanC from *Streptococcus pneumonia* TIGR4 was cloned in pMAL-c4X vector and expressed as an N-terminal maltose binding protein (MBP)-fused and C-terminal His$_6$-tagged recombinant protein in *Escherichia coli* BL21(DE3) cells. Ni$^{2+}$-affinity column purified MBP-SpNanC-His$_6$ showed by sodium dodecyl does not require a metal ion for activity and the addition of a reducing reagent dithiothreitol (DTT) does not affect its activity (FIG. 2). Kinetics studies indicated that SpNanC is a highly active sialidase using Neu5Acα2-3GalβpNP as the substrate ($k_{cat}/K_M$=150 s$^{-1}$ mM$^{-1}$ with $K_M$=2.7±0.5 mM and $k_{cat}$=406.8±39.0 s$^{-1}$) compared to a previously reported recombinant SpNanC using α2-3-sialyllactose as the substrate ($k_{cat}/K_M$=0.29 s$^{-1}$ mM$^{-1}$ with $K_M$=1.08±0.35 mM, $k_{cat}$=0.313±0.052 s$^{-1}$).

Substrate specificity studies of SpNanC using a library of para-nitrophenol (pNP)-tagged α2-3-linked sialosides indicated that the enzyme can tolerate Neu5Ac modifications at C-5, C-9, and C-7.

TABLE 1

Substrate specificity of SpNanC.

| Substrate | Percentage conversion (%) |
|---|---|
| Neu5Acα2-3GalβpNP | 85.1 ± 2.4 |
| Neu5AcFα2-3GalβpNP | 74.8 ± 3.2 |
| Neu5AcOMeα2-3GalβpNP | 81.8 ± 1.7 |
| Neu5AcN$_3$α2-3GalβpNP | 87.9 ± 1.6 |
| Neu5Ac9Fα2-3GalβpNP | 75.6 ± 3.9 |
| Neu5Ac9OMeα2-3GalβpNP | 88.5 ± 5.1 |
| Neu5Ac9deoxyα2-3GalβpNP | 93.5 ± 3.1 |
| Neu5Ac7Fα2-3GalβpNP | 91.0 ± 4.3 |
| Neu5Ac7OMeα2-3GalβpNP | 96.5 ± 1.7 |
| Neu5Ac7deoxyα2-3GalβpNP | 91.2 ± 1.8 |
| Neu5Ac7N$_3$α2-3GalβpNP | 65.9 ± 1.1 |
| Neu5Gcα2-3GalβpNP | 80.6 ± 6.7 |
| Neu5Gc9Fα2-3GalβpNP | 72.3 ± 2.6 |
| Neu5Gc9OMeα2-3GalβpNP | 75.0 ± 1.9 |
| Neu5Gc9deoxyα2-3GalβpNP | 85.5 ± 1.4 |
| Neu5Gc9N$_3$α2-3GalβpNP | 89.5 ± 3.5 |
| Kdnα2-3GalβpNP | 4.50 ± 0.45 |
| Kdn5Fα2-3GalβpNP | 0.48 ± 0.00 |
| Kdn5N$_3$α2-3GalβpNP | 0.32 ± 0.45 |
| Kdn5deoxyα2-3GalβpNP | 5.31 ± 0.23 |
| Kdn5OMe α2-3GalβpNP | 1.53 ± 1.02 |
| Kdn9Fα2-3GalβpNP | 3.70 ± 1.14 |
| Kdn9OMeα2-3GalβpNP | 4.02 ± 1.36 |
| Kdn7Fα2-3GalβpNP | 0.56 ± 0.11 |
| Kdn7OMeα2-3GalβpNP | 23.4 ± 3.3 |
| Kdn7deoxyα2-3GalβpNP | 10.1 ± 0.0 |
| Kdn7N$_3$α2-3GalβpNP | 4.50 ± 0.45 |

Different from what was described in a previous report, sialosides with non-human sialic acid form N-glycolylneuraminic acid (NeuSGc) and its C-9 derivatives are also suitable substrates for the enzyme. Sialosides containing 2-keto-3-deoxynonulsonic acid (Kdn) or its derivatives with modifications at C-5, or C-9 are not effective substrates of SpNanC. Among compounds tested, two of the sialosides containing C7-modified Kdn (Kdn7OMeα2-3GalβpNP and Kdn7deoxyα2-3GalβpNP) were able to be cleaved off by SpNanC with low yields (23% and 10% respectively in reactions using 3 μg of SpNanC) (Table 1).

The substrate promiscuities of SpNanC and enzymes involved in one-pot multienzyme (OPME) synthesis of sialosides provided an opportunity for synthesizing Sia2ens from six-carbon precursors of sialic acids. Because SpNanC has a dual function of forming Neu5Ac2en from sialosides and further hydration of Neu5Ac2en to form Neu5Ac, the effects of SpNanC loading in the one-pot four-enzyme reaction was studied. A concentration of SpNanC in the range of 0.004-0.04 mg/mL was useful for reactions containing 10 mM of the ManNAc precursor, as assessed by conducting small scale reactions followed by thin layer chromatography (TLC) and mass spectroscopy analyses suggested that. Secondly, the choice of the acceptor and the amount needed to be considered. Due to its low cost, commercially available lactose was chosen as the acceptor. As shown in Scheme 3, lactose is used as a sialyltransferase acceptor and is regenerated in the SpNanC reaction. Therefore, only a catalytic amount of lactose is needed for the Sia2en production reactions. For example, 0.25 equivalents (2.5 mM) of lactose provided a good reaction rate. Thirdly, the choice of pH of the reaction mixture was considered. SpNanC is active in a pH range of 6.0-9.0 and has highest activity at pH 7.0 and good activity in the pH range of 6.0-7.5 (FIG. 1) while NmCSS is active in the pH range of 7.0-10.0 with highest activity at pH 9.0. PmAldolase has good activity in the pH range of 6.0-9.0 and wild-type PmST1 maintains good α2-3-sialyltransferase activity in the pH range of 6.0-10.0. A pH of 7.5 with Tris-HCl buffer was chosen for the OPME reaction to balance the pH preference of SpNanC and NmCSS. Neu5Ac2en (6) can be synthesized from ManNAc (1) in 72% yield using the methods described herein.

Example 2. Pre-Formation of Sialosides Increases Sia2en Yields

Similar reaction conditions were applied to N-glycolylmannosamine (ManNGc, 2, the six-carbon precursor for non-human Neu5Gc) for the synthesis of Neu5Gc2en (7). Surprisingly, only a trace amount of the desired product was obtained. To overcome this challenge, an alternative two-step procedure was developed. In this case, a one-pot three-enzyme sialoside formation reaction with equal molar amounts of lactose and ManNGc was carried out overnight before SpNanC was added. The yield for Neu5Gc2en (7) was improved to 60% by the two-step procedure. A similar two-step procedure applied for the synthesis of Neu5Ac2en (6) was able to improve the yield from 72% of the one-step procedure to 82%.

TABLE 2

Sia2ens obtained by OPME synthesis.

| Substrate | Product | Yield[a] | Yield[b] |
|---|---|---|---|
| ManNAc (1) | Neu5Ac2en (6) | 72% | 82% |

TABLE 2-continued

Sia2ens obtained by OPME synthesis.

| Substrate | Product | Yield[a] | Yield[b] |
|---|---|---|---|
| ManNGc (2) | Neu5Gc2en (7) | <5%[c] | 60% |
| ManNAc6N₃ (3) | Neu5Ac9N₃2en (8) | 61% | 79% |
| ManNAc6NAc (4) | Neu5Ac9NAc2en (9) | 63% | 71% |
| ManNAc4deoxy (5) | Neu5Ac7deoxy2en (10) | 11% | 25% |

[a]One-step reactions.
[b]Two-step reactions.
[c]Determined by TLC analysis.

One-Pot Four-Enzyme (OP4E) Synthesis of Sia2ens (One-Step Procedure).

ManNAc or its derivatives (20-300 mg), lactose (0.25 equiv.), sodium pyruvate (8 equiv.), CTP (1.5 equiv.) were dissolved in Tris-HCl buffer (100 mM, pH 7.5, 10-20 mL) containing 20 mM of $MgCl_2$. The pH of the solution was further adjusted to 7.5 with 4 M NaOH. PmAldolase (1.5-3.0 mg), NmCSS (1.0-2.0 mg), PmST1_M144D (2.0-4.0 mg), SpNanC (0.05-0.2 mg) were added and the reaction was incubated in an isotherm incubator for 3-6 h at 37° C. with agitation at 100 rpm. The reaction was quenched by adding the same volume of ice-cold ethanol and incubating at 4° C. for 1 h. The formed precipitates were removed by centrifugation and the supernatant was concentrated. The residue was purified gradually by passing it through a BioGel P-2 gel filtration column, a silica column (EtOAc/MeOH/$H_2O$=4:2:0.2), followed by a $C_{18}$ column (100% $H_2O$) to give the pure compound.

One-Pot Four-Enzyme (OP4E) Synthesis of Sia2ens (Two-Step Procedure).

ManNAc or its derivatives (20-300 mg), lactose (1.0 equiv.), sodium pyruvate (8 equiv.), CTP (1.5 equiv.) were dissolved in Tris-HCl buffer (100 mM, pH 8.5, 10-20 mL) containing 20 mM of $MgCl_2$. The pH of the solution was further adjusted to 8.5 with 4 M NaOH. PmAldolase (1.5-3.0 mg), NmCSS (1.0-2.0 mg), PmST1_M144D (2.0-4.0 mg) were added and the reaction was incubated in an isotherm incubator overnight at 37° C. with agitation at 100 rpm to ensure a full completion of the sialoside formation. SpNanC (0.05-0.2 mg) was added afterwards and the reaction was incubated for another 3-8 h until the reaction was finished. The work-up procedures were the same as described in the one-step procedure.

5-Acetamido-2,6-anhydro-3,5-dideoxy-D-glycero-D-galacto-non-2-enonic acid (Neu5Ac2en, 6)

Yield, 72% for one-step procedure; 82% for two-step procedure; white solid. The spectroscopic data coincide with the previous report.

2,6-Anhydro-3,5-dideoxy-5-glycolylamido-D-glycero-D-galacto-non-2-enonic acid (Neu5Gc2en, 7)

Yield, <5% based on TLC for one-step procedure; 60% for two-step procedure; white solid. The spectroscopic data coincide with the previous report.

5-Acetamido-2,6-anhydro-9-azido-3,5,9-trideoxy-D-glycero-D-galacto-non-2-enonic acid (Neu5Ac9N$_3$2en, 8)

Yield, 61% for one-step procedure; 79% for two-step procedure; white solid. The spectroscopic data coincide with the previous report.

5,9-Diacetamido-2,6-anhydro-3,5,9-trideoxy-D-glycero-D-galacto-non-2-enonic acid (Neu5Ac9NAc2en, 9)

Yield, 63% for one-step procedure; 71% for two-step procedure; white solid. $^1$H NMR (400 MHz, D$_2$O) δ 6.02 (d, J=2.4 Hz, 1H, H-3), 4.51 (dd, J=8.8, 2.4 Hz, 1H, H-4), 4.29 (dd, J=10.8, 1.2 Hz, 1H, H-6), 4.09 (dd, J=10.8, 8.8 Hz, 1H, H-5), 3.96 (ddd, J=9.2, 7.4, 3.2 Hz, 1H, H-8), 3.62 (dd, J=14.2, 3.2 Hz, 1H, H-9), 3.55 (dd, J=9.2, 1.2 Hz, 1H, H-7), 3.29 (dd, J=14.2, 7.4 Hz, 1H, H-9), 2.07 (s, 3H, COCH3), 2.02 (s, 3H, COCH$_3$); $^{13}$C NMR (100 MHz, D$_2$O) δ 174.69, 174.62, 165.75, 143.91, 112.14, 75.76, 69.25, 68.33, 67.06, 49.60, 42.59, 22.05, 21.79; HRMS (ESI) Anal. Calcd for C$_{13}$H$_{19}$N$_2$O$_8$ [M-H]$^-$: 331.1147, Found: 331.1131.

5-Acetamido-2,6-anhydro-3,5,7-trideoxy-D-glycero-D-galacto-non-2-enonic acid (Neu5Ac7deoxy2en, 10)

Yield, 11% for one-step procedure; 25% for two-step procedure. $^1$H NMR (400 MHz, D$_2$O) δ 5.75 (d, J=2.8 Hz, 1H, H-3), 4.36 (dd, J=8.0, 2.8 Hz, 1H, H-4), 4.15 (td, J=9.6, 2.4 Hz, 1H, H-6), 4.08-4.00 (m, 1H, H-8), 3.87 (dd, J=9.6, 8.0 Hz, 1H, H-5), 3.61 (dd, J=11.6, 4.0 Hz, 1H, H-9), 3.49 (dd, J=11.8, 6.8 Hz, 1H, H-9), 2.06 (s, 3H, COCH$_3$), 1.84-1.76 (m, 1H, H-7), 1.74-1.66 (m, 1H, H-7); $^{13}$C NMR (100 MHz, D$_2$O) δ 174.42, 169.61, 147.88, 107.49, 74.13, 67.39, 66.95, 65.73, 53.43, 33.73, 22.06; HRMS (ESI) Anal. Calcd for C$_{11}$H$_{16}$NO$_7$ [M-H]$^-$: 274.0932, Found: 274.0916.

In general, the one-pot procedure is more time efficient and the reactions are usually completed within a 2-6 hour time frame. In comparison, the two-step procedure is commonly performed for 12-20 hours in total but can improve the synthetic yield especially for the processes with slow sialoside formation rates.

The enzymatic approach compared favorably to the traditional chemical methods which used organic solvents and involved multiple protection and deprotection steps. For example, chemical synthesis of Neu5Ac9NAc2en (9) from Neu5Ac involved nine steps and multiple purification processes with an overall yield of 9-14% (see, Magesh, et al. *Bioorg. Med. Chem. Lett*. 2008, 18, 532-537). For the chemoenzymatic approach described here, ManNAc6NAc (4) was chemically synthesized from ManNAc via ManNAc6N$_3$ (3) intermediate in three steps with a 48% overall yield. Considering the 63% or 71% yield for the one-step or two-step OPME synthetic process (Table 2), the overall yield for Neu5Ac9NAc2en (9) was 30% or 34% starting from ManNAc without the need of purifying the intermediates of enzymatic reactions.

Example 3. Synthetic Elaboration of Sia2ens at C-5, C-9, and C-7

Other than OPME synthesis of Neu5Gc2en, the synthesis of a C-5 derivative of Neu5Ac2en and C-9 derivatives of Neu5Ac2en were also carried out. Neu5Ac9N$_3$2en (8) containing an C9-azido group was synthesized from ManNAc6N$_3$ (3) in a yield of 61% using the one-step procedure, and 79% with the two-step procedure. Similarly, Neu5Ac9NAc2en (9) containing a C9-acetamido group was synthesized from ManNAc6NAc (4) in a yield of 63% with the one-step procedure and 71% using the two-step procedure. Neu5Ac9NAc2en (9) is a more stable analog of Neu5Ac9OAc2en and may be a better inhibitor for sialidases that prefer to cleave 9-O-acetyl Neu5Ac.

The OPME system was also tested for the synthesis of a C-7 derivative of Neu5Ac2en. The one-step procedure was able to obtain the target compound Neu5Ac7deoxy2en (10) from ManNAc4deoxy (5) in a low 11% yield. The two-step procedure was able to improve the yield to 25%. The lower yield was believed to be due to the lower efficiency in sialoside formation.

Derivatization at C-9 of Neu5Ac9N$_3$2en

5-Acetamido-9-amino-2,6-anhydro-3,5,9-trideoxy-D-glycero-D-galacto-non-2-enonic acid (Neu5Ac9NH$_2$2en, 11)

To a stirred solution of Neu5Ac9N$_3$2en (40 mg, 0.12 mmol) in mixed solvent of pyridine/H$_2$O (1.5 mL/1.5 mL), 1,3-propanedithiol (120 μL, 1.2 mmol) and triethylamine (160 μL, 1.1 mmol) were added and the mixture was stirred for 24 h. The solvent was concentrated in vacuo. The crude product was re-dissolved in water. One drop of 1M NaOH was added to replace the triethylamine salt formed with the carboxylic acid. The solution was passed through a BioGel P-2 gel filtration column to give 11 (35 mg, 95%) as a white solid. This compound was directly utilized for subsequent reactions without further characterization.

5-Acetamido-2,6-anhydro-3,5,9-trideoxy-9-valeramido-D-glycero-D-galacto-non-2-enonic acid (Neu5Ac9NPent2en, 12)

To a stirred solution of Neu5Ac9NH$_2$2en (15.8 mg, 0.0506 mmol) in mixed solvent of THF/H$_2$O (2.0 mL/0.5 mL), pentanoyl chloride (12 μL, 0.10 mmol) and triethylamine (35 μL, 0.25 mmol) were added and the mixture was stirred for 2.5 h. The solvent was concentrated in vacuo. The crude product was re-dissolved in water. One drop of 1M NaOH was added to replace the triethylamine salt formed with the carboxylic acid. The solution was passed through a BioGel P-2 gel filtration column to give 12 (18.2 mg, 91%) as a white solid. $^1$H NMR (400 MHz, D$_2$O) δ 5.70 (d, J=2.4 Hz, 1H, H-3), 4.47 (dd, J=8.8, 2.4 Hz, 1H, H-4), 4.22 (dd, J=10.8, 1.2 Hz, 1H, H-6), 4.06 (dd, J=10.8, 8.8 Hz, 1H, H-5), 3.98 (ddd, J=9.2, 7.0, 3.2 Hz, 1H, H-8), 3.58 (dd, J=14.2, 3.2 Hz, 1H, H-9), 3.51 (dd, J=9.2, 1.2 Hz, 1H, H-7), 3.37 (dd, J=14.2, 7.0 Hz, 1H, H-9), 2.36-2.23 (m, 2H, CH$_2$), 2.08 (s, 3H, COCH$_3$), 1.64-1.52 (m, 2H, CH$_2$), 1.39-1.26 (m, 2H, CH$_2$), 0.90 (t, J=7.4 Hz, 3H, CH$_3$); $^{13}$C NMR (100 MHz, D$_2$O) δ 177.89, 174.60, 169.59, 147.92, 107.60, 75.20, 69.41, 68.33, 67.55, 49.92, 42.37, 35.51, 27.66, 22.11, 21.54, 12.98; HRMS (ESI) Anal. Calcd for C$_{16}$H$_{25}$N$_2$O$_8$ [M-H]$^-$: 373.1616, Found: 373.1597.

5-Acetamido-2,6-anhydro-9-cyclopropylcarboxamido-3,5,9-trideoxy-D-glycero-D-galacto-non-2-enonic acid (Neu5Ac9NCyclopro2en, 13)

To a stirred solution of Neu5Ac9NH$_2$2en (19.3 mg, 0.0618 mmol) in mixed solvent of THF/H$_2$O (2.0 mL/0.5 mL), cyclopropanecarbonyl chloride (11 μL, 0.12 mmol) and triethylamine (43 μL, 0.31 mmol) were added and the mixture was stirred for 5 h. The solvent was concentrated in vacuo. The crude product was re-dissolved in water. One drop of 1M NaOH was added to replace the triethylamine salt formed with the carboxylic acid. The solution was passed through a BioGel P-2 gel filtration column to give 13 (26.2 mg, 85%) as a white solid. $^1$H NMR (400 MHz, D$_2$O) δ 5.70 (d, J=2.4 Hz, 1H, H-3), 4.47 (dd, J=8.8, 2.4 Hz, 1H, H-4), 4.22 (dd, J=10.8, 1.2 Hz, 1H, H-6), 4.06 (dd, J=10.8, 8.8 Hz, 1H, H-5), 3.99 (ddd, J=9.4, 7.2, 3.2 Hz, 1H, H-8), 3.62 (dd, J=14.2, 3.2 Hz, 1H, H-9), 3.51 (dd, J=9.2, 1.2 Hz, 1H, H-7), 3.37 (dd, J=14.2, 7.2 Hz, 1H, H-9), 2.08 (s, 3H, COCH$_3$), 1.73-1.61 (m, 1H, CH), 0.89-0.83 (m, 4H, CH$_2$CH$_2$); $^{13}$C NMR (100 MHz, D$_2$O) δ 177.84, 174.58, 169.60, 147.92, 107.57, 75.17, 69.34, 68.39, 67.53, 49.88, 42.65, 22.09, 13.97, 6.69, 6.62; HRMS (ESI) Anal. Calcd for C$_{15}$H$_{21}$N$_2$O$_8$ [M-H]$^-$: 357.1303, Found: 357.1285.

Derivatization at C-5 of Neu5Ac2en

5-Amino-2,6-anhydro-3,5-dideoxy-D-glycero-D-galacto-non-2-enonic acid (Neu2en, 14)

A solution of Neu5Ac2en (200 mg, 0.639 mmol) in 2M NaOH (10 mL) was stirred at 75° C. for 12 h. The solution was directly passed through a BioGel P-2 gel filtration column to give 14 (156 mg, 90%) as a white solid. This compound was directly utilized for subsequent reactions without further characterization.

2,6-Anhydro-3,5-dideoxy-5-glycolylamido-D-glycero-D-galacto-non-2-enonic acid (Neu5Gc2en, 7)

To a stirred solution of Neu2en (22.3 mg, 0.0822 mmol) in anhydrous MeOH (1 mL), acetoxyacetyl chloride (17 μL, 0.16 mmol) and K$_2$CO$_3$ (22.7 mg, 0.16 mmol) were added and the mixture was stirred for 6 h. The solvent was concentrated in vacuo. The crude product was re-dissolved in H$_2$O (2 mL), and the pH of the solution was adjusted to 10-11 by adding 1M NaOH. The solution was stirred for 1 h and was neutralized by Dowex®50WX4 ion-exchange resin (H+). The solvent was concentrated in vacuo. The crude product was purified by column chromatography (EtOAc/MeOH/H$_2$O=4:2:0.2), followed by a short BioGel P-2 gel filtration column to give 7 (20.3 mg, 74.8%) as a white solid. The spectroscopic data coincide with the previous report.

2,6-Anhydro-3,5-dideoxy-5-phenylacetamido-D-glycero-D-galacto-non-2-enonic acid (Neu5PhAc2en, 15)

To a stirred solution of Neu2en (40.0 mg, 0.147 mmol) in mixed solvent of THF/H$_2$O (3.0 mL/1.5 mL), phenylacetyl chloride (80 μL, 0.60 mmol) and triethylamine (200 μL, 1.43 mmol) were added and the mixture was stirred for 24 h. The solvent was concentrated in vacuo. The crude product was purified by column chromatography (EtOAc/MeOH/H$_2$O=4:2:0.2). The product was re-dissolved in water. One drop of 1M NaOH was added to replace the triethylamine salt formed with the carboxylic acid. The solution was passed through a BioGel P-2 gel filtration column to give 15 (28.0 mg, 49%) as a white solid. $^1$H NMR (400 MHz, D$_2$O) δ 7.58-7.14 (m, 5H, C$_6$H$_5$), 5.69 (d, J=2.4 Hz, 1H, H-3), 4.50 (dd, J=8.8, 2.4 Hz, 1H, H-4), 4.22 (dd, J=10.8, 1.2 Hz, 1H, H-6), 4.06 (dd, J=10.8, 8.8 Hz, 1H, H-5), 3.89 (ddd, J=9.6, 6.4, 2.6 Hz, 1H, H-8), 3.81 (dd, J=12.0, 2.6 Hz, 1H, H-9), 3.69 (d, J=3.2 Hz, 2H, CH$_2$), 3.52 (dd, J=12.0, 6.4 Hz, 1H, H-9), 3.40 (dd, J=9.6, 1.2 Hz, 1H, H-7); $^{13}$C NMR (100 MHz, D$_2$O) δ 175.25, 169.62, 147.85, 134.91, 129.10, 128.98, 127.37, 107.64, 75.19, 69.76, 68.25, 67.34, 63.17, 49.89, 42.63; HRMS (ESI) Anal. Calcd for C$_{17}$H$_{20}$NO$_8$ [M-H]$^-$: 366.1194, Found: 366.1176.

Enzymatic Synthesis of Neu5AcαOMe

Neu5Ac2en (100.5 mg, 0.3208 mmol) was dissolved in a mixed solvent of H$_2$O/MeOH (7.5 mL/2.5 mL) containing Tris-HCl buffer (100 mM, pH 7.0). SpNanC (8 mg) was added in two portions at an interval of 4 h and the reaction was incubated in an isotherm incubator for 24 h at 37° C. with agitation at 100 rpm. The reaction was quenched by adding the same volume of ice-cold ethanol and incubating at 4° C. for 1 h. The formed precipitates were removed by centrifugation and the supernatant was concentrated. The residue was purified by column chromatography (EtOAc/MeOH/H$_2$O=5:2:0.2) followed by a C18 column (100% H$_2$O) to give Neu5AcαOMe (71.8 mg, 65%) as a white solid. The spectroscopic data coincide with the previous report.

The C9-azido group of Neu5Ac9N$_3$2en (8) allows further derivatization to be carried out. The azido group of Neu5Ac9N$_3$2en (8) was reduced to a free amino group with 1,3-propanedithiol to produce intermediate 11, after which different groups were installed (Scheme 4). This provided for the preparation of Neu5Ac9NPent2en (12), with an improved selectivity against human NEU1, and Neu5Ac9NCyclopro2en (13), with a higher selectivity against viral sialidases.

Scheme 4. Derivatization at C-9 of Neu5Ac9N$_3$2en (8).

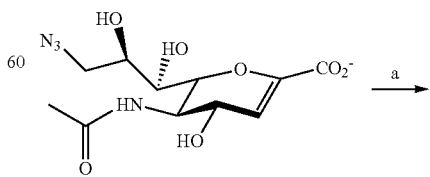

8

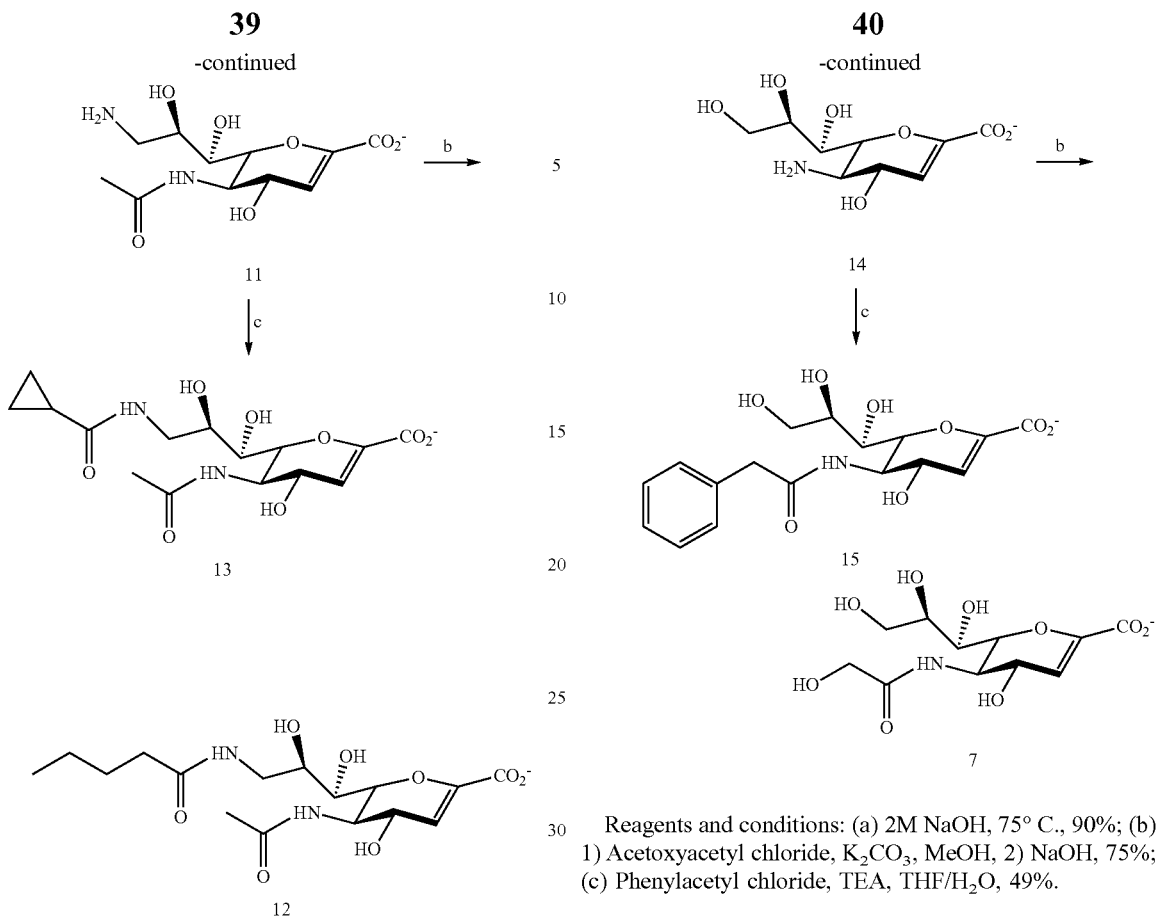

Reagents and conditions: (a) 2M NaOH, 75° C., 90%; (b) 1) Acetoxyacetyl chloride, K$_2$CO$_3$, MeOH, 2) NaOH, 75%; (c) Phenylacetyl chloride, TEA, THF/H$_2$O, 49%.

Example 4. Sialidase Inhibition with Sia2ens

Inhibition assays were carried out in duplicates in 384-well plates in a final volume of 20 µL containing Neu5Acα2-3GalβpNP (0.3 mM) and β-galactosidase (12 µg) with or without inhibitors. The assay conditions varied for different sialidases as described below: SpNanA (0.0015 µg), NaOAc buffer (100 mM, pH 6.0); SpNanB (0.003 µg), NaOAc buffer (100 mM, pH 6.0); SpNanC (0.02 µg), MES buffer (100 mM, pH 6.5); AuSialidase (1.0 mU), NaOAc buffer (100 mM, pH 5.5); CpNanI (2.0 mU), MES buffer (100 mM, pH 5.0); CpNanH (0.5 mU), MES buffer (100 mM, pH 5.0); VcSialidase (1.5 mU), NaCl (150 mM), CaCl$_2$ (10 mM), NaOAc buffer (100 mM, pH 5.5); PmST1 (34.4 µg), NaOAc buffer (100 mM, pH 5.5); BiNanH2, NaOAc buffer (100 mM, pH 5.0); hNEU2 (22.0 µg), MES buffer (100 mM, pH 5.0). The reactions were incubated for 30 min at 37° C., and were stopped by adding CAPS buffer (N-cyclohexyl-3-aminopropane sulfonic acid, 40 µL, 0.5 M, pH 10.5). The amount of the para-nitrophenolate formed was determined by measuring the $A_{405\ nm}$ Of the reaction mixtures using a microplate reader.

The percentage inhibitions were determined using a concentration of 0.1 mM of each inhibitor, with reactions without inhibitors as controls. IC$_{50}$ values were tested by varying the concentrations of inhibitors from 0 to 1000 µM to get the concentration-response plots of the inhibitors. The values of IC$_{50}$ were calculated by the software Grafit 5.0.

The obtained compounds were tested as inhibitors against several glycoside hydrolase GH33 family sialidases as described above. The sialidases were categorized based on their protein sequence similarity in the Carbohydrate Active Enzyme (CAZy) database. These include human cytosolic sialidase hNEU2 and several bacterial sialidases including Reagents and conditions: (a) 1,3-propanedithiol, TEA, Py/H$_2$O, 95%; (b) pentanoyl chloride, TEA, THF/H$_2$O, 91%; (c) cyclopropanecarbonyl chloride, TEA, THF/H$_2$O, 85%.

The C-5 group of Neu5Ac2en (6) can also be easily derivatized by removal of the N-acetyl group at C-5 using 2 M of sodium hydroxide solution to produce Neu2en (14) with a free amino group at C-5. Selective acylation of the amino group on C-5 afterwards provided the C5-derivatized Sia2ens conveniently (Scheme 5). Neu5Gc2en (7) was again generated by this method. Neu5PhAc2en (15) was also synthesized conveniently.

Scheme 5. Derivatization at C-5 of Neu5Ac2en (6).

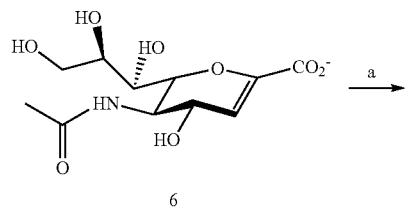

recombinant enzymes cloned from *Streptococcus pneumoniae* (SpNanA, SpNanB, and SpNanC), *Pasteurella multocida* (PmST1), *Bifidobacterium infantis* (BiNanH2), as well as commercially available sialidases from *Arthrobacter ureafaciens* (AuSialidase), *Clostridium perfringens* (CpNanI, CpNanH), and *Vibrio cholerae* (VcSialidase). Inhibition studies using Neu5Acα2-3GalβpNP as the sialidase substrate and 0.1 mM of each inhibitor showed that overall, Neu5Ac2en (6) and its derivatives at C5, C9, and C7 are not suitable inhibitors against SpNanB, SpNanC, CpNanH, and PmST1 (Table 3).

TABLE 3

Percentage inhibition (%) of Sia2ens against bacterial and human sialidases.

| Sialidases | Inhibitors[a] | | | | | | |
|---|---|---|---|---|---|---|---|
| | (6) | (7) | (9) | (10) | (12) | (13) | (15) |
| SpNanA | 89 | 14 | 86 | 89 | 85 | 91 | 2 |
| SpNanB | 4 | 4 | 4 | 2 | 3 | 2 | 5 |
| SpNanC | 11 | 17 | 8 | 5 | 11 | 16 | 12 |
| AuSialidase | 91 | 47 | 60 | 85 | 40 | 61 | 13 |
| CpNanI | 64 | 20 | 63 | 57 | 40 | 51 | 19 |
| CpNanH | 2 | 9 | 1 | 11 | 3 | 7 | 8 |
| VcSialidase | 84 | 87 | 45 | 40 | 43 | 40 | 5 |
| PmST1 | 2 | 2 | 19 | 15 | 8 | 3 | 8 |
| BiNanH2 | 67 | 19 | 69 | 30 | 71 | 78 | 17 |
| hNEU2 | 76 | 68 | 27 | 42 | 19 | 17 | 81 |

[a] 0.1 mM of each inhibitor was used

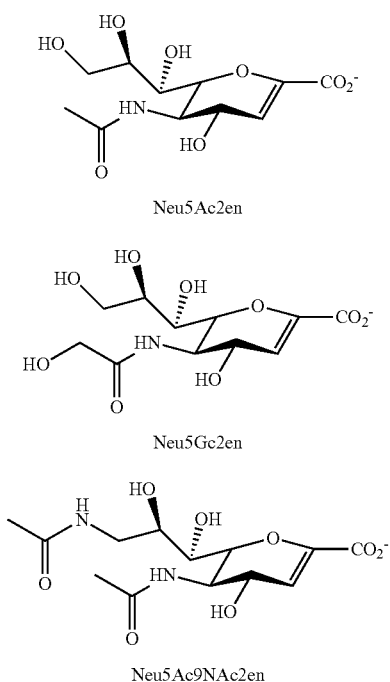

Neu5Ac2en (6)

Neu5Gc2en (7)

Neu5Ac9NAc2en (9)

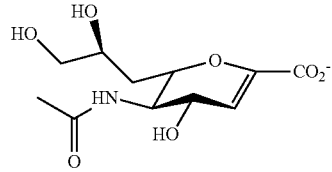

Neu5Ac7deoxy2en (10)

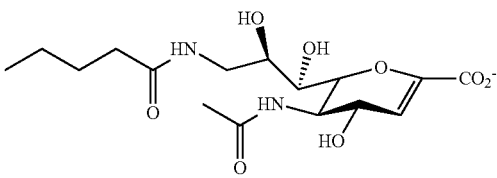

Neu5Ac9NPent2en (12)

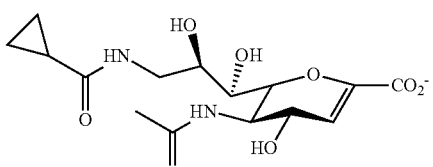

Neu5Ac9NCyclopro2en (13)

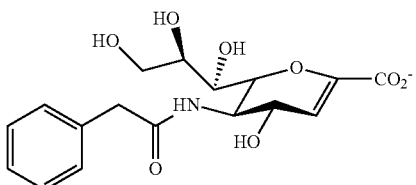

Neu5PhAc2en (15)

On the other hand, Neu5Ac2en (6) is an overall broad spectrum inhibitor among all compounds tested and had more than 50% inhibition against SpNanA, AuSialidase, CpNanI, VcSialidase, BiNanH2, and hNEU2. In comparison, Neu5Gc2en (7) was much more selective and had more than 50% inhibition against only VcSialidase and hNEU2 as reported previously. C9-Derivatization of Neu5Ac2en such as Neu5Ac9Ac2en (9), Neu5Ac9NPent2en (12), and Neu5Ac9NCyclopro2en (13) did not affect the percentage inhibition of SpNanA, CpNanI, or BiNanH2 but lower the inhibitory activity against AuSialidase, VcSialidase. The C9-modification of Neu5Ac2en was not well tolerated by hNEU2. In comparison, C5-derivatization of Neu5Ac2en by substituting the N-acetyl group with an N-benzylcarbonyl group (Neu5PhAc2en, 15) was only well tolerated by hNEU2, but not by any bacterial sialidases tested. It was shown previously that α2-3-sialyl GalβpNP containing a terminal C7-deoxy Neu5Ac was a good substrate for several bacterial sialidases such as PmST1, VcSialidase, *Salmonella typhimurium* sialidase, SpNanB, and CpNanI, but was a poor substrate for hNEU2. It was hypothesized that Neu5Ac7deoxy2en (10) would be an inhibitor selective against several bacterial sialidases but not hNEU2. Indeed, it retained the inhibitory activity of Neu5Ac2en (6) against SpNanA, AuSialidase, CpNanI. However, the inhibition against VcSialidase, BiNanH2, and hNEU2 was decreased simultaneously.

For inhibitors with more than 65% inhibitory activity at 0.1 mM, $IC_{50}$ values were obtained. As shown in Table 4, derivatization at C-5, and C-9 of Neu5Ac2en (6) did not alter its inhibitory activity against SpNanA or BiNanH2 significantly with $IC_{50}$ values retained at around 6.8-11.0 μM and 29-40 μM, respectively. The C7-deoxy modification also did not alter the inhibition activity against SpNanA, but decreased inhibitor activity against AuSialidase and increased $IC_{50}$ value from 8.1 μM to 17 μM.

TABLE 4

$IC_{50}$ values of Sia2ens against bacterial sialidases SpNanA, AuSialidase, and BiNanH2.

| Sialidase | $IC_{50}$ values of different inhibitors (μM) | | | | |
|---|---|---|---|---|---|
| | 6 | 9 | 10 | 12 | 13 |
| SpNanA | 10.0 ± 0.2 | 11.0 ± 0.2 | 10.7 ± 0.4 | 10.5 ± 0.5 | 6.8 ± 0.2 |
| AuSialidase | 8.1 ± 0.3 | — | 17 ± 1 | — | — |
| BiNanH2 | 40 ± 2 | 33 ± 1 | — | 34 ± 2 | 29 ± 2 |

A one-pot enzymatic strategy has been successfully developed for the synthesis of sialidase transition state analog inhibitors 2,3-dehydro-2-deoxy-sialic acids (Sia2ens) using the unique property of SpNanC-catalyzed reaction. Such compounds can be further derivatized at various positions and can be readily converted stereo-specifically to methyl α-sialosides as demonstrated for Neu5AcαOMe (16). Inhibition studies demonstrated improved selectivity of several Neu5Ac2en (6) derivatives with modifications at C-5 or C-9.

Example 5. Sia2en Hydration Using SpNanC

SpNanC-catalyzed hydration of Neu5Ac2en (6) was explored for the synthesis of sialoside Neu5AcαOMe (16), a high value compound that has been used to remove anti-Neu5Ac antibodies in affinity column purification of anti-Neu5Gc antibodies and a probe for binding studies. The effects of methanol in the aqueous reaction mixtures was studied. A final percentage of 20-25% methanol was found to provide a good balance of enzyme activity and product yield. As shown in Scheme 6, Neu5AcαOMe (16) was successfully synthesized with a good 65% yield in the presence of 25% methanol. The only byproduct was Neu5Ac which was readily recovered. The advantage of the method lies in its stereo-selectivity. Once bound to the active site of SpNanC, water or methanol molecule was added only from the ca-face of Neu5Ac2en (6) to form α-Neu5Ac or α-sialoside. This provides a convenient strategy of converting Neu5Ac2en byproduct formed in common chemical glycosylation reactions to a useful sialoside. Here, Neu5Ac2en serves as a novel sialylation donor.

Scheme 6.
SpNanC-catalyzed synthesis of Neu5AcαOMe from Neu5Ac2en.

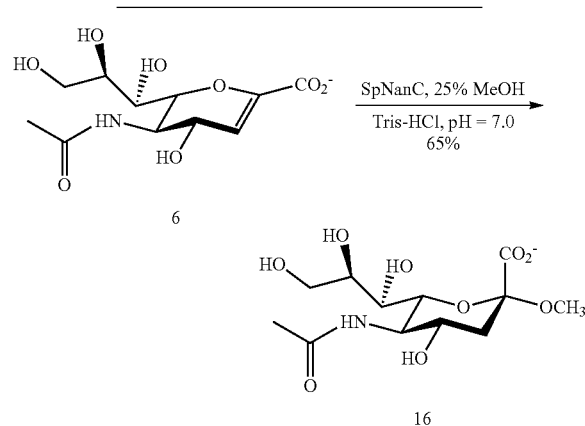

Besides the direct formation of Neu5AcαOMe from Neu5Ac2en in the presence of methanol, the hydration of Neu5Ac2en derivatives by SpNanC was also explored. This can provide the sialic acid donor which can be used in the one-pot multienzyme (OPME) synthesis of sialosides. As shown in Scheme 7, the hydration of Sia2ens by SpNanC provided the corresponding sialic acids, serving as an alternative source of sialic acids to the sialic acid aldolase-catalyzed reaction. SpNanC is an α2-3-specific sialidase, thus this strategy works extremely well for the formation of α2-6-sialosides. The enzymes can be used in a stepwise process, where the SpNanC hydration reaction is carried out and quenched once completed, after which NmCSS and α2-3-sialyltransferase are added to form α2-3-linked sialosides.

Scheme 7. SpNanC-catalyzed one-pot multienzyme (OPME) synthesis of sialosides from Sia2ens.

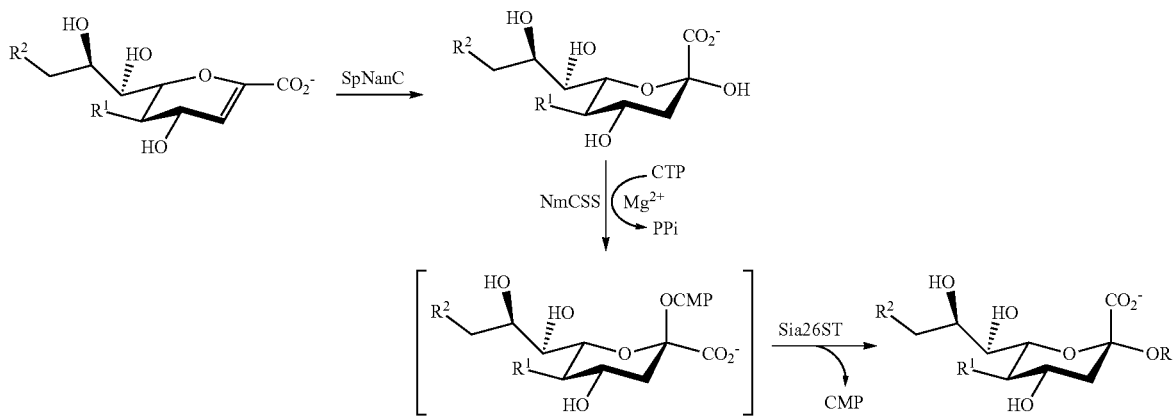

Various Sia2ens with different modifications were tested using LacβProN$_3$ as the sialylation acceptor. As shown in Table 5, Neu5Ac2en as well as its 9-modification were well tolerated by this strategy. Neu5Gc2en was not a good substrate for this reaction, due to the less efficient recognition of Neu5Gc derivatives by SpNanC. However, other 5-modified Neu5Ac2en which are recognized by SpNanC can be good substrates for this reaction.

TABLE 5

SpNanC-catalyzed one-pot multienzyme (OPME) synthesis of α2-6-sialosides from Sia2ens as the synthon.

| Substrate | Acceptor | Product | Yield estimated by TLC (18 h reaction) |
|---|---|---|---|
| Neu5Ac2en | LacβProN$_3$ | Neu5Acα2-6LacβProN$_3$ | >90% |
| Neu5Gc2en | LacβProN$_3$ | Neu5Gcα2-6LacβProN$_3$ | <10% |
| Neu5Ac9N$_3$2en | LacβProN$_3$ | Neu5Ac9N$_3$α2-6LacβProN$_3$ | >90% |
| Neu5Ac9NAc2en | LacβProN$_3$ | Neu5Ac9NAcα2-6LacβProN$_3$ | >90% |

Example 6. Preparation of 2,7-Anhydro-Sialic Acids 2,7-anhydro-sialic acids were prepared from N-acetyl-mannosamine (ManNAc), mannose, or derivatives using the synthetic scheme showed in Scheme 8.

niae (SpNanA, SpNanB, and SpNanC), *Pasteurella multocida* sialyltransferase 1 with α2-3-sialidase activity (PmST1), and *Bifidobacterium infantis* sialidase BiNanH2. Commercially available bacterial sialidases used included those from *Arthrobacter ureafaciens* (Prozyme), *Clostridium perfringens* CpNanI (Sigma-Aldrich), and

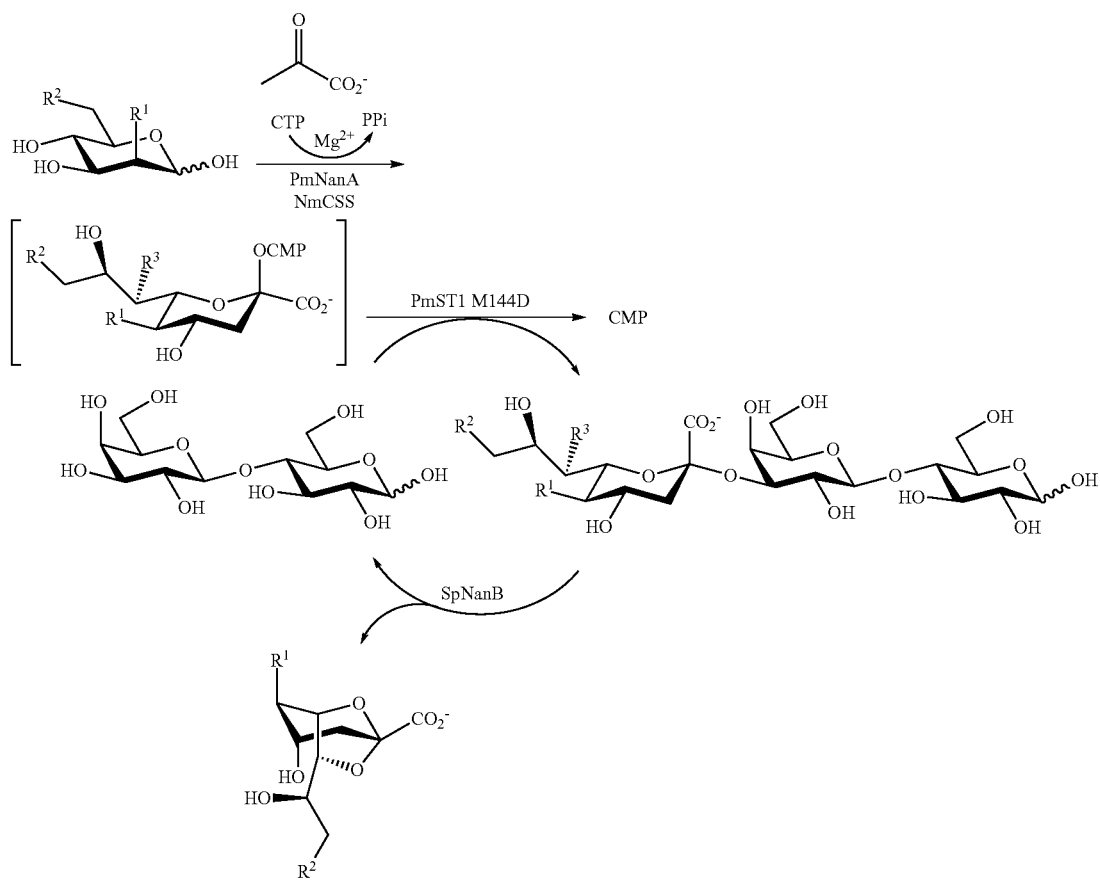

Scheme 8. SpNanB-catalyzed synthesis of 2,7-andydro-sialic acids.

$R^1$ = NHAc, NHGc, $N_3$, or Ac$N_3$, $R^2$ = OH; Yields: 60-92%

One-pot multienzyme reaction was carried out in Tris-HCl buffer solution (100 mM, pH 8.5) with N-acetylmannosamine (ManNAc), mannose, or derivatives (100 mM), sodium pyruvate (300 mM), cytidine-5′-triphosphate (CTP, 120 mM), MgCl$_2$ (20 mM), Lactose (25 mM), PmNanA (0.15 mg/mL), NmCSS (0.25 mg/mL), PmST1 M144D (0.25 mg/mL), SpNanB (0.2 mg/mL). The mixture is incubated at 37° C. for 6 h with shaking. 5 mL cold methanol was added to stop reaction, and insoluble material removed by centrifugation. Purification by Bio-Gel P-2 size exclusion column followed by normal phase Amino HILIC purification (ACN/H$_2$O) produced the desired 2,7-anhydro sialic acid or derivatives.

Example 7. Preparation of 2,7-Anhydro-Sialic Acids

Experimental Methods

Recombinant sialidases were expressed and purified as reported previously for human cytosolic sialidase hNEU2, as well as bacterial sialidases from *Streptococcus pneumoniae* (SpNanA, SpNanB, and SpNanC), *Pasteurella multocida* sialyltransferase 1 M144D mutant (PmST1_M144D) were expressed and purified as described previously. Siaα2-3GalβpNP used for substrate specificity studies were synthesized as described previously.

Nuclear Magnetic Resonance (NMR) spectra were recorded in the NMR facility of the University of California, Davis on a Bruker Avance-400 NMR spectrometer (400 MHz for $^1$H, 100 MHz for $^{13}$C). Chemical shifts are reported in parts per million (ppm) on the δ scale. High resolution electrospray ionization (ESI) mass spectra were obtained using a Thermo Electron LTQ-Orbitrap Hybrid MS at the Mass Spectrometry Facility at the University of California, Davis. Column chromatography was performed using RediSep Rf silica columns or an ODS-SM (C18) column (51 g, 50 μm, 120 Å, Yamazen) on the CombiFlash® Rf 200i system. Thin layer chromatography (TLC) was performed on silica gel plates (Sorbent Technologies) using anisaldehyde sugar stain for detection. Gel filtration chromatography was performed with a column (100 cm×2.5 cm) packed with Bio-Gel P-2 Fine resins (Bio-Rad). All reagents were at least of reagent grade and were used as supplied without further purification unless indicated.

One-Pot Multienzyme (OPME) Synthesis of 2,7-anhydro-sialic acids

ManNAc (1.0 g) or ManNTFA (300 mg), lactose (0.5 equiv.), sodium pyruvate (5 equiv.), CTP (1.5 equiv.) were dissolved in Tris-HCl buffer (100 mM, pH 7.5, 100 or 20 mL) containing 20 mM of $MgCl_2$. The pH of the solution was further adjusted to 7.5 with 4 M NaOH. PmAldolase (8.0 or 4.0 mg), NmCSS (4.0 or 2.0 mg), PmST1_M144D (8.0 or 4.0 mg), SpNanB (4.0 or 2.0 mg) were added and the reaction was incubated in an isotherm incubator for 16 h at 37° C. with agitation at 100 rpm. The reaction was quenched by adding the same volume of ice-cold ethanol and incubating at 4° C. for 1 h. The formed precipitates were removed by centrifugation and the supernatant was concentrated. The residue was purified gradually by passing it through a BioGel P-2 gel filtration column, a silica column (EtOAc:MeOH:$H_2O$=4:2:0.2, by volume), followed by a C18 column (100% $H_2O$) to produce the pure compound.

5-Acetamido-2,7-anhydro-3,5-dideoxy-α-D-glycero-D-galacto-non-2-ulopyranosonic acid (2,7-anhydro-Neu5Ac). 1.10 g, 78%, white solid. $^1H$ NMR (400 MHz, $D_2O$) δ 4.51 (bs, 1H, H-6), 4.40 (dd, J=7.8, 0.8 Hz, 1H, H-7), 3.95-3.90 (m, 1H, H-4), 3.89 (bs, 1H, H-5), 3.72 (dd, J=11.8, 2.8 Hz, 1H, H-9), 3.56 (dd, J=11.8, 6.0 Hz, 1H, H-9'), 3.50 (ddd, J=7.8, 6.0, 2.8 Hz, 1H, H-8), 2.14 (dd, J=15.2, 5.6 Hz, 1H, H-3ax), 2.00 (s, 3H, $COCH_3$), 2.00-1.92 (m, 1H, H-3eq); $^{13}C$ NMR (100 MHz, $D_2O$) δ 174.03, 173.51, 105.53, 77.12, 76.59, 71.91, 66.79, 62.23, 51.92, 35.25, 21.75; HRMS (ESI) Anal. Calcd for $C_{11}H_{16}NO_8$ [M-H]$^-$: 290.0881, Found: 290.0886.

2,7-Anhydro-3,5-dideoxy-5-trifluoroacetamido-α-D-glycero-D-galacto-non-2-ulopyranosonic acid (2,7-anhydro-Neu5TFA). 219.8 mg, 55%, white solid. $^1H$ NMR (400 MHz, $D_2O$) δ 4.65 (bs, 1H, H-6), 4.48 (dd, J=7.8, 0.8 Hz, 1H, H-7), 4.07-4.04 (m, 2H, H-4, H-5), 3.78 (dd, J=11.6, 2.8 Hz, 1H, H-9), 3.62 (dd, J=11.6, 6.2 Hz, 1H, H-9'), 3.57 (ddd, J=7.8, 6.2, 2.8 Hz, 1H, H-8), 2.24 (dd, J=15.2, 5.4 Hz, 1H, H-3ax), 2.05 (d, J=15.2 Hz, 1H, H-3eq); $^{13}C$ NMR (100 MHz, $D_2O$) δ 173.91, 158.47 (q, J=38.0 Hz), 115.71 (q, J=284.0 Hz), 105.57, 76.82, 76.47, 71.87, 66.14, 62.24, 52.96, 35.39; HRMS (ESI) Anal. Calcd for $C_{11}H_{16}NO_9$ [M-H]$^-$: 344.0599, Found: 344.0591.

Chemical derivatization at C-5 of 2,7-anhydro-sialic acids: 5-Amino-2,7-anhydro-3,5-dideoxy-α-D-glycero-D-galacto-non-2-ulopyranosonic acid (2,7-anhydro-Neu)

2,7-Anhydro-NeuSTFA (30.0 mg, 0.0817 mmol) was dissolved in $Na_2CO_3$ aqueous solution (2 mL, pH=9) and the reaction was stirred for 16 h. Without neutralization, the solution was directly passed through a BioGel P-2 gel filtration column to produce 2,7-Anhydro-Neu (20.1 mg, 99%) as white solid. $^1H$ NMR (400 MHz, $D_2O$) δ 4.60 (bs, 1H, H-6), 4.42 (dd, 1H, J=7.8, 0.6 Hz, H-7), 4.09-4.02 (m, 1H, H-4), 3.77 (dd, J=11.6, 2.8 Hz, 1H, H-9), 3.61 (dd, J=11.6, 6.0 Hz, 1H, H-9'), 3.56 (ddd, J=7.8, 6.0, 2.8 Hz, 1H, H-8), 3.16 (bs, 1H, H-5), 2.26 (dd, J=15.4, 5.6 Hz, 1H, H-3ax), 2.04 (d, J=15.4 Hz, 1H, H-3eq); $^{13}C$ NMR (100 MHz, $D_2O$) δ 173.86, 105.70, 77.56, 76.58, 71.90, 67.26, 62.25, 52.76, 34.84; HRMS (ESI) Anal. Calcd for $C_{11}H_{16}NO_9$ [M-H]$^-$: 248.0776, Found: 248.0771.

2,7-Anhydro-5-cyclohexylamido-3,5-dideoxy-⟨-D-glycero-D-galacto-non-2-ulopyranosonic acid (2,7-anhydro-NeuScyclohexyl)

To a stirred solution of 2,7-anhydro-Neu (15.0 mg, 0.0602 mmol) in a mixed solvent of DMF/$H_2O$/AcOH (7:2:1, 2 mL), cyclohexanone (62 µL, 0.60 mmol) and $NaBH_3CN$ (38 mg, 0.60 mmol) were added and the reaction was stirred for 30 min. The solvent was concentrated in vacuo. The crude product was re-dissolved in water (1 mL) and was passed through a BioGel P-2 gel filtration column to produce 2,7-anhydro-NeuScyclohexyl (20.8 mg, 98%) as white solid. $^1H$ NMR (400 MHz, $D_2O$) δ 4.77 (bs, 1H, H-6), 4.45 (d, J=7.6 Hz, 1H, H-7), 4.23-4.16 (m, 1H, H-4), 3.77 (dd, J=11.8, 2.8 Hz, 1H, H-9), 3.62 (dd, J=11.8, 5.8 Hz, 1H, H-9'), 3.57 (ddd, J=7.6, 5.8, 2.8 Hz, 1H, H-8), 3.36 (bs, 1H, H-5), 3.21 (bs, 1H, H-1' hexyl), 2.29 (dd, J=15.4, 5.8 Hz, 1H, H-3ax), 2.17-1.98 (m, 3H, H-3eq, H hexyl), 1.93-1.77 (m, 2H, H hexyl), 1.75-1.61 (m, 1H, H hexyl), 1.45-1.24 (m, 4H, H hexyl), 1.25-1.09 (m, 1H, H hexyl); $^{13}C$ NMR (100 MHz, $D_2O$) δ 173.54, 105.64, 76.73, 75.25, 71.80, 64.39, 62.21, 56.02, 55.52, 35.33, 29.97, 29.69, 24.70, 24.19, 24.15; HRMS (ESI) Anal. Calcd for $C_{11}H_{16}NO_9$ [M-H]$^-$: 330.1558, Found: 330.1559.

Sialidase Inhibition Assays.

Inhibition assays were carried out in duplicates in 384-well plates in a final volume of 20 µL containing Neu5Acα2-3GalβpNP (0.3 mM) and β-galactosidase (12 µg) with or without inhibitors. The assay conditions varied for different sialidases as described below: SpNanA (0.0015 µg), NaOAc buffer (100 mM, pH 6.0); SpNanB (0.003 µg), NaOAc buffer (100 mM pH 6.0); SpNanC (0.01 µg), MES buffer (100 mM, pH 6.5); AuSialidase (1.0 mU), NaOAc buffer (100 mM, pH 5.5); CpNanI (1.3 mU), MES buffer (100 mM, pH 5.0); VcSialidase (0.57 mU), NaCl (150 mM), $CaCl_2$) (10 mM), NaOAc buffer (100 mM, pH 5.5); PmST1 (0.4 µg), CMP (0.4 mM), NaOAc buffer (100 mM, pH 5.5); BiNanH2 (0.029 µg), NaOAc buffer (100 mM, pH 5.0); hNEU2 (1.2 µg), MES buffer (100 mM, pH 5.0). The reactions were incubated for 30 min at 37° C., and were stopped by adding CAPS buffer (N-cyclohexyl-3-aminopropane sulfonic acid, 40 µL, 0.5 M, pH 10.5). The amount of the para-nitrophenolate formed was determined by measuring the $A_{405\ nm}$ of the reaction mixtures using a microplate reader.

The percentage inhibitions were determined using a concentration of 1 mM of each inhibitor, with reactions without inhibitors as controls. $IC_{50}$ values were obtained by varying the concentrations of inhibitors from 0 to 1000 µM to get the concentration-response plots of the inhibitors. The values of $IC_{50}$ were calculated by the software Grafit 5.0.

Results

One-Pot Multienzyme (OPME) Synthesis of 2,7-anhydro-sialic acids

SpNanB was able to catalyze the formation of 2,7-anhydro-Neu5Ac directly from Neu5Ac, similar to the function of leech IT trans-sialidase NanL. The new strategy for synthesis of 2,7-anhydro-Neu5Ac (2-1) therefore started with directly treating N-acetylneuraminic acid (Neu5Ac) with SpNanB. However, among various conditions of different buffers and SpNanB concentrations less than 20% conversion at most was observed based on thin-layer chromatography (TLC) analysis, which was not satisfying for preparative scale synthesis. A more sophisticated one-pot multienzyme (OPME) system was then developed for the synthesis of 2,7-anhydro-sialic acids, resembling the OPME strategy developed for the synthesis of Sia2ens. The difference is that the core enzyme SpNanC in the previous system was replaced by SpNanB.

sialosides were good substrates for SpNanB. The α2-3-linked sialosides bearing C5- and C9-modified Neu5Ac were well tolerated. Sialosides containing N-glycolylneuraminic acid (Neu5Gc), as well as its 9-modifications, were also tolerated by SpNanB. However, Kdn derivatives were generally not accepted.

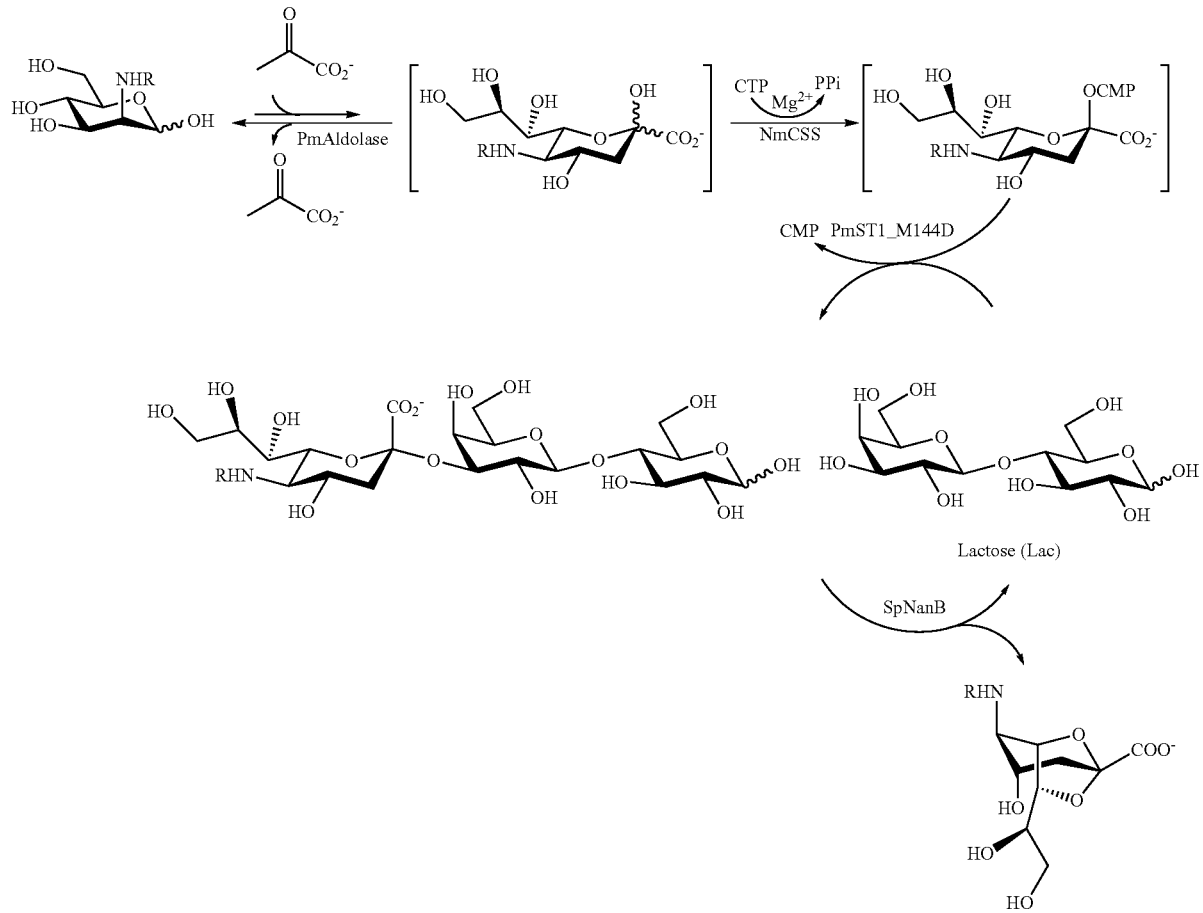

Scheme 9. One-pot multienzyme (OPME) synthesis of 2,7-anhydro-sialic acids.

ManNAc (M1) & 2,7-anhydro-Neu5Ac (2-1): R = Ac, 78% yield.
ManNTFA (M2) & 2,7-anhydro-Neu5TFA (2-2): R = TFA, 55% yield.

As shown in Scheme 9, four enzymes were involved in the reactions including *Pasteurella multocida* sialic acid aldolase (PmAldolase), *Neisseria meningitidis* CMP-sialic acid synthetase (NmCSS), *Pasteurella multocida* sialyltransferase 1 M144D mutant (PmST1_M144D), and SpNanB, which produced the target product. In this one-pot reaction, the α2-3-sialyllactose formed by the sialoside formation reaction catalyzed by the first three enzymes provided a suitable substrate for SpNanB to form the desired product. The optimized condition provided 2,7-anhydro-Neu5Ac (2-1) in gram scale with 78% yield. The new method showed significant advantages compared to previously known chemical or enzymatic synthetic procedures.

Substrate Specificity of SpNanB.

Next, a library of para-nitrophenol (pNP)-tagged α2-3-linked sialosides with modifications on different positions were screened to explore the substrate specificity of SpNanB, to test the compatibility of the OPME synthesis for different derivatives (Table 6). None of the α2-6-linked Results for the substrate specificity of SpNanB indicated that C7-modified sialic acids were also good substrates for SpNanB. Because the hydroxyl group on C-7 is the nucleophile which attacks the anomeric carbon of sialic acid during the intramolecular trans-sialidase-catalyzed step, this was an unexpected result. Neu5Ac7N$_3$-α2-3-GalβpNP, one of the 7-modified sialosides, was tested to confirm the reaction and characterize the product formed. Thin layer chromatography (TLC) showed only two product spots throughout the reaction process, one of which represented GalβpNP. Mass spectroscopy showed a m/z value of 333.1051, corresponded to 7-azido-Neu5Ac (7N$_3$Neu5Ac). Monitoring the reaction by NMR also confirmed Neu5Ac7N$_3$ as the product. This indicates that in the case of substrates baring 7-modified sialic acids, SpNanB can catalyze the hydrolysis of 7-modified sialosides directly in the absence of a 7-OH required for intramolecular trans-sialidase reaction.

TABLE 6

Substrate specificity of SpNanB.

| Substrate | Recognition |
|---|---|
| Neu5Acα2-3GalβpNP | + |
| Neu5AcFα2-3GalβpNP | + |
| Neu5AcOMeα2-3GalβpNP | + |
| Neu5AcN₃α2-3GalβpNP | + |
| Neu5Ac9Fα2-3GalβpNP | + |
| Neu5Ac9OMeα2-3GalβpNP | + |
| Neu5Ac9deoxyα2-3GalβpNP | + |
| Neu5Ac7Fα2-3GalβpNP | + |
| Neu5Ac7OMeα2-3GalβpNP | + |
| Neu5Ac7deoxyα2-3GalβpNP | + |
| Neu5Ac7N₃α2-3GalβpNP | + |
| Neu5Gcα2-3GalβpNP | + |
| Neu5Gc9Fα2-3GalβpNP | + |
| Neu5Gc9OMeα2-3GalβpNP | + |
| Neu5Gc9deoxyα2-3GalβpNP | + |
| Neu5Gc9N₃α2-3GalβpNP | + |
| Kdnα2-3GalβpNP | − |
| Kdn5Fα2-3GalβpNP | − |
| Kdn5N₃α2-3GalβpNP | − |
| Kdn5deoxyα2-3GalβpNP | − |
| Kdn5OMeα2-3GalβpNP | − |
| Kdn9Fα2-3GalβpNP | − |
| Kdn9OMeα2-3GalβpNP | − |
| Kdn7Fα2-3GalβpNP | − |
| Kdn7OMeα2-3GalβpNP | − |
| Kdn7deoxyα2-3GalβpNP | − |
| Kdn7N₃α2-3GalβpNP | − |

+ represents >80% conversion; − represents <20% conversion.

Synthesis of 2,7-anhydro-sialic acid Derivatives as Sialidase Inhibitors

The substrate promiscuities of SpNanB and other enzymes involved in the OPME synthesis made this method compatible with most 2,7-anhydro-sialic acid derivatives baring modifications on C-5 and C-9, except for Kdn derivatives. 2,7-anhydro-Neu5TFA (2-2) was synthesized in 55% yield, which was a suitable substrate for further chemical derivatization to produce the target product 2,7-anhydro-Neu5cyclohexyl (2-4). The lower yield compared to the yield of 2,7-anhydro-Neu5Ac was due to the lability of the trifluoroacetyl group. The trifluoroacetyl group was readily removed under mild basic condition to produce 2,7-anhydro-Neu (2-3) as the intermediate. The resulted amino group was coupled with the designed cyclohexyl group by reductive amination in almost quantitative yield.

Scheme 10.
Synthesis of 2,7-anhydro-Neu5cyclohexyl (4) from 2,7-anhydro-Neu5TFA.

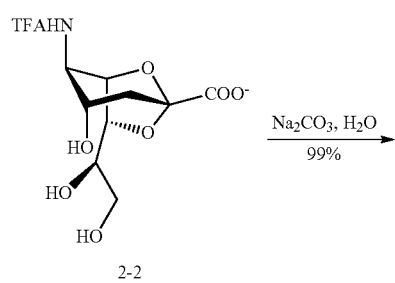

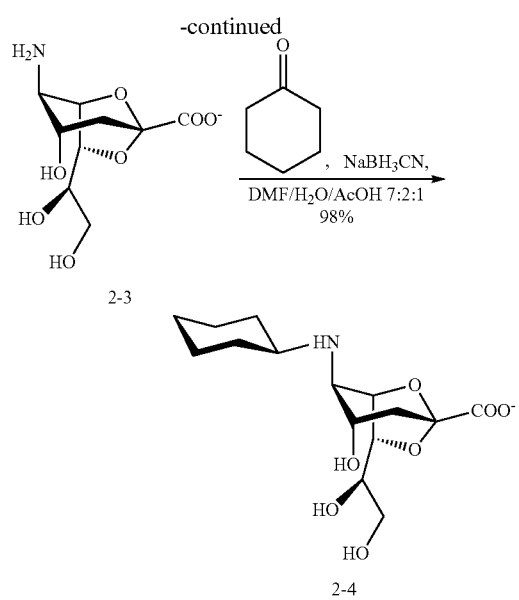

It was previously reported that SpNanB, similar to the leech intramolecular trans-sialidase, could have 2,7-anhydro-Neu5Ac hydrolysis activity (see, Xu, et al. J. Mol. Biol. 2008, 384, 436-449). In that report, the NMR time course study of product-release by SpNanB showed the presence of Neu5Ac after 24 h, but 2,7-anhydro-Neu5Ac was still the dominant product after 48 h. However, this 2,7-anhydro-Neu5Ac hydrolysis hypothesis was never directly confirmed by followed up experiments, probably due to the limited access of the 2,7-anhydro-Neu5Ac substrate. We confirmed the 2,7-anhydro-Neu5Ac hydrolysis activity of SpNanB by directly treating 2,7-anhydro-Neu5Ac with SpNanB. In the presence of SpNanB (1.0 mg/mL), 2,7-anhydro-Neu5Ac could be converted to Neu5Ac in an estimated yield of 80% based on TLC after incubating in 37° C. for 24 h. Therefore, SpNanB catalyzes the formation of 2,7-anhydro-sialic acid which can be hydrolyzed slowly by SpNanB to form sialic acid.

The 2,7-anhydro-Neu5Ac hydrolysis activity of SpNanB is a concern since SpNanB might hydrolyze the 2,7-anhydro-Neu5cyclohexyl inhibitor. Advantageously, no hydrolysis activity was observed when 2,7-anhydro-Neu5cyclohexyl was incubated with SpNanB under the same condition used for the hydrolysis of 2,7-anhydro-Neu5Ac.

Sialidase Inhibition Study.

The designed inhibitor 2,7-anhydro-Neu5cyclohexyl (2-4), along with other 2,7-anhydro-sialic acids (2-1, 2-2, and 2-3), were tested for their inhibition activities against several glycoside hydrolase GH33 family sialidases categorized in the Carbohydrate Active Enzyme (CAZy) database. The bacterial sialidases tested include recombinant sialidases cloned from Streptococcus pneumoniae (SpNanA, SpNanB, and SpNanC), Pasteurella multocida sialyltransferase with α2-3-sialidase activity (PmST1), Bifidobacterium infantis sialidase BiNanH2, as well as commercially available sialidases from Arthrobacter ureafaciens (AuSialidase), Clostridium perfringens (CpNanI), and Vibrio cholerae (VcSialidase). Recombinant human cytosolic sialidase hNEU2 was also tested.

Inhibition studies were carried out using Neu5Acα2-3GalβpNP as the sialidase substrate. The 2,7-anhydro-sialic acids, along with Neu5Ac2en as a reference, were screened under a concentration of 1 mM to test whether they were effective inhibitors against these bacterial and human sialidases. As shown in Table 7, 2,7-anhydro-Neu5Ac (2-1) and 2,7-anhydro-Neu (2-3) were not effective inhibitors against all the sialidases tested. Advantageously, 2,7-anhydro-Neu5cyclohexyl (2-4) did show effective inhibitory activity against SpNanB, as well as weak inhibition against SpNanA. Quite interestingly, 2,7-anhydro-Neu5cyclohexyl (2-4) also showed inhibition against SpNanC. 2,7-anhydro-Neu5TFA (2-2), the intermediate designed for the synthesis of 2,7-anhydro-Neu5cyclohexyl, also showed moderate inhibitory activity against SpNanA, AuSialidase, and weak inhibition against SpNanB and VcSialidase.

TABLE 7

Percentage inhibition (%) of 2,7-anhydro-sialic acids (1-4) (1 mM of each inhibitor was used) against bacterial and human sialidases.

| Sialidases | Inhibitors | | | | |
|---|---|---|---|---|---|
| | Neu5Ac2en | (2-1) | (2-2) | (2-3) | (2-4) |
| SpNanA | 98.9 ± 1.8 | 36.4 ± 0.1 | 83.8 ± 0.3 | 19.3 ± 4.2 | 61.2 ± 0.6 |
| SpNanB | 26.1 ± 1.0 | 30.0 ± 1.7 | 68.2 ± 2.6 | 11.7 ± 2.6 | 86.6 ± 0.3 |
| SpNanC | 9.0 ± 3.5 | 3.0 ± 1.9 | 4.4 ± 2.0 | 14.9 ± 3.0 | 94.2 ± 0.1 |
| AuSialidase | 99.6 ± 0.6 | 49.4 ± 1.3 | 85.1 ± 0.3 | 1.3 ± 2.2 | 16.8 ± 2.4 |
| CpNanI | 93.3 ± 3.8 | 26.7 ± 3.7 | 44.1 ± 1.0 | 10.1 ± 5.7 | 13.6 ± 0.1 |
| VcSialidase | 98.8 ± 0.1 | 22.7 ± 1.2 | 62.1 ± 0.6 | 1.3 ± 2.0 | 1.2 ± 0.7 |
| PmST1 | 15.8 ± 0.1 | 10.2 ± 2.8 | 11.0 ± 2.7 | 13.8 ± 3.3 | 12.3 ± 1.9 |
| BiNanH2 | 95.3 ± 0.2 | 6.6 ± 1.8 | 3.8 ± 2.6 | 3.2 ± 3.2 | 1.2 ± 0.9 |
| hNEU2 | 99.8 ± 0.2 | 4.6 ± 1.1 | 2.5 ± 2.1 | 1.4 ± 2.4 | 3.6 ± 0.1 |

For inhibitors with more than 50% inhibitory activity against certain sialidases at 1 mM concentration, $IC_{50}$ values were obtained (Table 8). 2,7-Anhydro-Neu5cyclohexyl (2-4) was an inhibitor with weak inhibition against SpNanB ($IC_{50}$=180±23 μM), and moderate inhibition against SpNanC ($IC_{50}$=58.4±2.4 μM). 2,7-Anhydro-Neu5TFA (2) showed weak inhibition against SpNanA ($IC_{50}$=145±16 μM) and AuSialidase ($IC_{50}$=225±34 μM).

TABLE 8

$IC_{50}$ Values of 2,7-anhydro-Neu5TFA (2-2) and 2,7-anhydro-Neu5cyclohexyl (2-4) against Bacterial Sialidases SpNanA, SpNanB, SpNanC, AuSialidase, and VcSialidase.

| Sialidases | $IC_{50}$ values of different inhibitors (μM) | |
|---|---|---|
| | (2-2) | (2-4) |
| SpNanA | 145 ± 16 | 500-1000 |
| SpNanB | 250-500 | 180 ± 23 |
| SpNanC | >1000 | 58.4 ± 2.4 |
| AuSialidase | 225 ± 34 | >1000 |
| VcSialidase | 500-1000 | >1000 |

A novel one-pot multienzyme (OPME) strategy was developed for preparative and gram-scale synthesis of 2,7-anhydro-sialic acids. These 2,7-anhydro-sialic acids were screened as sialidase inhibitors. The rationally designed inhibitor 2,7-anhydro-Neu5cyclohexyl (2-4) showed inhibition against both SpNanB and SpNanC. This study demonstrated a new idea of exploring the family of 2,7-anhydro-sialic acids as sialidase inhibitors.

Example 8. Large-Scale 2-Step Preparation of 2,7-Anhydro-Sialic Acids

The one-pot multienzyme (OPME) procedures allow the production of 2,3-dehydro-2-deoxy-sialic acids (Sia2ens) and 2,7-anhydro-sialic acids directly from Neu5Ac, ManNAc, or derivatives and the use of only catalytic amount of the acceptor (e.g. lactose). However, the purification procedures for certain products were found to be tedious and multiple column purification processes may be necessary to obtain pure compounds in some cases. In order to simplify the product purification procedures, an improved two-step OPME procedure has been developed. In this strategy, a hydrophobic chromophore or fluorophore is attached to the acceptor to allow easy purification by C18-cartridge or C18-columns. Both carboxybenzyl (Cbz)-protected propyl amine and fluorenylmethyloxycarbonyl (Fmoc)-protected propyl amine were tested as the tag for the acceptor (e.g., lactosides) and both worked well. Cbz protecting group is particularly stable during the reaction and purification processes and was chosen for the large-scale production of 2,7-anhydro-Neu5Ac. The synthesis of other 2,7-anhydro-sialic acids and 2,3-dehydro-2-deoxy-sialic acids (Sia2ens) can be performed similarly.

Scheme 11. Two-step one-pot multienzyme (OPME) production of 2,7-anhydro-Neu5Ac (1) from Neu5Ac (2).

Step 1.

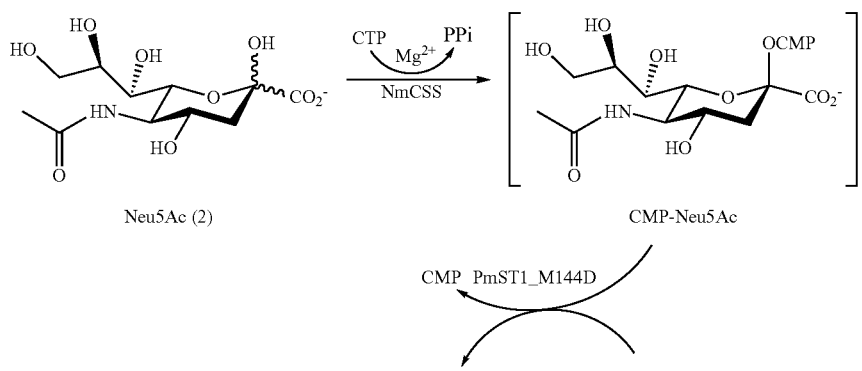

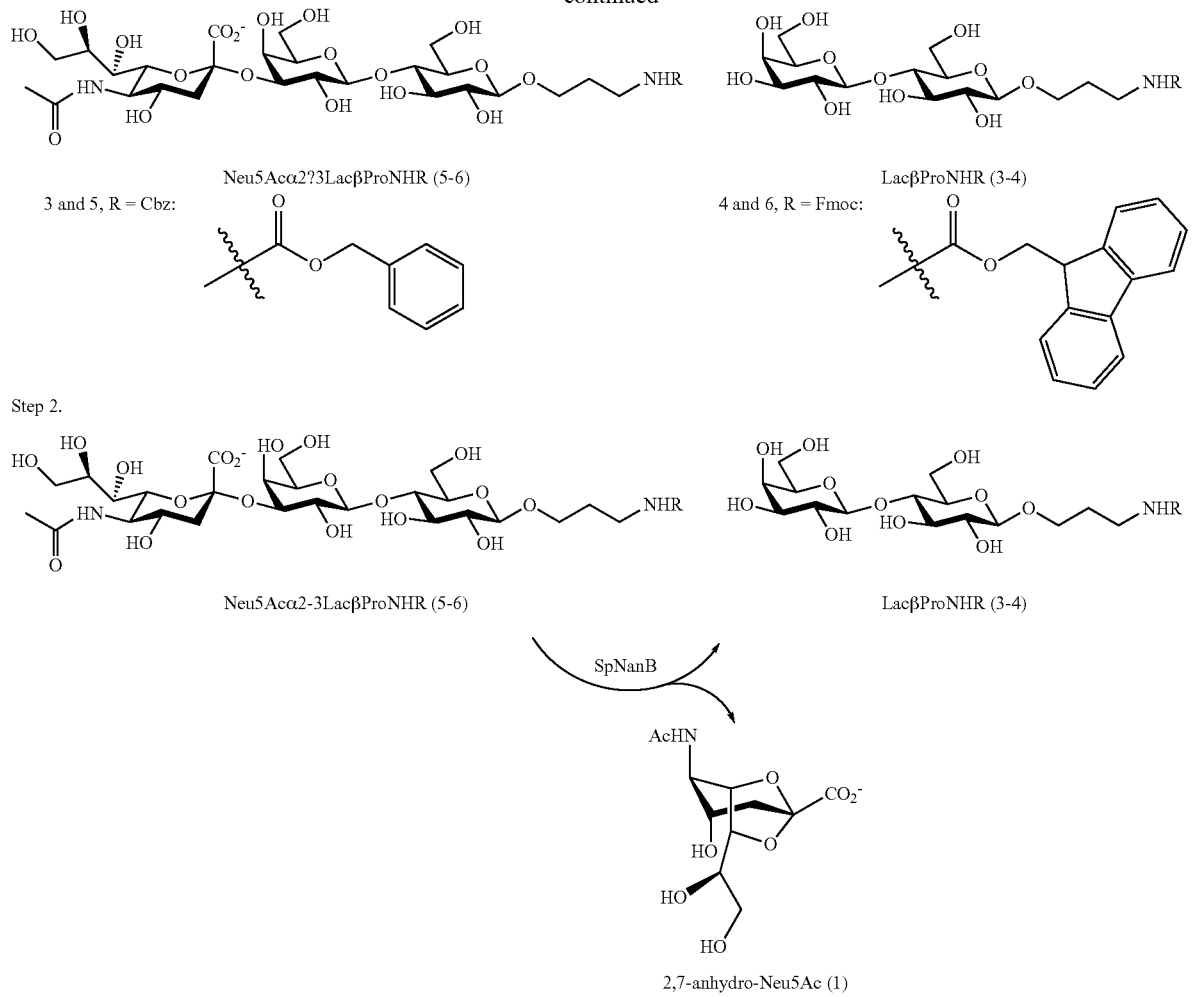

As shown in Scheme 11, two enzymes are involved in first step for one-pot multienzyme (OPME) high-yield synthesis of α2-3-linked sialosides (Neu5Acα2-3LacβProNHCbz 5 and Neu5Ac(α2-3LacβProNHFmoc 6) from the corresponding lactosides (LacβProNHCbz 3 and LacβProNHFmoc 4). In the second step, the α2-3-linked sialosides (Neu5Acα2-3LacβProNHCbz 5 and Neu5Acα2-3LacβProNHFmoc 6) can be used in SpNanB-catalyzed reaction for the formation of desired 2,7-anhydro-Neu5Ac (1) in high yields. In the first step, both sialoside product and lactoside can be readily separated from each other and from other components of the enzymatic reaction by passing a C18-cartridge. In the second step, 2,7-anhydro-Neu5Ac (1) is readily eluted from the C18-cartridge to obtain pure product. The remaining sialoside starting material and lactoside product can be readily purified and reused in step 1 or step 2 of the next round of the reaction. Each round of reactions (step 1+step 2) efficiently convert Neu5Ac and CTP to 2,7-anhydro-Neu5Ac (1), CMP, and pyrophosphate (PPi) while both lactoside and sialoside are recycled.

The two-step synthesis scheme can be repeated multiple time in large scales (e.g., gram-scale), and each time produces pure 2,7-anhydro-Neu5Ac (1) with easy purification procedures.

Three experiments were performed to demonstrate the efficiency of the method with lactoside LacβProNHCbz 3 as the sialyltransferase acceptor. Experiments 1 and 2 shown below use a slight excess of Neu5Ac while Experiment 3 uses a slight excess of lactoside.

Materials.

All chemicals were obtained from commercial suppliers and used without further purification. $^1$H NMR (400 or 800 MHz) and $^{13}$C NMR (400 or 800 MHz) spectra were recorded on a Bruker Avance-400 Spectrometer (400 MHz for $^1$H, 100 MHz for $^{13}$C) or a Avance-800 Spectrometer (800 MHz for $^1$H, 200 MHz for $^{13}$C). High resolution electrospray ionization (ESI) mass spectra were obtained using a Thermo Electron LTQ-Orbitrap Hybrid MS at the Mass Spectrometry Facility in the University of California, Davis. Column chromatography was performed using RediSep Rf silica columns or an ODS-SM column (51 g, 50 μm, 120 Å, Yamazen) on the CombiFlash® Rf 200i system. Analytical thin-layer chromatography was performed on silica gel plates 60 $GF_{254}$ (Sorbent technologies) using anisaldehyde stain for detection. Recombinant NmCSS, PmST1_M144D and SpNanB were expressed as described previously.

Experiment 1

Step 1: One-pot two-enzyme synthesis of Neu5Acα2-3LacβProNHCbz (5) using an excess of Neu5Ac.

LacβProNHCbz (3) (1 g, 1.87 mM) and Neu5Ac (1.1 equiv. 0.68 g, 2.06 mM) were incubated at 30° C. with agitation at 120 rpm in Tris-HCl buffer (100 mM, pH=8.5) containing CTP (1.2 equiv.), $MgCl_2$ (20 mM), and an appropriate amount of NmCSS (5 mg) and PmST1M144D (12 mg). The reaction was monitored by thin-layer chromatography (TLC) using developing solvent consisting of EtOAc: MeOH:$H_2$O=5:2:1 (by volume) and the TLC plates were stained with ap-anisaldehyde sugar stain. After 4-6 h, the reaction was quenched by adding the same volume of pre-chilled ethanol and the reaction mixture was centrifuged to remove precipitates. The supernatant was concentrated and passed through a C18 column ($H_2$O:$CH_3$CN=1:0-4:1) to obtain Neu5Acα2-3LacβProNHCbz (5, 1.46 g), which would be used in the following reaction to produce 2,7-anhydro-Neu5Ac (1). The isolated yield was 95%. The remaining LacβProNHCbz (3) can be recycled and used for next round of sialylation reaction.

Step 2: Formation of 2,7-anhydro-Neu5Ac (7) from Neu5Acα2-3LacβProNHCbz (5) by SpNanB-catalyzed reaction. Neu5Acα2-3LacβProNHCbz (5, 1.46 g, 1.77 mM) was incubated at 30° C. in ammonia formate buffer (100 mM, pH=5.5) containing an appropriate amount of SpNanB (5 mg). The reaction was monitored by thin-layer chromatography (TLC) using developing solvent consisting of EtOAc:MeOH:$H_2$O=5:2:1 (by volume) and the TLC plates were stained with ap-anisaldehyde sugar stain. After 4 h, the reaction was quenched by adding the same volume of pre-chilled ethanol and the reaction mixture was centrifuged to remove precipitates. The supernatant was concentrated and passed through a C18 column ($H_2$O:$CH_3$CN=1:0-2:1) to obtain pure 2,7-anhydro-Neu5Ac (1) (0.47 g, 1.63 mM, yield=92%), LacβProNHCbz (3) (870 mg) and Neu5Acα2-3LacβProNHCbz (117 mg). Ammonia formate buffer eluted out together with anhydro-Neu5Ac (1) could be removed easily by applying vacuum. LacβProNHCbz (3) (870 mg, yield=92%) and Neu5Acα2-3LacβProNHCbz (5, 117 mg) can be recovered and reused in the next cycle of two-step one-pot multienzyme (OPME) production of 2,7-anhydro-Neu5Ac (1) from Neu5Ac (2).

Experiment 2. Synthetic Cycle for Two-Step, One-Pot Multienzyme (OPME) Production of 2,7-anhydro-Neu5Ac Step 1. After the first 2-step one-pot multienzyme (OPME) cycle was complete, the recovered LacβProNHCbz (3) (870 mg, 1.63 mM) was used in the one-pot two-enzyme synthesis of Neu5Acα2-3LacβProNHCbz (5, 1.28 g, 1.55 mM) with 95% yield, which combined with 117 mg Neu5Acα2-3LacβProNHCbz (5) recycled from Experiment 1 totaled 1.38 g.

Step 2. Neu5Acα2-3LacβProNHCbz (5, 1.38 g, 1.68 mM) was used in a SpNanB-catalyzed reaction for the formation of 2,7-anhydro-Neu5Ac (1, 450 mg) and LacβProNHCbz (3, 820 mg). A yield of 92% was obtained for the production of the desired target 2,7-anhydro-Neu5Ac (1). The remaining unreacted Neu5Acα2-3LacβProNHCbz (5, 110 mg, 7%) was then recycled. After 2 cycles of reactions, a total of 920 mg of 2,7-anhydro-Neu5Ac (1) was formed. At the same time, 820 mg of LacβProNHCbz (3) and 110 mg of Neu5Acα2-3LacβProNHCbz (5) were recovered so that the 2-step OPME synthesis of 2,7-anhydro-Neu5Ac (1) could be repeated.

Experiment 3

Step 1: One-pot two-enzyme synthesis of Neu5Acα2-3LacβProNHCbz (5) using a slightly excess amount of lactoside LacβProNHCbz (3). LacβProNHCbz (3) (1.0 equiv. 800 mg, 1.50 mM) and Neu5Ac (2) (0.95 equiv. 471 mg, 1.42 mM) were incubated at 30° C. with an agitation at 120 rpm in Tris-HCl buffer (100 mM, pH=8.5) containing CTP (1.1 equiv.), $MgCl_2$ (20 mM) and an appropriate amount of NmCSS (5 mg) and PmST1M144D (12 mg). The reaction was monitored by thin-layer chromatography (TLC) using developing solvent consisting of EtOAc: MeOH:$H_2$O=5:2:1 (by volume) stained with ap-anisaldehyde sugar stain and high-resolution electrospray ionization (ESI) mass spectra (HRMS). After 4 h, the mass spectra showed nearly complete consumption of Neu5Ac (2) or CMP-Neu5Ac, the reaction was quenched by adding the same volume of pre-chilled ethanol and the reaction mixture was centrifuged to remove precipitates. The supernatant was concentrated and passed through a C18 column with isocratic flow ($H_2$O:ACN=1:0, 85:15, and 4:1) to obtain Neu5Acα2-3LacβProNHCbz (5, 1.17 g, separation yield=96%) and remaining LacβProNHCbz (3). Neu5Acα2-3LacβProNHCbz (5) was eluted at 15% ACN and LacβProNHCbz (3) was eluted from the column at 20% ACN. One of the advantages of this one-pot two-enzyme synthesis of Neu5Acα2-3LacβProNHCbz (5) is that Neu5Ac (2) is efficiently converted to Neu5Acα2-3LacβProNHCbz (5), and the excess LacβProNHCbz (3) can be recovered and reused. Neu5Acα2-3LacβProNHCbz (5) can be used in the second step to produce 2,7-anhydro-Neu5Ac (1).

Step 2. Formation of 2,7-anhydro-Neu5Ac (7) from Neu5Acα2-3LacβProNHCbz (5) by SpNanB-catalyzed reaction. Neu5Acα2-3LacβProNHCbz (5, 1.46 g, 1.77 mM) was incubated at 30° C. in ammonia formate buffer (100 mM, pH=5.5) containing an appropriate amount of SpNanB (5 mg). The reaction was monitored by thin-layer chromatography (TLC) using developing solvent consisting of EtOAc:MeOH:$H_2$O=5:2:1 (by volume) and the TLC plates were stained with ap-anisaldehyde sugar stain. After 4 h, the reaction was quenched by adding the same volume of pre-chilled ethanol and the reaction mixture was centrifuged to remove precipitates. The supernatant was concentrated and passed through a C18 column with isocratic flow ($H_2$O:ACN=1:0, 85:15, and 4:1) to obtain pure 2,7-anhydro-Neu5Ac (1) (0.47 g, 1.63 mM, yield=92%), LacβProNHCbz (3) (870 mg), and Neu5Acα2-3LacβProNHCbz (117 mg). 2,7-anhydro-Neu5Ac (1) was eluted at 100% $H_2$O, Neu5Acα2-3LacβProNHCbz (5) was eluted at 15% ACN and LacβProNHCbz (3) was eluted at 20% ACN. Ammonium formate buffer eluted together with anhydro-Neu5Ac (1) and was readily removed by applying vacuum. LacβProNHCbz (3) (870 mg, yield=92%) and Neu5Acα2-3LacβProNHCbz (5, 117 mg) were recovered for reuse in subsequent cycles of the two-step one-pot multienzyme (OPME) procedure.

VII. Exemplary Embodiments

Exemplary embodiments provided in accordance with the presently disclosed subject matter include, but are not limited to, the claims and the following embodiments:

1. A method for forming a sialic acid product selected from the group consisting of a 2-deoxy-2,3-dehydro-sialic acid, a 2,7-anhydro-sialic acid, and derivatives thereof, the method comprising:
    forming a reaction mixture comprising a glycoside acceptor, a sialic acid donor, and a sialyltransferase;
    maintaining the reaction mixture under conditions sufficient to form a sialoside; and contacting the sialoside with a *Streptococcus pneumoniae* sialidase to form the sialic acid product.

2. The method of embodiment 1, wherein the sialic acid product is a 2-deoxy-2,3-dehydro-sialic acid or a derivative thereof.

3. The method of embodiment 2, wherein the *Streptococcus pneumoniae* sialidase is SpNanC having the amino acid sequence set forth in SEQ ID NO:1, or a catalytically active variant thereof.

4. The method of embodiment 3, wherein the SpNanC is *S. pneumoniae* TIGR4 SpNanC having the amino acid sequence set forth in SEQ ID NO:2, or a catalytically active variant thereof.

5. The method of embodiment 1, wherein the sialic acid product is a 2,7-anhydro-sialic acid or a derivative thereof.

6. The method of embodiment 5, wherein the *Streptococcus pneumoniae* sialidase is SpNanB having the amino acid sequence set forth in SEQ ID NO:3, or a catalytically active variant thereof.

7. The method of any one of embodiments 1-6, wherein the sialoside is an α2-3-linked sialoside or a derivative thereof.

8. The method of embodiment 7, wherein the α2-3-linked sialoside is selected from the group consisting of Neu5Acα2-3Lac, Neu5Gcα2-3Lac, Neu5TFAα2-3Lac, Neu5Acα2-3LacβProN$_3$, Neu5Gcα2-3LacβProN$_3$, Neu5TFAα2-3LacβProN$_3$, Neu5Acα2-3LacβProNHCbz, Neu5Gcα2-3LacβProNHCbz, Neu5TFAα2-3LacβProNHCbz, Neu5Acα2-3LacβProNHFmoc, Neu5Gcα2-3LacβProNHFmoc, Neu5TFAα2-3LacβProNHFmoc, and derivatives thereof.

9. The method of any one of embodiments 1-8, wherein the sialic acid donor is a CMP-sialic acid.

10. The method of embodiment 9, wherein the glycoside acceptor is lactose or a lactoside.

11. The method of any one of embodiments 1-10, wherein the reaction mixture comprises a catalytic amount of the glycoside acceptor.

12. The method of any one of embodiments 1-11, wherein the sialyltransferase is PmST1_M144D comprising the amino acid sequence set forth in SEQ ID NO:4 or a catalytically active variant thereof.

13. The method of any one of embodiments 1-12, wherein forming the sialoside and forming the sialic acid product are conducted in one pot.

14. The method of any one of embodiments 1-12, wherein forming the sialoside and forming the sialic acid product are conducted in two separate reactions.

15. The method of any one of embodiments 9-14, further comprising contacting a sialic acid and a CMP-sialic acid synthetase in the presence of CTP to form the CMP-sialic acid.

16. The method of embodiment 15, wherein the CMP-sialic acid synthetase is NmCSS comprising the amino acid sequence set forth in SEQ ID NO:7, or a catalytically active variant thereof.

17. The method of embodiment 15 or 16, wherein forming the CMP-sialic acid, forming the sialoside, and forming the sialic acid product are conducted in one pot.

18. The method of any one of embodiments 15-17, further comprising contacting a C$_6$-monosaccharide and a sialic acid aldolase in the presence of pyruvate to form to the sialic acid.

19. The method of embodiment 18, wherein the sialic acid aldolase is PmAldolase comprising the amino acid sequence set forth in SEQ ID NO:8 or a catalytically active variant thereof.

20. The method of embodiment 18 or embodiment 19, wherein forming the sialic acid, forming the CMP-sialic acid, forming the sialoside, and forming the sialic acid product are conducted in one pot.

21. The method of any one of embodiments 1-20, further comprising acylating the sialic acid product.

22. The method of any one of embodiments 1-20, further comprising subjecting the sialic acid product to reductive amination conditions.

23. A compound according to Formula I:

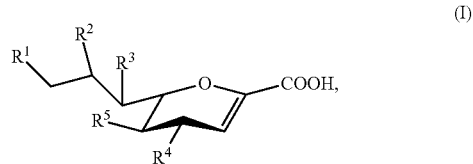

or a salt thereof, wherein:
$R^1$, $R^2$, $R^3$, and $R^4$ are independently selected from the group consisting of —NHC(O)R$^a$, —N$_3$, —NH$_2$, —NHR$^a$, —OC(O)R$^a$, —OH, and hydrogen;
$R^5$ is selected from the group consisting of —NHAc, —NHGc, —NHC(O)R$^a$, —N$_3$, —NH$_2$, —OC(O)R$^a$, —OH, and hydrogen;
each R$^a$ is independently selected from the group consisting of optionally substituted C$_{1-12}$ alkyl, optionally substituted C$_{1-12}$ haloalkyl, optionally substituted C$_{3-10}$ cycloalkyl, optionally substituted C$_{6-10}$ aryl, and optionally substituted C$_{7-22}$ arylalkyl;
Ac is —C(O)CH$_3$; and
Gc is —C(O)CH$_2$OH;
provided that at least one of $R^1$, $R^2$, $R^3$, and $R^4$ is other than —OH when $R^5$ is —NHAc or —NHGc.

24. The compound of embodiment 23, or a salt thereof, having a structure according to Formula Ia:

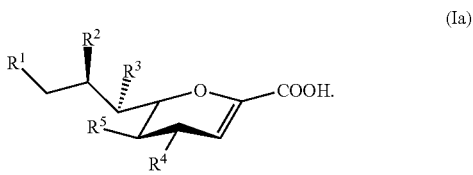

25. The compound of embodiment 23 or embodiment 24, or a salt thereof, wherein $R^1$ is —NHC(O)R$^a$.

26. The compound of any one of embodiments 23-25, or a salt thereof, wherein $R^3$ is selected from the group consisting of —OH and hydrogen.

27. The compound of any one of embodiments 23-26, or a salt thereof, wherein $R^5$ is selected from the group consisting of —NHAc, —NHGc, —NH$_2$, and —NHC(O)R$^a$.

28. The compound of embodiment 27, wherein $R^5$ is —NHC(O)R$^a$ and R$^a$ is trifluoromethyl.

29. The compound of embodiment 23, which is selected from the group consisting of:

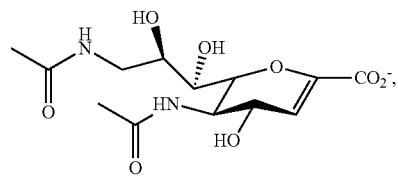

-continued

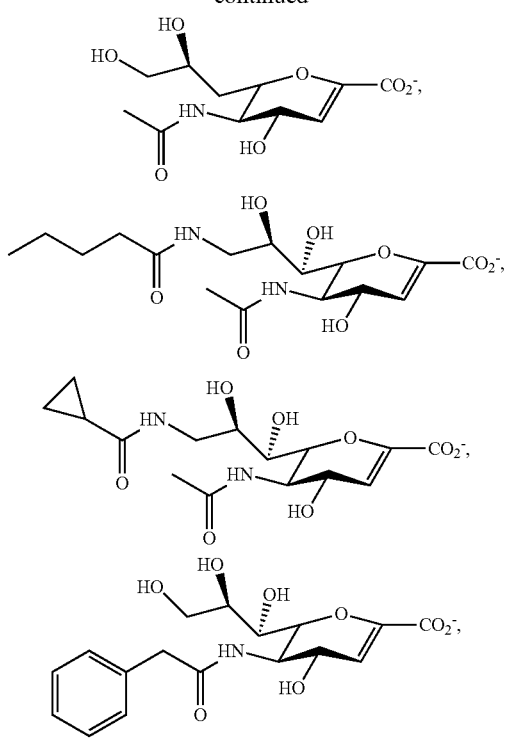

and salts thereof.

30. A compound according to Formula II:

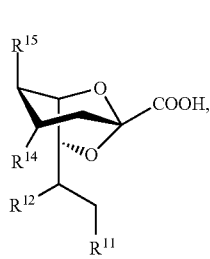

(II)

or a salt thereof, wherein:

$R^{11}$, $R^{12}$, and $R^{14}$ are independently selected from the group consisting of —NHC(O)$R^a$, —$N_3$, —$NH_2$, —NH$R^a$, —OC(O)$R^a$, —OH, and hydrogen;

$R^{15}$ is selected from the group consisting of —NHAc, —NHGc, —NHC(O)$R^a$, —$N_3$, —$NH_2$, —OC(O)$R^a$, —OH, and hydrogen;

$R^a$ is selected from the group consisting of optionally substituted $C_{1-12}$ alkyl, optionally substituted $C_{1-12}$ haloalkyl, optionally substituted $C_{3-10}$ cycloalkyl, optionally substituted $C_{6-10}$ aryl, and optionally substituted $C_{7-22}$ arylalkyl;

Ac is —C(O)CH$_3$; and

Gc is —C(O)CH$_2$OH;

provided that at least one of $R^{11}$, $R^{12}$, and $R^{14}$ is other than —OH when $R^{15}$ is —NHAc or —NHGc.

31. The compound of embodiment 30, or a salt thereof, having a structure according to Formula IIa:

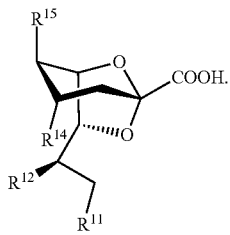

(IIa)

32. The compound of embodiment 30, or a salt thereof, wherein $R^{15}$ is selected from the group consisting of —NHAc, —NHGc, —NH$_2$, and —NHC(O)$R^a$.

33. The compound of embodiment 31, wherein $R^{15}$ is —NHC(O)$R^a$ and $R^a$ is trifluoromethyl.

34. The compound of embodiment 30, which is selected from the group consisting of

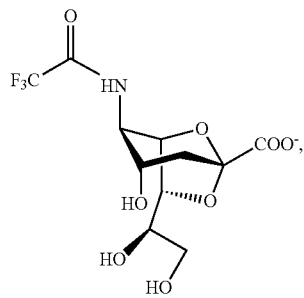

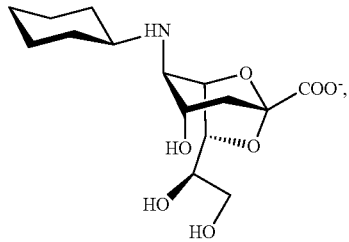

and salts thereof.

35. A pharmaceutical composition comprising a compound according to any one of embodiments 23-34 and a pharmaceutically acceptable excipient.

36. A method of inhibiting a sialidase comprising contacting the sialidase with an effective amount of a compound according to any one of embodiments 23-34

Although the foregoing has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

INFORMAL SEQUENCE LISTING
SpNanC (NCBI Accession No. WP_024478413.1)
SEQ ID NO: 1
KKNIKQYVTLGTVVVLSAFVANSVAAQETETSEVSTPELVQPVAPTTSISE

VQHKSGNSSEVTVQPRTVETTVKDPSSTAEETLVLEKNNVTLTGGGENVTK

ELKDKFTSGDFTVVIKYNQSSEKGLQALFGISNSKPGQQNSYVDVFLRDNG

ELGMEARDTSSNKNNLVSRPASVWGKYKQEAVTNTVAVVADSVKKTYSLYA

NGTKVVEKKVDNFLNIKDIKGIDYYMLGGVKRAGKTAFGFNGTLENIKFFN

SALDEETVKKMTTNAVTGHLIYTANDTTGSNYFRIPVLYTFSNGRVFSSID

ARYGGTHDFLNKINIATSYSDDNGKTWTKPKLTLAFDDFAPVPLEWPREVG

GRDLQISGGATYIDSVIVEKKNKQVLMFADVMPAGVSFREATRKDSGYKQI

DGNYYLKLRKQGDTDYNYTIRENGTVYDDRTNRPTEFSVDKNFGIKQNGNY

LTVEQYSVSFENNKKTEYRNGTKVHMNIFYKDALFKVVPTNYIAYISSNDH

GESWSAPTLLPPIMGLNRNAPYLGPGRGIIESSTGRILIPSYTGKESAFIY

SDDNGASWKVKVVPLPSSWSAEAQFVELSPGVIQAYMRTNNGKIAYLTSKD

AGTTWSAPEYLKFVSNPSYGTQLSIINYSQLIDGKKAVILSTPNSTNGRKH

GQIWIGLINDDNTIDWRYHHDVDYSNYGYSYSTLTELPNHEIGLMFEKFDS

WSRNELHMKNVVPYITFKIEDLKKN

*S. pneumoniae* TIGR4 SpNanC
(NCBI Accession No. AAK75424.1)
SEQ ID NO: 2
KKNIKQYVTLGTVVVLSAFVANSVAAQETETSEVSTPKLVQPVAPTTPISE

VQPTSDNSSEVTVQPRTVETTVKDPSSTAEETPVLEKNNVTLTGGGENVTK

ELKDKFTSGDFTVVIKYNQSSEKGLQALFGISNSKPGQQNSYVDVFLRDNG

ELGMEARDTSSNKNNLVSRPASVWGKYKQEAVTNTVAVVADSVKKTYSLYA

NGTKVVEKKVDNFLNIKDIKGIDYYMLGGVKRAGKTAFGFNGTLENIKFFN

SALDEETVKKMTTNAVTGHLIYTANDTTGSNYFRIPVLYTFSNGRVFSSID

ARYGGTHDFLNKINIATSYSDDNGKTWTKPKLTLAFDDFAPVPLEWPREVG

GRDLQISGGATYIDSVIVEKKNKQVLMFADVMPAGVSFREATRKDSGYKQI

DGNYYLKLRKQGDTDYNYTIRENGTVYDDRTNRPTEFSVDKNFGIKQNGNY

LTVEQYSVSFENNKKTEYRNGTKVHMNIFYKDALFKVVPTNYIAYISSNDH

GESWSAPTLLPPIMGLNRNAPYLGPGRGIIESSTGRILIPSYTGKESAFIY

SDDNGASWKVKVVPLPSSWSAEAQFVELSPGVIQAYMRTNNGKIAYLTSKD

AGTTWSAPEYLKFVSNPSYGTQLSIINYSQLIDGKKAVILSTPNSTNGRKH

GQIWIGLINDDNTIDWRYHHDVDYSNYGYSYSTLTELPNHEIGLMFEKFDS

WSRNELHMKNVVPYITFKIEDLKKN

*Streptococcus pneumoniae* SpNanB
(NCBI Accession No. NP_359124.1)
SEQ ID NO: 3
NELNYGQLSISPIFQGGSYQLNNKSIDISPLLLDKLSGDSQTVVMKFKADK

PNSLQALFGLSNSKAGFKNNYFSIFMRDSGEIGVEIRDAQKGINYLFSRPA

SLWGKHKGQAVENTLVFVSDSKDKTYTMYVNGIEVFSETVDTFLPISNING

IDKATLGAVNREGKEHYLAKGSIDEISLFNKAISDQEVSTIPLSNPFQLIF

QSGDSTQANYFRIPTLYTLSSGRVLSSIDARYGGTHDSKSKINIATSYSDD

NGKTWSEPIFAMKFNDYEEQLVYWPRDNKLKNSQISGSASFIDSSIVEDKK

SGKTILLADVMPAGIGNNNANKADSGFKEINGHYYLKLKKNGDNDFRYTVR

ENGVVYDETTNKPTNYTINDKYEVLEGGKSLTVEQYSVDFDSGSLRERHNG

KQVPMNVFYKDSLFKVTPTNYIAMTTSQNRGESWEQFKLLPPFLGEKHNGT

YLCPGQGLALKSSNRLIFATYTSGELTYLISDDSGQTWKKSSASIPFENAT

AEAQMVELRDGVIRTFFRTTTGKIAYMTSRDSGETWSEVSYIDGIQQTSYG

TQVSAIKYSQLIDGKEAVILSTPNSRSGRKGGQLVVGLVNKEDDSIDWKYH

YDIDLPSYGYAYSAITELPNHHIGVLFEKYDSWSRNELHLSNVVQYIDLEI

NDLTK

PmST1_M144D
SEQ ID NO: 4
KTITLYLDPASLPALNQLMDFTQNNEDKTHPRIFGLSRFKIPDNIITQYQN

IHFVELKDNRPTEALFTILDQYPGNIELNIHLNIAHSVQLIRPILAYRFKH

LDRVSIQQLNLYDDGSDEYVDLEKEENKDISAEIKQAEKQLSHYLLTGKIK

FDNPTIARYVWQSAFPVKYHFLSTDYFEKAEFLQPLKEYLAENYQKMDWTA

YQQLTPEQQAFYLTLVGFNDEVKQSLEVQQAKFIFTGTTTWEGNTDVREYY

AQQQLNLLNHFTQAEGDLFIGDHYKIYFKGHPRGGEINDYILNNAKNITNI

PANISFEVLMMTGLLPDKVGGVASSLYFSLPKEKISHIIFTSNKQVKSKED

ALNNPYVKVMRRLGIIDESQVIFWDSLKQL

PmST2
SEQ ID NO: 5
NLIICCTPLQVLIAEKIIAKFPHTPFYGVMLSTVSNKKFDFYAKRLAQQCQ

GFFSMVQHKDRFNLLKEILYLKRTFSGKHFDQVFVANINDLQIQFLLSAID

FNLLNTFDDGTINIVPNSLFYQDDPATLQRKLINVLLGNKYSIQSLRALSH

THYTIYKGFKNIIERVEPIELVAADNSEKVTSAVINVLLGQPVFAEDERNI

ALAERVIKQFNIHYYLPHPREKYRLAQVNYIDTELIFEDYILQQCQTHKYC

VYTYFSSAIINIMNKSDNIEVVALKIDTENPAYDACYDLFDELGVNVIDIR

E

PmST3Δ35
SEQ ID NO: 6
DKFAEHEIPKAVIVAGNGESLSQIDYRLLPKNYDVFRCNQFYFEERYFLGN

KIKAVFFTPGVFLEQYYTLYHLKRNNEYFVDNVILSSFNHPTVDLEKSQKI

QALFIDVINGYEKYLSKLTAFDVYLRYKELYENQRITSGVYMCAVAIAMGY

TDIYLTGIDFYQASEENYAFDNKKPNIIRLLPDFRKEKTLFSYHSKDIDLE

ALSFLQQHYHVNFYSISPMSPLSKHFPIPTVEDDCETTFVAPLKENYINDI

LLVDKLAAALE

NmCSS (NCBI Accession No. WP_025459740.1)
SEQ ID NO: 7
EKQNIAVILARQNSKGLPLKNLRKMNGISLLGHTINAAISSKCFDRIIVST

DGGLIAEEAKNFGVEVVLRPAELASDTASSISGVIHALETIGSNSGTVTLL

QPTSPLRTGAHIREAFSLFDEKIKGSVVSACPMEHHPLKTLLQINNGEYAP

MRHLSDLEQPRQQLPQAFRPNGAIYINDTASLIANNCFFIAPTKLYIMSHQ

DSIDIDTELDLQQAENILHHKES

-continued

PmAldolase (NCBI Accession No. WP_005723432.1)
SEQ ID NO: 8

TNIAIIPARAGSKGIPDKNLQPVGGHSLIGRAILAAKNADVFDMIVVTSDG
DNILREAEKYGALALKRPAELAQDNSRTIDAILHALESLNIREGTCTLLQP
TSPLRDHLDIKNAMDMYVNGGVHSVVSACECEHHPYKAFALSKDHEVLPVR
EIADFEAVRQTLPKMYRANGAIYINDIAQLLKEKYFFIPPLKFYLMPTYHS
VDIDVKQDLELAEILSNK

What is claimed is:

1. A method for preparing a 2-deoxy-2,3-dehydro-sialic acid, the method comprising:
   forming a reaction mixture comprising a glycoside acceptor, a sialic acid donor, and a sialyltransferase;
   maintaining the reaction mixture under conditions sufficient to form a sialoside; and
   contacting the sialoside with a *Streptococcus pneumoniae* sialidase to form the 2-deoxy-2,3-dehydro-sialic acid.

2. The method of claim 1, wherein the 2-deoxy-2,3-dehydro-sialic acid is a compound according to Formula I:

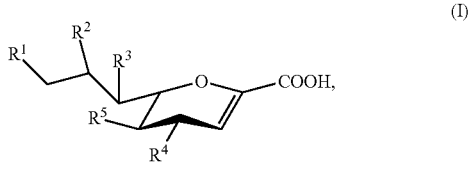

(I)

or a salt thereof, wherein:
   $R^1$, $R^2$, $R^3$, and $R^4$ are independently selected from the group consisting of —NHC(O)$R^a$, —$N_3$, —$NH_2$, —NH$R^a$, —OC(O)$R^a$, —OH, and hydrogen;
   $R^5$ is selected from the group consisting of —NHAc, —NHGc, —NHC(O)$R^a$, —$N_3$, —$NH_2$, —OC(O)$R^a$, —OH, and hydrogen;
   Ac is —C(O)$CH_3$;
   Gc is —C(O)$CH_2$OH; and
   each $R^a$ is independently selected from the group consisting of $C_{1-12}$ alkyl, $C_{1-12}$ haloalkyl, $C_{3-10}$ cycloalkyl, $C_{6-10}$ aryl, and $C_{7-22}$ arylalkyl.

3. The method of claim 2, wherein the *Streptococcus pneumoniae* sialidase is SpNanC having the amino acid sequence set forth in SEQ ID NO:1 or TIGR4 SpNanC having the amino acid sequence set forth in SEQ ID NO:2.

4. The method of claim 1, wherein the sialoside is an α2-3-linked sialoside.

5. The method of claim 4, wherein the α2-3-linked sialoside is selected from the group consisting of Neu5Acα2-3Lac, Neu5Gcα2-3Lac, Neu5TFAα2-3Lac, Neu5Acα2-3LacβProN$_3$, Neu5Gcα2-3LacβProN$_3$, Neu5TFAα2-3LacβProN$_3$, Neu5Acα2-3LacβProNHCbz, Neu5Gcα2-3LacβProNHCbz, Neu5TFAα2-3LacβProNHCbz, Neu5Acα2-3LacβProNHFmoc, Neu5Gcα2-3LacβProNHFmoc, and Neu5TFAα2-3LacβProNHFmoc.

6. The method of claim 1, wherein the sialyltransferase is PmST1_M144D comprising the amino acid sequence set forth in SEQ ID NO:4.

7. The method of claim 1, wherein the glycoside acceptor is a lactoside comprising a carboxybenzyl (Cbz)-protected amine or a fluorenylmethyloxycarbonyl (Fmoc)-protected amine.

8. The method of claim 7, wherein the glycoside acceptor is a lactoside Lacβ-OR, wherein R is Cbz-protected $C_{1-6}$ alkyl amine or Fmoc-protected $C_{1-6}$ alkyl amine.

9. The method of claim 8, wherein R is Cbz-protected propyl amine or Fmoc-protected propyl amine.

10. A method for preparing a 2,7-anhydro-sialic acid, the method comprising:
    forming a reaction mixture comprising a glycoside acceptor, a sialic acid donor, and a sialyltransferase, wherein the glycoside acceptor is a lactoside comprising a carboxybenzyl (Cbz)-protected amine or a fluorenylmethyloxycarbonyl (Fmoc)-protected amine;
    maintaining the reaction mixture under conditions sufficient to form a sialoside; and
    contacting the sialoside with a *Streptococcus pneumoniae* sialidase to form the 2,7-anhydro-sialic acid.

11. The method of claim 10, wherein the glycoside acceptor is a lactoside Lacβ-OR, wherein R is Cbz-protected $C_{1-6}$ alkyl amine or Fmoc-protected $C_{1-6}$ alkyl amine.

12. The method of claim 11, wherein R is Cbz-protected propyl amine or Fmoc-protected propyl amine.

13. The method of claim 10, wherein the 2,7-anhydro-sialic acid is a compound according to Formula II:

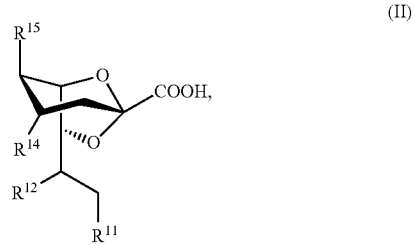

(II)

or a salt thereof, wherein:
   $R^{11}$, $R^{12}$, and $R^{14}$ are independently selected from the group consisting of —NHC(O)$R^a$, —$N_3$, —$NH_2$, —NH$R^a$, —OC(O)$R^a$, —OH, and hydrogen;
   $R^{15}$ is selected from the group consisting of —NHAc, —NHGc, —NHC(O)$R^a$, —$N_3$, —$NH_2$, —OC(O)$R^a$, —OH, and hydrogen;
   Ac is —C(O)$CH_3$;
   Gc is —C(O)$CH_2$OH; and
   each $R^a$ is independently selected from the group consisting of $C_{1-12}$ alkyl, $C_{1-12}$ haloalkyl, $C_{3-10}$ cycloalkyl, $C_{6-10}$ aryl, and $C_{7-22}$ arylalkyl.

14. The method of claim 10, wherein the *Streptococcus pneumoniae* sialidase is SpNanB having the amino acid sequence set forth in SEQ ID NO:3.

15. The method of claim 10, wherein the sialoside is an α2-3-linked sialoside.

16. The method of claim 15, wherein the α2-3-linked sialoside is selected from the group consisting of Neu5Acα2-3LacβProNHCbz, Neu5Gcα2-3LacβProNHCbz, Neu5TFAα2-3LacβProNHCbz, Neu5Acα2-3LacβProNHFmoc, Neu5Gcα2-3-LacβProNHFmoc, and Neu5TFAα2-3LacβProNHFmoc.

17. The method of claim 10, wherein the sialyltransferase is PmST1_M144D comprising the amino acid sequence set forth in SEQ ID NO:4.

* * * * *